US012655434B2

(12) United States Patent
Wang et al.

(10) Patent No.: US 12,655,434 B2
(45) Date of Patent: Jun. 16, 2026

(54) APTAMERS AND USE THEREOF

(71) Applicant: Aptitude Medical Systems, Inc., Goleta, CA (US)

(72) Inventors: Jinpeng Wang, Goleta, CA (US); Qiang Gong, Goleta, CA (US); Hui Kang, Goleta, CA (US); Qin Yang, Goleta, CA (US); Brian Ferguson, Goleta, CA (US)

(73) Assignee: Aptitude Medical Systems, Inc., Goleta, CA (US)

( * ) Notice: Subject to any disclaimer, the term of this patent is extended or adjusted under 35 U.S.C. 154(b) by 861 days.

(21) Appl. No.: 17/801,635

(22) PCT Filed: Feb. 25, 2021

(86) PCT No.: PCT/US2021/019649
§ 371 (c)(1),
(2) Date: Aug. 23, 2022

(87) PCT Pub. No.: WO2021/178209
PCT Pub. Date: Sep. 10, 2021

(65) Prior Publication Data

US 2023/0095004 A1 Mar. 30, 2023

Related U.S. Application Data

(60) Provisional application No. 62/984,339, filed on Mar. 3, 2020.

(51) Int. Cl.

| | |
|---|---|
| ***C12N 15/115*** | (2010.01) |
| ***A61K 31/7088*** | (2006.01) |
| ***A61P 27/02*** | (2006.01) |

(52) U.S. Cl.
CPC ........ *C12N 15/115* (2013.01); *A61K 31/7088* (2013.01); *A61P 27/02* (2018.01); *C12N 2310/322* (2013.01); *C12N 2310/33* (2013.01); *C12N 2310/531* (2013.01)

(58) Field of Classification Search
None
See application file for complete search history.

(56) References Cited

U.S. PATENT DOCUMENTS

| | | | | |
|---|---|---|---|---|
| 7,759,478 | B1 * | 7/2010 | Bentwich | C12N 15/111 536/23.1 |
| 2015/0322425 | A1 * | 11/2015 | Sullenger | C12Y 304/21022 506/1 |
| 2016/0003835 | A1 * | 1/2016 | Halbert | G01N 33/5308 506/9 |
| 2018/0258432 | A1 * | 9/2018 | Janjic | A61P 11/00 |
| 2022/0073922 | A1 * | 3/2022 | Wang | A61K 31/7115 |

OTHER PUBLICATIONS

Nonaka et al. Molecules 15, 215-225 (Year: 2010).*
Minseon Cho et al. "Array-based discovery of Aptamer Pairs", Analytical Chemistry, vol. 87, No. 1, Dec. 11, 2014, p. 821-828.
Minseon Cho et al. "Supporting information—Array-based discovery of Aptamer Pairs", Analytical Chemistry, vol. 87, No. 1, Dec. 11, 2014.
EESR search report for EP 21765075, Dated Mar. 13, 2024.

* cited by examiner

*Primary Examiner* — Brian Whiteman
(74) *Attorney, Agent, or Firm* — IPro, PLLC; Na Xu

(57) ABSTRACT

The present disclosure provides an anti-VEGF aptamer, an agent or composition comprising the anti-VEGF aptamer, as well as uses thereof.

3 Claims, 12 Drawing Sheets

Specification includes a Sequence Listing.

AMS0433

A

SEQ ID NO: 128

C

AMSB107

SEQ ID NO: 171

APTAMERS AND USE THEREOF

BACKGROUND

Neovascularization (NV) and vascular leakage are hallmarks of multiple neovascular retinal diseases such as Diabetic Macular Edema (DME), wet Age-related Macular Degeneration (AMD), and Diabetic Retinopathy (DR).

VEGF plays a pivotal role in regulating angiogenesis which is the main mechanism of ocular NV, and vascular permeability which determines the extent of leakage, and thus is an effective target for various diseases.

The Ang2/Tie2 pathway is proven by extensive research to be an important complementary player of VEGF, holding great potential as a novel target for the treatment of various diseases, such as retinal diseases. As reported, Tie2 is a tyrosine kinase receptor for both Angiopoietin-1 (Ang1) and Angiopoietin-2 (Ang2), located on the surface of vascular endothelial cells. Ang2 is only expressed under pathological conditions. It complements VEGF's function by promoting vascular permeability and stimulating the secretion of proangiogenic cytokines, which are required for VEGF-induced ocular NV and vascular leakage.

Current anti-VEGF drugs, despite their success, still suffer from limited efficacy and duration. Increasing the dosage of anti-VEGF agents may improve both drug potency and duration. Nucleic acid aptamers possess a high solubility and a small molecular weight (~15 kDa), and thus may achieve a much higher molar dosage.

However, the previous anti-VEGF aptamer, e.g., Macugen® cannot realize this potential. Macugen® fails to recognize all VEGFA isoforms and accordingly has inferior potency. Thus, there is an urgent need to develop aptamers that are more effective than those in the art.

There is ongoing need to develop aptamers targeting VEGF and/or Ang2 that are more specific, with higher affinity, and/or more effective.

SUMMARY OF THE INVENTION

The present disclosure provides an anti-VEGF aptamer, an anti-Ang2 aptamer, a bispecific aptamer and a composition comprising the anti-VEGF aptamer and/or the anti-Ang2 aptamer, and uses thereof.

The anti-VEGF aptamer provided in the present disclosure is capable of at least one of the followings: 1) binding to all VEGFA isoforms (e.g. VEGF-121, VEGF-165 and VEGF 189) with a $K_D$ value of about 20 nanomolar (nM) or less; 2) forming a specific secondary structure, comprising, from 5' to 3' direction, a first stem, a first loop, a second stem and a second loop; 3) being formulated at a concentration of as high as 200 mg/ml or more; 4) being nuclease resistant; 5) binding to VEGFA isoforms from various species, such as human VEGFs, mouse VEGFs, rat VEGFs, rabbit VEGFs, and monkey VEGFs; 6) inhibiting an interaction between a VEGF and a VEGF receptor; and 7) preventing, treating, and/or ameliorating a neovascular disease, disorder or condition.

The anti-Ang2 aptamer provided in the present disclosure is capable of at least one of the followings: 1) binding to Ang2 with a $K_D$ value of about 500 picomolar (pM) or less; 2) not substantially binding to human Ang1; 3) forming a specific secondary structure comprising, from 5' to 3' direction, a first stem, a first bulge, a second stem, a second bulge, a third stem, a third bulge, a fourth stem, and a first loop; 4) binding to both a human Ang2 and a mouse Ang2; 5) being nuclease resistant; 6) inhibiting an interaction between Ang2 and Tie2; and 7) preventing, treating, and/or ameliorating a neovascular disease, disorder or condition.

The bispecific aptamer and/or the composition provided in the present disclosure is capable of at least one of the followings: 1) binding to all VEGFA isoforms (e.g. VEGF-121, VEGF-165 and VEGF 189) with a $K_D$ value of about 20 nanomolar (nM) or less; 2) binding to Ang2 with a $K_D$ value of about 500 picomolar (pM) or less; 3) being nuclease resistant; 4) inhibiting an interaction between Ang2 and Tie2; 5) inhibiting an interaction between a VEGF and a VEGF receptor; and 6) preventing, treating, and/or ameliorating a neovascular disease, disorder or condition.

Anti-VEGF Aptamer

In one aspect, the present disclosure provides an anti-VEGF aptamer, which binds to VEGF-121 with a $K_D$ value of about 20 nanomolar (nM) or less, and binds to VEGF-165 with a $K_D$ value of about 20 nanomolar (nM) or less.

In some embodiments, the anti-VEGF aptamer binds to VEGF-121 with a $K_D$ value of about 2 nanomolar (nM) or less. In some embodiments, the anti-VEGF aptamer binds to VEGF-165 with a $K_D$ value of about 2 nanomolar (nM) or less.

In some embodiments, the VEGF-121 is a human VEGF-121, a mouse VEGF-120, a monkey VEGF-121, a rabbit VEGF-121 and/or a rat VEGF-120. In some embodiments, the VEGF-165 is a human VEGF-165, a mouse VEGF-164, a monkey VEGF-165, a rabbit VEGF-165 and/or a rat VEGF-164. In some embodiments, the anti-VEGF aptamer binds to VEGF-189, such as the rabbit VEGF-189.

In some embodiments, the anti-VEGF aptamer specifically binds to both a VEGF receptor-binding domain of VEGF-121 or a fragment thereof and a VEGF receptor-binding domain of VEGF-165 or a fragment thereof.

In some embodiments, the VEGF receptor-binding domain of VEGF-121 comprises an amino acid sequence as set forth in any one of SEQ ID NO: 30-34, 40, 41 and 45. In some embodiments, the VEGF receptor-binding domain of VEGF-165 comprises an amino acid sequence as set forth in any one of SEQ ID NO: 30-34, 40 and 41.

In some embodiments, the anti-VEGF aptamer inhibits an interaction between said VEGF-121 and VEGF-R1. In some embodiments, the anti-VEGF aptamer inhibits an interaction between said VEGF-121 and VEGF-R2.

In some embodiments, the anti-VEGF aptamer inhibits an interaction between said VEGF-165 and VEGF-R1. In some embodiments, the anti-VEGF aptamer inhibits an interaction between said VEGF-165 and VEGF-R2.

In some embodiments, the anti-VEGF aptamer is capable of reducing and/or ameliorating a lesion and/or a leakage in a laser-induced choroidal neovascularization (CNV) rat model.

In some embodiments, the anti-VEGF aptamer is capable of reducing and/or ameliorating a lesion and/or a leakage in a non-human primate (NHP) laser-induced CNV model.

In some embodiments, the anti-VEGF aptamer is highly soluble.

In some embodiments, the anti-VEGF aptamer is an RNA aptamer, a DNA aptamer, or a combination thereof. In some embodiments, the anti-VEGF aptamer comprises one or more modified nucleotide. In some embodiments, the anti-VEGF aptamer is nuclease resistant. In some embodiments, all the nucleotides of the anti-VEGF aptamer are modified nucleotides. In some embodiments, such modified nucleotide comprises a chemical substitution or modification at one or more positions independently selected from a ribose position, a deoxyribose position, a phosphate position, and a base position. In some embodiments, the modified nucleotide comprises one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. In some embodiments, the 5-position modified pyrimidine is selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, the anti-VEGF aptamer comprises at least one 2'-modified nucleotides. In some embodiments, all the nucleotides of the anti-VEGF aptamer are 2'-modified nucleotides. In some embodiments, the 2'-modified nucleotide is selected from a 2'-amino-modified nucleotide, a 2'-fluoro-modified nucleotide, and a 2'-O-methyl-modified nucleotide, and a 2'-O-(2-methoxyethyl)-modified nucleotide. In some embodiments, the aptamer comprises at least one 2'-fluoro-modified nucleotide, at least one 2'-O-methyl-modified nucleotide, and/or at least one LNA.

In some embodiments, all the cytidines of the anti-VEGF aptamer are 2'-modified cytidines. In some embodiments, all the cytidines of the anti-VEGF aptamer are 2'-fluoro-modified cytidines and/or 2'-O-methyl-modified cytidines. In some embodiments, all the cytidines of the anti-VEGF aptamer are 2'-deoxy-2'-fluorocytidines. In some embodiments, all the uridines of the anti-VEGF aptamer are 2'-modified uridines. In some embodiments, all the uridines of the anti-VEGF aptamer are 2'-fluoro-modified uridines and/or 2'-O-methyl-modified uridines. In some embodiments, all the uridines of the anti-VEGF aptamer are 2'-deoxy-2'-fluorouridines. In some embodiments, all the adenosines of the anti-VEGF aptamer are 2'-modified adenosines. In some embodiments, all the adenosines of the anti-VEGF aptamer are 2'-fluoro-modified adenosines and/or 2'-O-methyl-modified adenosines. In some embodiments, all the adenosines of the anti-VEGF aptamer are 2'-deoxy-2'-fluoroadenosines. In some embodiments, all the guanosines of the anti-VEGF aptamer are 2'-modified guanosines. In some embodiments, all the guanosines of the anti-VEGF aptamer are 2'-fluoro-modified guanosines and/or 2'-O-methyl-modified guanosines. In some embodiments, all the guanosines of the anti-VEGF aptamer are 2'-deoxy-2'-fluoroguanosines.

In some embodiments, all the nucleotides of the anti-VEGF aptamer are 2'-fluoro-modified nucleotides and/or 2'-O-methyl-modified nucleotides.

In some embodiments, all the nucleotides of the anti-VEGF aptamer are 2'-fluoro-modified nucleotides.

In some embodiments, the anti-VEGF aptamer does not comprise any natural nucleotide.

In some embodiments, the anti-VEGF aptamer comprises about 10 to about 150 nucleotides.

In some embodiments, the anti-VEGF aptamer competes with an anti-VEGF reference aptamer for binding to the VEGF-165 and/or to the VEGF-121, wherein the anti-VEGF reference aptamer comprises a secondary structure comprising (e.g., from 5' to 3' direction), a first stem, a first loop, a second stem and a second loop.

In some embodiments, the anti-VEGF reference aptamer comprises a secondary structure consisting of (e.g., from 5' to 3' direction), a first stem, a first loop, a second stem and a second loop.

In some embodiments, the anti-VEGF reference aptamer comprises a first consensus sequence comprising a nucleotide sequence as set forth in any of SEQ ID NO: 136-137. In some embodiments, the anti-VEGF reference aptamer comprises a second consensus sequence comprising a nucleotide sequence as set forth in any of SEQ ID NO: 138-139.

In some embodiments, the first consensus sequence comprises the nucleotide sequence forming the first stem and the first loop of the anti-VEGF reference aptamer. In some embodiments, the first consensus sequence is not comprised in the nucleotide sequence forming the second stem or the second loop of the anti-VEGF reference aptamer. In some embodiments, the second consensus sequence comprises the nucleotide sequence forming the second stem and the second loop of the anti-VEGF reference aptamer. In some embodiments, the second consensus sequence is not comprised in the nucleotide sequence forming the first stem or the first loop of the anti-VEGF reference aptamer.

In some embodiments, the anti-VEGF reference aptamer comprises a nucleotide sequence as set forth in any of SEQ ID NO: 46-135, SEQ ID NO: 200-201 or a variant or truncate thereof. In some embodiments, the variant comprises a nucleotide sequence that is at least 50% identical to the nucleotide sequence as set forth in any of SEQ ID NO: 46-135, SEQ ID NO: 200-201. In some embodiments, the variant comprises a nucleotide sequence as set forth in any of SEQ ID NO: 46-135, SEQ ID NO: 200-201 with one or more nucleotide addition, deletion, and/or substitution. In some embodiments, the anti-VEGF reference aptamer comprises about 10 to about 150 nucleotides.

In some embodiments, the anti-VEGF reference aptamer comprises the first consensus sequence and the second consensus sequence and the first consensus sequence is located 5' to second consensus sequence.

In embodiments, the anti-VEGF reference aptamer comprises the first consensus sequence and the second consensus sequence and the second consensus sequence is located 5' to the first consensus sequence.

In some embodiments, the anti-VEGF aptamer comprises a secondary structure comprising (e.g., from 5' to 3' direction), a first stem, a first loop, a second stem and a second loop. In some embodiments, the anti-VEGF aptamer comprises a secondary structure consisting of (e.g., from 5' to 3' direction), a first stem, a first loop, a second stem and a second loop.

In some embodiments, the anti-VEGF aptamer comprises a first consensus sequence comprising a nucleotide sequence as set forth in any of SEQ ID NO: 136-137. In some embodiments, the anti-VEGF aptamer comprises a second consensus sequence comprising a nucleotide sequence as set forth in any of SEQ ID NO: 138-139.

In some embodiments, the first consensus sequence comprises the nucleotide sequence forming the first stem and the first loop of the anti-VEGF aptamer. In some embodiments, the first consensus sequence is not comprised in the nucleotide sequence forming the second stem or the second loop of the anti-VEGF aptamer. In some embodiments, the second consensus sequence comprises the nucleotide sequence forming the second stem and the second loop of the anti-VEGF aptamer. In some embodiments, the second consensus sequence is not comprised in the nucleotide sequence forming the first stem or the first loop of the anti-VEGF aptamer.

In some embodiments, the anti-VEGF aptamer comprises a nucleotide sequence as set forth in any of SEQ ID NO: 46-135, SEQ ID NO: 200-201, or a variant or truncate thereof. In some embodiments, the variant comprises a nucleotide sequence that is at least 50% identical to the nucleotide sequence as set forth in any of SEQ ID NO: 46-135, SEQ ID NO: 200-201. In some embodiments, the variant comprises a nucleotide sequence as set forth in any of SEQ ID NO: 46-135, SEQ ID NO: 200-201, with one or more nucleotide addition, deletion, and/or substitution.

In some embodiments, the anti-VEGF aptamer comprises the first consensus sequence and the second consensus sequence, and the first consensus sequence is located 5' to the second consensus sequence. In some embodiments, the anti-VEGF aptamer comprises the first consensus sequence and the second consensus sequence, and the second consensus sequence is located 5' to the first consensus sequence.

In some embodiments, the anti-VEGF aptamer is used for modulating the biological activity of a VEGF or a VEGF receptor.

In some embodiments, the anti-VEGF aptamer is used for preventing, treating, and/or ameliorating a VEGF related disease, disorder or condition. In some embodiments, the VEGF related disease, disorder or condition is a neovascular disease, disorder or condition. In some embodiments, the VEGF related disease, disorder or condition is an ocular neovascular disease, disorder or condition. In some embodiments, the VEGF related disease, disorder or condition is selected from age-related macular degeneration, choroidal neovascularization, diabetic macular edema, retinal vein occlusion, and diabetic retinopathy. In some embodiments, the VEGF related disease, disorder or condition is selected from wet age-related macular degeneration, myopic choroidal neovascularization, and proliferative diabetic retinopathy.

In one aspect, the present disclosure provides an anti-VEGF agent, comprising the anti-VEGF aptamer of the present disclosure. In some embodiments, the anti-VEGF agent further comprises a polyethylene glycol (PEG) moiety. In some embodiments, the PEG moiety is conjugated to the 5' terminus of the aptamer.

In one aspect, the present disclosure provides a composition, comprising the anti-VEGF aptamer, or the anti-VEGF agent of the present disclosure.

In some embodiment, the composition is a pharmaceutical composition. In some embodiment, the composition comprises a pharmaceutically acceptable excipient or carrier. In some embodiment, the composition comprises a therapeutically effective amount of the anti-VEGF aptamer or the anti-VEGF agent.

In one aspect, the present disclosure provides a method for modulating the biological activity of a VEGF and/or a VEGF receptor, comprising administering to a subject in need thereof an effective amount of the anti-VEGF aptamer or the anti-VEGF agent of the present disclosure.

In one aspect, the present disclosure provides a method for preventing, treating, and/or ameliorating a VEGF related disease, disorder or condition, comprising administering to a subject in need thereof an effective amount of the anti-VEGF aptamer or the anti-VEGF agent of the present disclosure. In some embodiments, the VEGF related disease, disorder or condition is a neovascular disease, disorder or condition. In some embodiments, the VEGF related disease, disorder or condition is an ocular neovascular disease, disorder or condition. In some embodiment, the VEGF related disease, disorder or condition is selected from age-related macular degeneration, choroidal neovascularization, diabetic macular edema, retinal vein occlusion, and diabetic retinopathy. In some embodiments, the VEGF related disease, disorder or condition is selected from wet age-related macular degeneration, myopic choroidal neovascularization, and proliferative diabetic retinopathy.

In one aspect, the present disclosure provides a use of the anti-VEGF aptamer, or the anti-VEGF agent of the present disclosure in the manufacture of an agent for modulating the biological activity of a VEGF or a VEGF receptor.

In one aspect, the present disclosure provides a use of the anti-VEGF aptamer, or the anti-VEGF agent of the present disclosure, in the manufacture of a medicament for preventing, treating, and/or ameliorating a VEGF related disease, disorder or condition. In some embodiments, the VEGF related disease, disorder or condition is a neovascular disease, disorder or condition. In some embodiments, the VEGF related disease, disorder or condition is an ocular neovascular disease, disorder or condition. In some embodiments, the VEGF related disease, disorder or condition is selected from age-related macular degeneration, choroidal neovascularization, diabetic macular edema, retinal vein occlusion, and diabetic retinopathy. In some embodiments, the VEGF related disease, disorder or condition is selected from wet age-related macular degeneration, myopic choroidal neovascularization, and proliferative diabetic retinopathy.

Anti-Ang2 Aptamer

In one aspect, the present disclosure provides an anti-Ang2 aptamer that specifically binds to Ang2 with a $K_D$ value of about 500 picomolar (pM) or less.

In some embodiments, the anti-Ang2 aptamer binds to Ang2 with a $K_D$ value of about 100 picomolar (pM) or less.

In some embodiments, the Ang2 is a human Ang2, a mouse Ang2, a monkey Ang2, a rabbit Ang 2, and/or a rat Ang2.

In some embodiments, the anti-Ang2 aptamer does not substantially bind to human Ang1.

In some embodiments, the anti-Ang2 aptamer inhibits an interaction between the Ang2 and Tie2.

In some embodiments, the anti-Ang2 aptamer is capable of reducing neovascularization and/or reducing vascular permeability in a mouse oxygen-induced ischemic retinopathy (OIR) model.

In some embodiments, the anti-Ang2 aptamer is highly soluble.

In some embodiments, the anti-Ang2 aptamer is an RNA aptamer, a DNA aptamer, or a combination thereof. In some embodiments, the anti-Ang2 aptamer comprises one or more modified nucleotides. In some embodiments, the anti-Ang2 aptamer is nuclease resistant. In some embodiments, all the nucleotides of the anti-Ang2 aptamer are modified nucleotides. In some embodiments, the modified nucleotide comprises a chemical substitution or modification at one or more positions independently selected from a ribose position, a deoxyribose position, a phosphate position, and a base position. In some embodiments, the modified nucleotide comprises one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. In some embodiments, the 5-position modified pyrimidine is selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, the anti-Ang2 aptamer comprises at least one 2'-modified nucleotides. In some embodiments, all the nucleotides of the anti-Ang2 aptamer are 2'-modified nucleotides. In some embodiments, the 2'-modified nucleotide is selected from a 2'-amino-modified nucleotide, a 2'-fluoro-modified nucleotide, and a 2'-O-methyl-modified nucleotide and a 2'-O-methoxyl-modified nucleotide.

In some embodiments, the anti-Ang2 aptamer comprises at least one 2'-fluoro-modified nucleotide, at least one 2'-O-methyl-modified nucleotide, and/or at least one LNA. In some embodiments, all the cytidines of the anti-Ang2 aptamer are 2'-modified cytidines. In some embodiments, all the cytidines of the anti-Ang2 aptamer are 2'-fluoro-modified cytidines and/or 2'-O-methyl-modified cytidines. In some embodiments, all the cytidines of the anti-Ang2 aptamer are 2'-deoxy-2'-fluorocytidines. In some embodiments, all the uridines of the anti-Ang2 aptamer are 2'-modified uridines. In some embodiments, all the uridines of the anti-Ang2 aptamer are 2'-fluoro-modified uridines and/or 2'-O-methyl-modified uridines. In some embodiments, all the uridines of the anti-Ang2 aptamer are 2'-deoxy-2'-fluorouridines. In some embodiments, all the adenosines of the anti-Ang2 aptamer are 2'-modified adenosines. In some embodiments, all the adenosines of the anti-Ang2 aptamer are 2'-fluoro-modified adenosines and/or 2'-O-methyl-modified adenosines. In some embodiments, all the adenosines of the anti-Ang2 aptamer are 2'-deoxy-2'-fluoroadenosines. In some embodiments, all the guanosines of the anti-Ang2 aptamer are 2'-modified guanosines. In some embodiments, all the guanosines of the anti-Ang2 aptamer are 2'-fluoro-modified guanosines and/or 2'-O-methyl-modified guanosines. In some embodiments, all the guanosines of the anti-Ang2 aptamer are 2'-deoxy-2'-fluoroguanosines. In some embodiments, all the nucleotides of the anti-Ang2 aptamer are 2'-fluoro-modified nucleotides and/or 2'-O-methyl-modified nucleotides. In some embodiments, all the nucleotides of the anti-Ang2 aptamer are 2'-fluoro-modified nucleotides.

In some embodiments, the anti-Ang2 aptamer does not comprise any natural nucleotide. In some embodiments, the anti-Ang2 aptamer comprises about 10 to about 150 nucleotides.

In some embodiments, the anti-Ang2 aptamer competes with an anti-Ang2 reference aptamer for binding to the Ang2, wherein the anti-Ang2 reference aptamer comprises a secondary structure comprising, from 5' to 3' direction, a first stem, a first bulge, a second stem, a second bulge, a third stem, a third bulge, a fourth stem, and a first loop.

In some embodiments, the anti-Ang2 reference aptamer comprises a secondary structure consisting of, from 5' to 3' direction, a first stem, a first bulge, a second stem, a second bulge, a third stem, a third bulge, a fourth stem, and a first loop.

In some embodiments, the anti-Ang2 reference aptamer comprises a first consensus sequence comprising a nucleotide sequence as set forth in any of SEQ ID NO: 13-20. In some embodiments, the anti-Ang2 reference aptamer comprises a second consensus sequence comprising a nucleotide sequence as set forth in any of SEQ ID NO: 21-28.

In some embodiments, the first consensus sequence is comprised in the nucleotide sequence forming the first bulge, the second stem, the second bulge, the third stem, the third bulge and/or the fourth stem of the anti-Ang2 reference aptamer. In some embodiments, the first consensus sequence is not comprised in the nucleotide sequence forming first loop of the anti-Ang2 reference aptamer.

In some embodiments, the second consensus sequence is comprised in the nucleotide sequence forming the first bulge, the second stem, the second bulge, the third stem, the third bulge and/or the fourth stem of the anti-Ang2 reference aptamer. In some embodiments, the second consensus sequence is not comprised in the nucleotide sequence forming first loop of the anti-Ang2 reference aptamer.

In some embodiments, the anti-Ang2 reference aptamer comprises a nucleotide sequence as set forth in any of SEQ ID NO: 1-12, or a variant or truncate thereof. In some embodiments, the variant comprises a nucleotide sequence that is at least 50% identical to the nucleotide sequence as set forth in any of SEQ ID NO: 1-12. In some embodiments, the variant comprises a nucleotide sequence as set forth in any of SEQ ID NO: 1-12, with one or more nucleotide addition, deletion, and/or substitution. In some embodiments, the anti-Ang2 reference aptamer comprises about 10 to about 150 nucleotides.

In some embodiments, the anti-Ang2 reference aptamer comprises the first consensus sequence and the second consensus sequence, and the first consensus sequence is located 5' to the second consensus sequence.

In some embodiments, the anti-Ang2 aptamer comprises a secondary structure comprising, from 5' to 3' direction, a first stem, a first bulge, a second stem, a second bulge, a third stem, a third bulge, a fourth stem, and a first loop. In some embodiments, the anti-Ang2 aptamer comprises a secondary structure consisting of, from 5' to 3' direction, a first stem, a first bulge, a second stem, a second bulge, a third stem, a third bulge, a fourth stem, and a first loop.

In some embodiments, the anti-Ang2 aptamer comprises a first consensus sequence comprising a nucleotide sequence as set forth in any of SEQ ID NO: 13-20. In some embodiments, the anti-Ang2 aptamer comprises a second consensus sequence comprising a nucleotide sequence as set forth in any of SEQ ID NO: 21-28.

In some embodiments, the first consensus sequence is comprised in the nucleotide sequence forming the first bulge, the second stem, the second bulge, the third stem, the third bulge and/or the fourth stem of the anti-Ang2 aptamer. In some embodiments, the first consensus sequence is not comprised in the nucleotide sequence forming first loop of the anti-Ang2 aptamer. In some embodiments, the second consensus sequence is comprised in the nucleotide sequence forming the first bulge, the second stem, the second bulge, the third stem, the third bulge and/or the fourth stem of the anti-Ang2 aptamer. In some embodiments, the second consensus sequence is not comprised in the nucleotide sequence forming first loop of the anti-Ang2 aptamer.

The first loop of the anti-Ang2 reference aptamer or the anti-Ang2 aptamer of the present disclosure may comprise 2-30 nucleotides.

In some embodiments, the anti-Ang2 aptamer comprises a nucleotide sequence as set forth in any of SEQ ID NO: 1-12, or a variant or truncate thereof. In some embodiments, the variant comprises a nucleotide sequence that is at least 50% identical to the nucleotide sequence as set forth in any of SEQ ID NO: 1-12. In some embodiments, the variant comprises a nucleotide sequence as set forth in any of SEQ ID NO: 1-12, with one or more nucleotide addition, deletion, and/or substitution.

In some embodiments, the anti-Ang2 aptamer comprises the first consensus sequence and the second consensus sequence, and the first consensus sequence is located 5' to the second consensus sequence.

In some embodiments, the anti-Ang2 aptamer comprises the first consensus sequence and the second consensus sequence, and the second consensus sequence is located 5' to the first consensus sequence.

In some embodiments, the anti-Ang2 aptamer is used for modulating the biological activity of Ang2 or Tie2.

In some embodiments, the anti-Ang2 aptamer is used for preventing, treating, and/or ameliorating an Ang2 related disease, disorder or condition. In some embodiments, the Ang2 related disease, disorder or condition is a neovascular disease, disorder or condition. In some embodiments, the Ang2 related disease, disorder or condition is an ocular neovascular disease, disorder or condition. In some embodiments, the Ang2 related disease, disorder or condition is selected from age-related macular degeneration, choroidal neovascularization, diabetic macular edema, retinal vein occlusion, and diabetic retinopathy. In some embodiments, the Ang2 related disease, disorder or condition is selected from age-related macular degeneration, choroidal neovascularization, diabetic macular edema, retinal vein occlusion, and diabetic retinopathy.

In one aspect, the present disclosure provides an anti-Ang2 agent, comprising the anti-Ang2 aptamer of the present disclosure. In some embodiments, the anti-Ang2 agent further comprises a polyethylene glycol (PEG) moiety. In some embodiments, the PEG moiety is conjugated to the 3' terminus of the anti-Ang2 aptamer.

In one aspect, the present disclosure provides a composition, comprising the anti-Ang2 aptamer, or the anti-Ang2 agent of the present disclosure.

In some embodiments, the composition is a pharmaceutical composition. In some embodiments, the composition comprises a pharmaceutically acceptable excipient or carrier. In some embodiments, the composition comprises an effective amount of the anti-Ang2 aptamer or the anti-Ang2 agent.

In some embodiments, the composition further comprises an anti-VEGF agent. In some embodiments, the anti-VEGF agent comprises Aflibercept.

In one aspect, the present disclosure provides a method for modulating the biological activity of Ang2 or Tie2, comprising administering to a subject in need thereof an effective amount of the anti-Ang2 aptamer, or the anti-Ang2 agent of the present disclosure.

In one aspect, the present disclosure provides a method for preventing, treating, and/or ameliorating an Ang2 related disease, disorder or condition, comprising administering to a subject in need thereof an effective amount of the anti-Ang2 aptamer or the anti-Ang2 agent of the present disclosure.

In some embodiments, the Ang2 related disease, disorder or condition is a neovascular disease, disorder or condition. In some embodiments, the Ang2 related disease, disorder or condition is selected from age-related macular degeneration, choroidal neovascularization, diabetic macular edema, retinal vein occlusion, and diabetic retinopathy. In some embodiments, the Ang2 related disease, disorder or condition is selected from wet age-related macular degeneration, myopic choroidal neovascularization, and proliferative diabetic retinopathy. In some embodiments, the method further comprises administering to the subject an anti-VEGF agent. In some embodiments, the anti-VEGF agent comprises Aflibercept.

In one aspect, the present disclosure provides a use of the anti-Ang2 aptamer, or the anti-Ang2 agent of the present disclosure in the manufacture of an agent for modulating the biological activity of Ang2 or Tie2.

In one aspect, the present disclosure provides a use of the anti-Ang2 aptamer, or the anti-Ang2 agent of the present disclosure in the manufacture of a medicament for preventing, treating, and/or ameliorating an Ang2 related disease, disorder or condition.

In some embodiments, the Ang2 related disease, disorder or condition is a neovascular disease, disorder or conditions. In some embodiments, the Ang2 related disease, disorder or condition is an ocular neovascular disease, disorder or condition. In some embodiments, the Ang2 related disease, disorder or condition is selected from age-related macular degeneration, choroidal neovascularization, diabetic macular edema, retinal vein occlusion, and diabetic retinopathy. In some embodiments, the Ang2 related disease, disorder or condition is selected from wet age-related macular degeneration, myopic choroidal neovascularization, and proliferative diabetic retinopathy.

In one aspect, the present disclosure provides a use of 1) the anti-Ang2 aptamer, or the anti-Ang2 agent of the present disclosure in combination with 2) an anti-VEGF agent in the manufacture of a medicament for preventing, treating, and/or ameliorating a neovascular disease, disorder or condition. In some embodiments, the anti-VEGF agent comprises Aflibercept. In some embodiments, the neovascular disease or disorder is an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

Bispecific Aptamer

In another aspect, the present disclosure provides a bispecific aptamer comprising an anti-Ang2 aptamer and an anti-VEGF aptamer. The bispecific aptamer may be comprised in the composition of the present disclosure.

In some embodiments, the anti-VEGF aptamer binds to VEGF-121 with a $K_D$ value of about 20 nanomolar (nM) or less, and binds to VEGF-165 with a $K_D$ value of about 20 nanomolar (nM) or less.

In some embodiments, the anti-Ang2 aptamer specifically binds to Ang2 with a $K_D$ value of about 500 picomolar (pM) or less.

In some embodiments, the anti-VEGF aptamer binds to VEGF-121 with a $K_D$ value of about 2 nanomolar (nM) or less. In some embodiments, the anti-VEGF aptamer binds to VEGF-165 with a $K_D$ value of about 2 nanomolar (nM) or less.

In some embodiments, the VEGF-121 is a human VEGF-121, a mouse VEGF-120, a monkey VEGF-121, a rabbit VEGF-121, and or a rat VEGF-120. In some embodiments, the VEGF-165 is a human VEGF-165, a mouse VEGF-164, a monkey VEGF-165, a rabbit VEGF-165, or a rat VEGF-164.

In some embodiments, the anti-VEGF aptamer specifically binds to both a VEGF receptor-binding domain of VEGF-121 and a VEGF receptor-binding domain of VEGF-165.

In some embodiments, the VEGF receptor-binding domain of VEGF-121 comprises an amino acid sequence as set forth in any one of SEQ ID NO: 30-34, 40, 41, and 45. In some embodiments, the VEGF receptor-binding domain of VEGF-165 comprises an amino acid sequence as set forth in any one of SEQ ID NO: 30-34, 40, and 41.

In some embodiments, the anti-VEGF aptamer inhibits an interaction between the VEGF-121 and VEGF-R1. In some embodiments, the anti-VEGF aptamer inhibits an interaction between the VEGF-121 and VEGF-R2. In some embodiments, the anti-VEGF aptamer inhibits an interaction between the VEGF-165 and VEGF-R1. In some embodiments, the anti-VEGF aptamer inhibits an interaction between the VEGF-165 and VEGF-R2.

In some embodiments, the anti-VEGF aptamer is capable of reducing and/or ameliorating a lesion and/or a leakage in a laser-induced choroidal neovascularization (CNV) rat model.

In some embodiments, the anti-VEGF aptamer is capable of reducing and/or ameliorating a lesion and/or a leakage in a non-human primate (NHP) laser-induced CNV model.

In some embodiments, the anti-VEGF aptamer is highly soluble.

In some embodiments, the anti-VEGF aptamer is an RNA aptamer, a DNA aptamer, or a combination thereof. In some embodiments, the anti-VEGF aptamer is nuclease resistant. In some embodiments, the anti-VEGF aptamer comprises one or more modified nucleotide. In some embodiments, all the nucleotides of the anti-VEGF aptamer are modified nucleotides. In some embodiments, the modified nucleotide comprises a chemical substitution or modification at one or more positions independently selected from a ribose position, a deoxyribose position, a phosphate position, and a base position. In some embodiments, the modified nucleotide comprises one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. In some embodiments, the 5-position modified pyrimidine is selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, the anti-VEGF aptamer comprises at least one 2'-modified nucleotide. In some embodiments, all the nucleotides of the anti-VEGF aptamer are 2'-modified nucleotides. In some embodiments, the 2'-modified nucleotide is selected from a 2'-amino-modified nucleotide, a 2'-fluoro-modified nucleotide, and a 2'-O-methyl-modified nucleotide and a 2'-O-(2-methoxyethyl)-modified nucleotide. In some embodiments, the anti-VEGF aptamer comprises at least one 2'-fluoro-modified nucleotide. In some embodiments, the anti-VEGF aptamer comprises at least one 2'-fluoro-modified nucleotide, at least one 2'-O-methyl-modified nucleotide, and/or at least one LNA.

In some embodiments, all the cytidines of the anti-VEGF aptamer are 2'-modified cytidines. In some embodiments, all cytidines of the anti-VEGF aptamer are 2'-fluoro-modified cytidines and/or 2'-O-methyl-modified cytidines. In some embodiments, all the cytidines of the anti-VEGF aptamer are 2'-deoxy-2'-fluorocytidines. In some embodiments, all the uridines of the anti-VEGF aptamer are 2'-modified uridines. In some embodiments, all the uridines of the anti-VEGF aptamer are 2'-fluoro-modified uridines and/or 2'-O-methyl-modified uridines. In some embodiments, all the uridines of the anti-VEGF aptamer are 2'-deoxy-2'-fluorouridines. In some embodiments, all the adenosines of the anti-VEGF aptamer are 2'-modified adenosines. In some embodiments, all the adenosines of the anti-VEGF aptamer are 2'-fluoro-modified adenosines and/or 2'-O-methyl-modified adenosines. In some embodiments, all the adenosines of the anti-VEGF aptamer are 2'-deoxy-2'-fluoroadenosines. In some embodiments, all the guanosines are 2'-modified guanosines. In some embodiments, all the guanosines of the anti-VEGF aptamer are 2'-fluoro-modified guanosines and/or 2'-O-methyl-modified guanosines. In some embodiments, all the guanosines of the anti-VEGF aptamer are 2'-deoxy-2'-fluoroguanosines.

In some embodiments, all the nucleotides of the anti-VEGF aptamer are 2'-fluoro-modified nucleotides and/or 2'-O-methyl-modified nucleotides.

In some embodiments, all the nucleotides of the anti-VEGF aptamer are 2'-fluoro-modified nucleotides.

In some embodiments, the anti-VEGF aptamer does not comprise any natural nucleotide.

In some embodiments, the anti-VEGF aptamer comprises about 10 to about 150 nucleotides.

In some embodiments, the anti-VEGF aptamer competes with an anti-VEGF reference aptamer for binding to the VEGF-165 and/or to the VEGF-121, and the anti-VEGF reference aptamer comprises a secondary structure comprising, from 5' to 3' direction, a first stem, a first loop, a second stem and a second loop.

In some embodiments, the anti-VEGF reference aptamer comprises a secondary structure consisting of, from 5' to 3' direction, a first stem, a first loop, a second stem and a second loop.

In some embodiments, the anti-VEGF reference aptamer comprises a first consensus sequence comprising a nucleotide sequence as set forth in any of SEQ ID NO: 136-137. In some embodiments, the anti-VEGF reference aptamer comprises a second consensus sequence comprising a nucleotide sequence as set forth in any of SEQ ID NO: 138-139.

In some embodiments, the first consensus sequence comprises the nucleotide sequence forming the first stem and the first loop of the anti-VEGF reference aptamer. In some embodiments, the first consensus sequence is not comprised in the nucleotide sequence forming the second stem or the second loop of the anti-VEGF reference aptamer. In some embodiments, the second consensus sequence comprises the nucleotide sequence forming the second stem and the second loop of the anti-VEGF reference aptamer. In some embodiments, the second consensus sequence is not comprised in the nucleotide sequence forming the first stem or the first loop of the anti-VEGF reference aptamer.

In some embodiments, the anti-VEGF reference aptamer comprises a nucleotide sequence as set forth in any of SEQ ID NO: 46-135, SEQ ID NO: 200-201, or a variant or truncate thereof. In some embodiments, the variant comprises a nucleotide sequence that is at least 50% identical to the nucleotide sequence as set forth in any of SEQ ID NO: 46-135, SEQ ID NO: 200-201. In some embodiments, the variant comprises a nucleotide sequence as set forth in any of SEQ ID NO: 46-135, SEQ ID NO: 200-201, with one or more nucleotide addition, deletion, and/or substitution. In some embodiments, the anti-VEGF reference aptamer comprises about 10 to about 150 nucleotides.

In some embodiments, the anti-VEGF reference aptamer comprises the first consensus sequence and the second consensus sequence, and the first consensus sequence is located 5' to the second consensus sequence In some embodiments, the anti-VEGF reference aptamer comprises the first consensus sequence and the second consensus sequence, wherein the second consensus sequence is located 5' to the first consensus sequence.

In some embodiments, the anti-VEGF aptamer comprises a secondary structure comprising, from 5' to 3' direction, a first stem, a first loop, a second stem and a second loop. In some embodiments, the anti-VEGF aptamer comprises a secondary structure consisting of, from 5' to 3' direction, a first stem, a first loop, a second stem and a second loop.

In some embodiments, the anti-VEGF aptamer comprises a first consensus sequence comprising a nucleotide sequence as set forth in any of SEQ ID NO: 136-137. In some embodiments, the anti-VEGF aptamer comprises a second consensus sequence comprising a nucleotide sequence as set forth in any of SEQ ID NO: 138-139.

In some embodiments, the first consensus sequence comprises the nucleotide sequence forming the first stem and the first loop of the anti-VEGF aptamer. In some embodiments, the first consensus sequence is not comprised in the nucleotide sequence forming the second stem or the second loop of the anti-VEGF aptamer. In some embodiments, the second consensus sequence comprises the nucleotide sequence forming the second stem and the second loop of the anti-VEGF aptamer. In some embodiments, the second consensus sequence is not comprised in the nucleotide sequence forming the first stem or the first loop of the anti-VEGF aptamer.

In some embodiments, the anti-VEGF aptamer comprises a nucleotide sequence as set forth in any of SEQ ID NO: 46-135, SEQ ID NO: 200-201, or a variant or truncate thereof. In some embodiments, the variant comprises a nucleotide sequence that is at least 50% identical to the nucleotide sequence as set forth in any of SEQ ID NO: 46-135, SEQ ID NO: 200-201. In some embodiments, the variant comprises a nucleotide sequence as set forth in any of SEQ ID NO: 46-135, SEQ ID NO: 200-201, with one or more nucleotide addition, deletion, and/or substitution.

In some embodiments, the anti-VEGF aptamer comprises the first consensus sequence and the second consensus sequence, and the first consensus sequence is located 5' to the second consensus sequence.

In some embodiments, the anti-VEGF aptamer comprises the first consensus sequence and the second consensus sequence, and the second consensus sequence is located 5' to the consensus sequence.

In some embodiments, the anti-Ang2 aptamer binds to Ang2 with a $K_D$ value of about 100 picomolar (pM) or less.

In some embodiments, the Ang2 is a human Ang2, a mouse Ang2, a monkey Ang2, a rabbit Ang2, and/or a rat Ang2.

In some embodiments, the anti-Ang2 aptamer does not substantially bind to human Ang1.

In some embodiments, the anti-Ang2 aptamer inhibits an interaction between the Ang2 and Tie2.

In some embodiments, the anti-Ang2 aptamer is capable of reducing neovascularization and/or reducing vascular permeability in a mouse oxygen-induced ischemic retinopathy (OIR) model.

In some embodiments, the anti-Ang2 aptamer is highly soluble.

In some embodiments, the anti-Ang2 aptamer is an RNA aptamer, a DNA aptamer, or a combination thereof. In some embodiments, the anti-Ang2 aptamer comprises one or more modified nucleotide. In some embodiments, the anti-Ang2 aptamer is nuclease resistant. In some embodiments, all the nucleotides of the anti-Ang2 aptamer are modified nucleotides. In some embodiments, the modified nucleotide comprises a chemical substitution or modification at one or more positions independently selected from a ribose position, a deoxyribose position, a phosphate position, and a base position. In some embodiments, the modified nucleotide comprises one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. In some embodiments, the 5-position modified pyrimidine is selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

In some embodiments, the anti-Ang2 aptamer comprises at least one 2'-modified nucleotide. In some embodiments, all the nucleotides of the anti-Ang2 aptamer are 2'-modified nucleotides. In some embodiments, the 2'-modified nucleotide is selected from a 2'-amino modified nucleotide, a 2'-fluoro-modified nucleotide, a 2'-O-methyl-modified nucleotide, and a 2'-O-(2-methoxyethyl)-modified nucleotide. In some embodiments, the anti-Ang2 aptamer comprises at least one 2'-fluoro-modified nucleotide, at least one 2'-O-methyl-modified nucleotide, and/or at least one LNA.

In some embodiments, the anti-Ang2 aptamer comprises at least one 2'-fluoro-modified nucleotides. In some embodiments, all the cytidines of the anti-Ang2 aptamer are 2'-modified cytidines. In some embodiments, all the cytidines of the anti-Ang2 aptamer are 2'-fluoro-modified cytidines and/or 2'-O-methyl-modified cytidines. In some embodiments, all the cytidines of the anti-Ang2 aptamer are 2'-deoxy-2'-fluorocytidines. In some embodiments, all the uridines of the anti-Ang2 aptamer are 2'-modified uridines. In some embodiments, all the uridines of the anti-Ang2 aptamer are 2'-fluoro-modified uridines and/or 2'-O-methyl-modified uridines. In some embodiments, all the uridines of the anti-Ang2 aptamer are 2'-deoxy-2'-fluorouridines. In some embodiments, all the adenosines of the anti-Ang2 aptamer are 2'-modified adenosines. In some embodiments, all the adenosines of the anti-Ang2 aptamer are 2'-fluoro-modified adenosines and/or 2'-O-methyl-modified adenosines. In some embodiments, all the adenosines of the anti-Ang2 aptamer are 2'-deoxy-2'-fluoroadenosines. In some embodiments, all the guanosines of the anti-Ang2 aptamer are 2'-modified guanosines. In some embodiments, all the all guanosines of the anti-Ang2 aptamer are 2'-fluoro-modified guanosines and/or 2'-O-methyl-modified guanosines. In some embodiments, all the guanosines of the anti-Ang2 aptamer are 2'-deoxy-2'-fluoroguanosines. In some embodiments, all the nucleotides of the anti-Ang2 aptamer are 2'-fluoro-modified nucleotides. In some embodiments, all the nucleotides of the anti-Ang2 aptamer are 2'-fluoro-modified nucleotides and/or 2'-O-methyl-modified nucleotides.

In some embodiments, the anti-Ang2 aptamer does not comprise any natural nucleotide. In some embodiments, the anti-Ang2 aptamer comprises about 10 to about 150 nucleotides.

In some embodiments, the anti-Ang2 aptamer competes with an anti-Ang2 reference aptamer for binding to the Ang2, wherein the anti-Ang2 reference aptamer comprises a secondary structure comprising, from 5' to 3' direction, a first stem, a first bulge, a second stem, a second bulge, a third stem, a third bulge, a fourth stem, and a first loop.

In some embodiments, the anti-Ang2 reference aptamer comprises a secondary structure consisting of, from 5' to 3' direction, a first stem, a first bulge, a second stem, a second bulge, a third stem, a third bulge, a fourth stem, and a first loop.

In some embodiments, the anti-Ang2 reference aptamer comprises a first consensus sequence comprising a nucleotide sequence as set forth in any of SEQ ID NO: 13-20. In some embodiments, the anti-Ang2 reference aptamer comprises a second consensus sequence comprising a nucleotide sequence as set forth in any of SEQ ID NO: 21-28.

In some embodiments, the first consensus sequence is comprised in the nucleotide sequence forming the first bulge, the second stem, the second bulge, the third stem, the third bulge and/or the fourth stem of the anti-Ang2 reference aptamer. In some embodiments, the first consensus sequence is not comprised in the nucleotide sequence forming first loop of the anti-Ang2 reference aptamer.

In some embodiments, the second consensus sequence is comprised in the nucleotide sequence forming the first bulge, the second stem, the second bulge, the third stem, the third bulge and/or the fourth stem of the anti-Ang2 reference aptamer. In some embodiments, the second consensus sequence is not comprised in the nucleotide sequence forming first loop of the anti-Ang2 reference aptamer.

In some embodiments, the anti-Ang2 reference aptamer comprises a nucleotide sequence as set forth in any of SEQ ID NO: 1-12, or a variant or truncate thereof. In some embodiments, the variant comprises a nucleotide sequence that is at least 50% identical to the nucleotide sequence as set forth in any of SEQ ID NO: 1-12. In some embodiments, the variant comprises a nucleotide sequence as set forth in any of SEQ ID NO: 1-12, with one or more nucleotide addition, deletion, and/or substitution. In some embodiments, the anti-Ang2 reference aptamer comprises about 10 to about 150 nucleotides.

In some embodiments, the anti-Ang2 reference aptamer comprises the first consensus sequence and the second consensus sequence, and the first consensus sequence is located 5' to the second consensus sequence.

In some embodiments, the anti-Ang2 reference aptamer comprises the first consensus sequence and the second consensus sequence, and the second consensus sequence is located 5' to the first consensus sequence.

In some embodiments, the anti-Ang2 aptamer comprises a secondary structure comprising, from 5' to 3' direction, a first stem, a first bulge, a second stem, a second bulge, a third stem, a third bulge, a fourth stem, and a first loop. In some embodiments, the aptamer comprises a secondary structure consisting of, from 5' to 3' direction, a first stem, a first bulge, a second stem, a second bulge, a third stem, a third bulge, a fourth stem, and a first loop.

In some embodiments, the anti-Ang2 aptamer comprises a first consensus sequence comprising a nucleotide sequence as set forth in any of SEQ ID NO: 13-20. In some embodiments, the anti-Ang2 aptamer comprises a second consensus sequence comprising a nucleotide sequence as set forth in any of SEQ ID NO: 21-28.

In some embodiments, the first consensus sequence is comprised in the nucleotide sequence forming the first bulge, the second stem, the second bulge, the third stem, the third bulge and/or the fourth stem of the anti-Ang2 aptamer. In some embodiments, the first consensus sequence is not comprised in the nucleotide sequence forming first loop of the anti-Ang2 aptamer. In some embodiments, the second consensus sequence is comprised in the nucleotide sequence forming the first bulge, the second stem, the second bulge, the third stem, the third bulge and/or the fourth stem of the anti-Ang2 aptamer. In some embodiments, the second consensus sequence is not comprised in the nucleotide sequence forming first loop of the anti-Ang2 aptamer.

In some embodiments, the anti-Ang2 aptamer comprises a nucleotide sequence as set forth in any of SEQ ID NO: 1-12, or a variant or truncate thereof. In some embodiments, the variant comprises a nucleotide sequence that is at least 50% identical to the nucleotide sequence as set forth in any of SEQ ID NO: 1-12. In some embodiments, the variant comprises a nucleotide sequence as set forth in any of SEQ ID NO: 1-12, with one or more nucleotide addition, deletion, and/or substitution.

In some embodiments, the anti-Ang2 aptamer comprises the first consensus sequence and the second consensus sequence, and the first consensus sequence is located 5' to the second consensus sequence.

In some embodiments, the anti-Ang2 aptamer comprises the first consensus sequence and the second consensus sequence, and the second consensus sequence is located 5' to the first consensus sequence.

In some embodiments, the anti-VEGF aptamer is conjugated to a polyethylene glycol (PEG) moiety. In some embodiments, the PEG moiety is conjugated to the 5' terminus of the anti-VEGF aptamer. In some embodiments, the PEG moiety is conjugated to the 3' terminus of the anti-VEGF aptamer. In some embodiments, the anti-Ang2 aptamer is conjugated to a polyethylene glycol (PEG) moiety. In some embodiments, the PEG moiety is conjugated to the 5' terminus of the anti-Ang2 aptamer. In some embodiments, the PEG moiety is conjugated to the 3' terminus of the anti-Ang2 aptamer.

In some embodiments, the bispecific aptamer is of the formula A1-(L)n-A2, wherein A1 is the anti-VEGF aptamer and A2 is the anti-Ang2 aptamer, or A1 is the anti-Ang2 aptamer and A2 is the anti-VEGF aptamer; L is a linker; and n is a number of at least 0. In some embodiments, n is 0 to 20. In some embodiments, n is 0 to 10.

In some embodiments, the bispecific aptamer is capable of specifically binding to both VEGF and Ang2.

In some embodiments, the bispecific aptamer binds to VEGF-121 with a $K_D$ value of about 500 pM or less, and binds to Ang2 with a $K_D$ value of about 500 pM or less.

In some embodiments, the bispecific aptamer binds to VEGF-121 with a $K_D$ value of about 200 pM or less, and binds to Ang2 with a $K_D$ value of about 200 pM or less.

In some embodiments, the bispecific aptamer binds to VEGF-121 with a $K_D$ value of about 100 pM or less, and binds to Ang2 with a $K_D$ value of about 100 pM or less.

In some embodiments of the bispecific aptamer, L is selected from a naturally occurring nucleotide linker, a modified nucleotide linker, a hydrocarbon linker, a polyethylene glycol linker and a combination thereof. In some embodiments, at least one L is a polyethylene glycol linker. In some embodiments, at least one L is a hexaethylene glycol (H or PEG6) linker. In some embodiments, L is a hexaethylene glycol linker, and n is 0 to 10.

In some embodiments of the bispecific aptamer, A1 is an anti-VEGF aptamer comprising a nucleotide sequence as set forth in any of SEQ ID NO: 46-135, SEQ ID NO: 200-201, or a variant or truncate thereof; and A2 is an anti-Ang2 aptamer comprising a nucleotide sequence as set forth in any of SEQ ID NO: 1-12, or a variant or truncate thereof.

In some embodiments of the bispecific aptamer, A1 is an anti-Ang2 aptamer comprising a nucleotide sequence as set forth in any of SEQ ID NO: 1-12, or a variant or truncate thereof; and A2 is an anti-VEGF aptamer comprising a nucleotide sequence as set forth in any of SEQ ID NO: 46-135, SEQ ID NO: 200-201, or a variant or truncate thereof.

In some embodiments of the bispecific aptamer, A1 is an anti-VEGF aptamer comprising a nucleotide sequence as set forth in SEQ ID NO: 83, or a truncate thereof, A2 is an anti-Ang2 aptamer comprising a nucleotide sequence as set forth in SEQ ID NO: 2, or a truncate thereof, L is a hexaethylene glycol linker, and n is 0 to 10.

In some embodiments of the bispecific aptamer, A1 is an anti-VEGF aptamer comprising a nucleotide sequence as set forth in SEQ ID NO: 128, or a truncate thereof, A2 is an anti-Ang2 aptamer comprising a nucleotide sequence as set forth in SEQ ID NO: 6, or a truncate thereof, L is a hexaethylene glycol linker, and n is 0 to 10.

In some embodiments of the bispecific aptamer, A1 is an anti-Ang2 aptamer comprising a nucleotide sequence as set forth in SEQ ID NO: 2, or a truncate thereof, A2 is an anti-VEGF aptamer comprising a nucleotide sequence as set forth in SEQ ID NO: 83, or a truncate thereof, L is a hexaethylene glycol linker, and n is 0 to 10.

In some embodiments of the bispecific aptamer, A1 is an anti-Ang2 aptamer comprising a nucleotide sequence as set forth in SEQ ID NO: 6, or a truncate thereof, A2 is an anti-VEGF aptamer comprising a nucleotide sequence as set forth in SEQ ID NO: 128, or a truncate thereof, L is a hexaethylene glycol linker, and n is 0 to 10.

In some embodiments, the bispecific aptamer is selected from r-AMSB107.0, r-AMSB108.0, r-AMSB107.1, r-AMSB107.2, r-AMSB107, r-AMSB107.4, r-AMSB107.5, r-AMSB107.6, r-AMSB107.7, r-AMSB107.8, r-AMSB107.9, r-AMSB107.10, r-AMSB107.11, r-AMSB107.12, r-AMSB107.13, r-AMSB107.14, r-AMSB107.15, r-AMSB107.16, r-AMSB107.17, r-AMSB107.18, r-AMSB107.19, r-AMSB107.22, r-AMSB107.23, r-AMSB107.24, r-AMSB107.25, r-AMSB107.26, r-AMSB107.27, AMSB107.0, AMSB108.0, AMSB107.1, AMSB107.2, AMSB107, AMSB107.4, AMSB107.5, AMSB107.6, AMSB107.7, AMSB107.8, AMSB107.9, AMSB107.10, AMSB107.11, AMSB107.12, AMSB107.13, AMSB107.14, AMSB107.15, AMSB107.16, AMSB107.17, AMSB107.18, AMSB107.19, AMSB107.20, AMSB107.21, AMSB107.22, AMSB107.23, AMSB107.24, AMSB107.25, AMSB107.26, AMSB107.P6, AMSB107.P40K, AMSB107P and AMSB107.27.

In some embodiments, the bispecific aptamer comprises a nucleotide sequence as set forth in any of SEQ ID NO: 140-195, SEQ ID NO: 202-204.

Composition

In one aspect, the present disclosure provides a composition comprising the anti-Ang2 aptamer of the present disclosure, the anti-VEGF aptamer of the present disclosure, and/or the bispecific aptamer of the present disclosure.

In some embodiments, the composition is a pharmaceutical composition.

In some embodiments, the composition comprises a pharmaceutically acceptable excipient or carrier.

In some embodiments, the composition is for preventing, treating and/or ameliorating a neovascular disease, disorder or condition. The neovascular disease, disorder or condition may be an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

Medical Use and Methods

In another aspect, the present disclosure provides a method for preventing, treating and/or ameliorating a neovascular disease, disorder or condition, comprising administering to a subject in need thereof an effective amount of the anti-Ang2 aptamer of the present disclosure, an effective amount of the anti-VEGF aptamer of the present disclosure, an effective amount of the bispecific aptamer of the present disclosure, and/or an effective amount of the composition of the present disclosure.

In some embodiments, the neovascular disease, disorder or condition is an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

In another aspect, the present disclosure provides use of the anti-Ang2 aptamer of the present disclosure, the anti-VEGF aptamer of the present disclosure, the bispecific aptamer of the present disclosure, and/or the composition of the present disclosure in the manufacture of a medicament for preventing, treating and/or ameliorating a neovascular disease, disorder or condition.

In some embodiments, the neovascular disease, disorder or condition is an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed, and the accompanying drawings (also "figure" and "FIG." herein), of which:

DETAILED DESCRIPTION

Figure 1A:
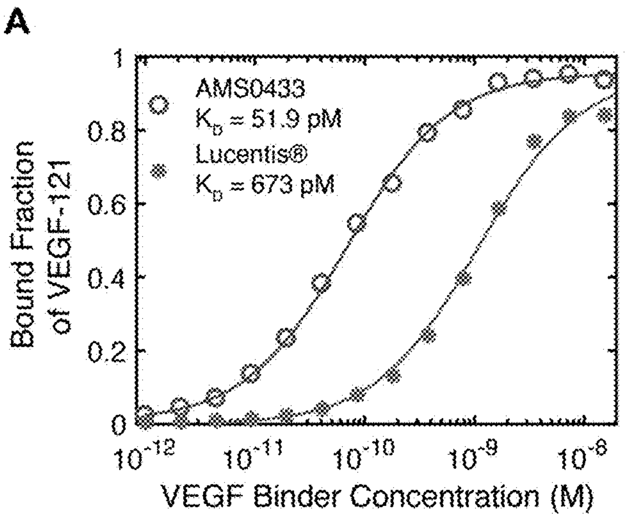
FIGS. 1A-1B illustrate the binding affinity of the anti-VEGF aptamers of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "aptamer", as used herein, generally refers to a non-naturally occurring nucleic acid that has a desirable action on a target molecule. A desirable action may comprise, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In some embodiments, the action may be specific binding affinity for a target molecule, such target molecule being a three-dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that may be identified from a candidate mixture of nucleic acids, where the aptamer may be a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer may bind to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer may include any suitable number of nucleotides. Aptamers may be DNA and/or RNA (or a combination of DNA and RNA) and may be single stranded, double stranded, or contain double stranded or triple stranded regions. In some cases, an aptamer may also comprise one or more (e.g., 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2) non-nucleotide substitutions. For example, one or more nucleotides of the aptamer may be substituted with a polyethylene glycol moiety or a linker comprising multiple (e.g., 1-10, 1-9, 1-8, 1-7, 1-6, 1-5, 1-4, 1-3, or 1-2) polyethylene glycol moieties. In some cases, the linker may be a hexaethylene glycol (H or PEG6) linker. Such substitution may occur to any nucleotide of the aptamer, as long as it does not substantially affect the activity (e.g., binding activity, or inhibition activity) and/or function of the aptamer. In some cases, the substitution does not substantially affect the secondary structure of the aptamer, for example, the substitution may occur to a nucleotide comprised in a bulge or a loop region of the aptamer secondary structure. In some cases, the substitution does not occur to any nucleotide comprised in a stem region of the aptamer secondary structure.

The term "anti-VEGF aptamer", as used herein, generally refers to a nucleic acid molecule having a specific binding affinity for VEGF. In some cases, the anti-VEGF aptamer may comprise one or more (e.g., 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2) non-nucleotide substitutions, as defined herein. For example, one or more nucleotides of the anti-VEGF aptamer may be substituted with a polyethylene glycol moiety or a linker comprising multiple (e.g., 1-10, 1-9, 1-8, 1-7, 1-6, 1-5, 1-4, 1-3, or 1-2) polyethylene glycol moieties. In some cases, the linker may be a hexaethylene glycol (H or PEG6) linker. Such substitution may occur to any nucleotide of the anti-VEGF aptamer, as long as it does not substantially affect the activity (e.g., binding activity, or inhibition activity) and/or function of the anti-VEGF aptamer. In some cases, the substitution does not substantially affect the secondary structure of the anti-VEGF aptamer, for example, the substitution may occur to a nucleotide comprised in a bulge or a loop region of the anti-VEGF aptamer secondary structure. In some cases, the substitution does not occur to any nucleotide comprised in a stem region of the anti-VEGF aptamer secondary structure.

The term "VEGF", as used herein, generally refers to vascular endothelial growth factor A (VEGFA or VEGF-A)

as well as splice variants and isoforms thereof. VEGF can be found as four different splice variants known as VEGF121 (or VEGF-121), VEGF165 (or VEGF-165), VEGF189 (or VEGF-189) and VEGF206 (or VEGF-206; the number refers to the number of amino acids in the polypeptide). All four isoforms exist as disulfide-linked homodimers. The secretion patterns of the isoforms are different in various cell types, although VEGF-165 is the most common isoform observed. The isoforms bind with high affinity to two receptors, Flt-1 and Flk-1/KDR, but they differ in their binding affinity for heparin and extracellular matrix. The number of human VEGF in NCBI database can be NP_001273973.1, NP_001028928.1, NP_001020540.2, NP 001020539.2, NP_001020538.2, NP_003367.4, or NP_001020537.2.

The term "$K_D$ value", as used herein, generally refers to a dissociation constant, measured by a technique appropriate for the aptamer and target pair, for example by using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration Calorimetry (ITC), or MicroscaleThermophoresis (MST). In some embodiments, the $K_D$ value is determined using a standard fluorescence-based ligand binding assay and saturation analysis. In one example, various concentrations of fluorescently labeled target molecules were incubated with a particle of the present disclosure for at least 3 hours at room temperature with gentle rotation. Each sample was then washed, and the remaining bound target was quantified by measuring the fluorescence of each particle using a flow cytometer. The background-subtracted fluorescence values were then fit to a saturation binding curve, e.g. by using an equilibrium binding model (for example, according to the law of mass action).

The term "specific binding" or "specifically binds to" or "specific for" are used interchangeably herein and generally refer to the binding of an agent (e.g., a nucleic acid agent, such as an aptamer) to a target molecule (e.g., a protein or a part thereof), and the binding is measurably and/or statistically different from a non-specific interaction (e.g., a non-specific interaction may be binding to a reference molecule or a random molecule). Specific binding can be measured, for example, by competition with a control molecule that is similar to the target, for example, an excess of non-labeled target, in this case, specific binding is indicated if the binding of the labeled target to a candidate agent is competitively-inhibited by excess unlabeled target. Specific binding may be exhibited, for example, by a molecule having a $K_D$ for the target of at least about 1 nM, at least about 900 pM, at least about 800 pM, at least about 700 pM, at least about 600 pM, at least about 500 pM, at least about 400 pM, at least about 300 pM, at least about 200 pM, at least about 100 pM, at least about 90 pM, at least about 80 pM, at least about 70 pM, at least about 60 pM, at least about 50 pM, at least about 40 pM, at least about 30 pM, at least about 20 pM, at least about 10 pM, at least about 5 pM, at least about 1 pM, or greater.

The term "VEGF receptor-binding domain", as used herein, generally refers to a domain of VEGF that binds to or is recognized by a corresponding VEGF receptor.

The term "VEGF-R" or "VEGF receptor" as used herein, generally refers to receptors that bind VEGF or VEGF family members, including their splice variants and isoforms. VEGFRs may include: (i) Flt-1 (fins-like tyrosine kinase), which is also known as VEGF-R1 (Shibuya et al., Oncogene (1990), 5:519-524; De Vries et al., Science (1992), 255:989-991); (ii) Flk-1 (fetal liver kinase), the mouse RTK (Quinn et al., Proc Natl Acad Sci USA (1993), 90:7533-7537; Millauer et al., Cell (1993), 72:835-846) and its human homolog, KDR (kinase insert domain-containing receptor which is also known as VEGF-R2; Terman et al., Biochem Biophys Res Comm (1992), 187:1579-1586); and (iii) Flt-4, which is expressed on lymphatic endothelium, but not vascular endothelium (Pajusola et al., Cancer Res (1992), 52:5738-43).

The term "RNA aptamer", as used herein, generally refers to an aptamer comprising ribonucleotide units. "RNA aptamer" is also meant to encompass RNA analogs as defined herein.

The term "DNA aptamer", as used herein, generally refers to an aptamer comprising deoxyribonucleotide units. "DNA aptamer" is also meant to encompass DNA analogs as defined herein.

The term "highly soluble", as used herein, generally refers to a feature of an agent that is soluble in a solvent (e.g., water or a proper buffer) with a relatively high degree (e.g. 80% of the whole weight or more, 85% of the whole weight or more, 90% of the whole weight or more, 95% of the whole weight or more, 99% of the whole weight or more).

The term "nuclease resistant", as used herein, generally refers to a feature of an agent that is resistant to nuclease cleavage. In some cases, nucleic acid molecules may be destroyed by exonucleases acting at either the 5' or 3' terminus of the nucleic acid. In addition, endonucleases may cleave the DNA or RNA at internal phosphodiester linkages between individual nucleotides. However, when the molecule (e.g., DNA, or RNA) is nuclease resistant (e.g., after certain modification), the exonuclease or endonuclease may not be able to destroy or digest it anymore.

The term "modified nucleotide", as used herein, generally refers to a nucleotide that does not exist naturally, but is an analog or ester of a naturally occurring nucleotide. When used in the context of an oligonucleotide or a nucleic acid molecule (such as an aptamer), it generally means that at least one of the four constituent nucleotide (i.e., A, G, T/U, and C) of the oligonucleotide is an analog or ester of a naturally occurring nucleotide. In some embodiments, the modified nucleotide may confer nuclease resistance to the oligonucleotide. In some embodiments, the modified nucleotides may lead to predominantly hydrophobic interactions of an aptamer with its protein targets resulting in high binding efficiency and stable co-crystal complexes. A pyrimidine with a substitution at the C-5 position is an example of a modified nucleotide. Modifications may include backbone modifications, methylations, unusual base-pairing combinations such as the isobases isocytidine and isoguanidine, and the like. Modifications may also include 3' and 5' modifications, such as capping. Other modifications may include substitution of one or more of the natural nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those comprising chelators (e.g., metals, radioactive metals, boron, oxidative metals, etc.), those comprising alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support.

The 5' and 3' terminal OH groups can be phosphorylated or substituted with amines, organic capping group moieties of from about 1 to about 20 carbon atoms, polyethylene glycol (PEG) polymers in some embodiments ranging from about 10 to about 80 kDa, PEG polymers in some embodiments ranging from about 20 to about 60 kDa, or other hydrophilic or hydrophobic biological or synthetic polymers. In some embodiments, modifications may be of the C-5 position of pyrimidines. These modifications may be produced through an amide linkage directly at the C-5 position or by other types of linkages.

The term "2'-modified nucleotide", as used herein, generally refers to a nucleotide having a modification of the 2' carbon atom. For example, a cytidine, a uridine, an adenosine, a guanosine may have a modification of the 2' carbon atom.

The term "2'-fluoro-modified nucleotide", as used herein, generally refers to a nucleotide having a 2'-fluoro substituent group. 2'-Deoxy-2'-fluoro modified oligonucleotides may be prepared by methods described in U.S. Pat. No. 6,531,584.

The term "cytidine", as used herein, generally refers to a nucleoside molecule that is formed when cytosine is attached to a ribose ring (also known as a ribofuranose) via a β-N1-glycosidic bond. A cytidine may have the following structure:

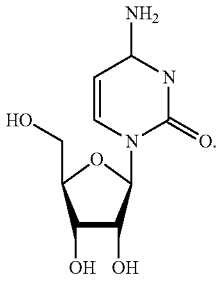

The term "2'-modified cytidine", as used herein, generally refers to a cytidine having a modification of the 2' carbon atom.

The term "2'-deoxy-2'-fluorocytidine", as used herein, generally refers to a chemical having a structure as the following:

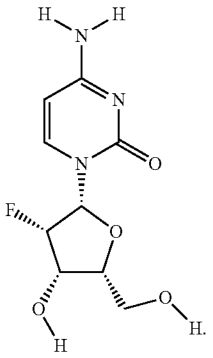

The term "2'-modified uridine", as used herein, generally refers to a uridine having a modification of the 2' carbon atom. Uridine is a glycosylated pyrimidine-analog containing uracil attached to a ribose ring (or more specifically, a ribofuranose) via a β-N1-glycosidic bond. A uridine may have a structure as the following:

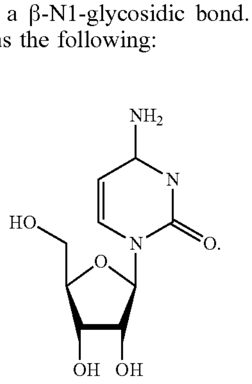

The term "2'-deoxy-2'-fluorouridine", as used herein, generally refers to a chemical having a structure as the following:

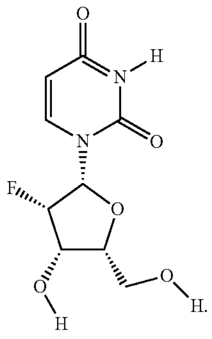

The term "2'-modified adenosine", as used herein, generally refers to an adenosine having a modification of the 2' carbon atom. The adenosine is a purine nucleoside composed of a molecule of adenine attached to a ribose sugar molecule (ribofuranose) moiety via a β-N9-glycosidic bond. An adenosine may have a structure as the following:

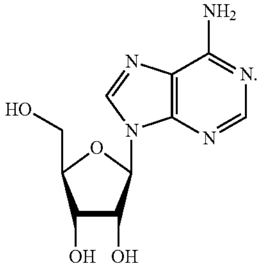

The term "2'-deoxy-2'-fluoroadenosine", as used herein, generally refers to a chemical having a structure as the following:

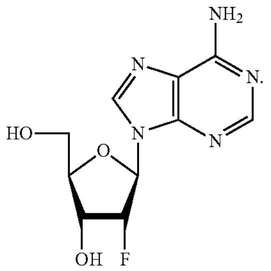

The term "2'-modified guanosine", as used herein, generally refers to a guanosine having a modification of the 2' carbon atom. The guanosine is a purine nucleoside comprising guanine attached to a ribose (ribofuranose) ring via a β-N9-glycosidic bond. A guanosine may have a structure as the following:

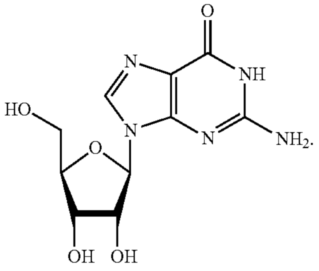

The term "2'-deoxy-2'-fluoroguanosine", as used herein, generally refers to a chemical having a structure as the following:

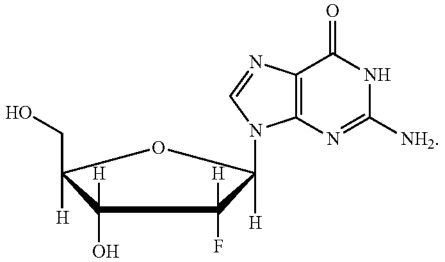

The term "nucleotide", as used herein, generally refers to an organic molecule that serves as the monomer unit for forming the nucleic acid polymer deoxyribonucleic acid (DNA) or ribonucleic acid (RNA). The nucleotide is composed of three subunit molecules: a nitrogenous base, a five-carbon sugar (ribose or deoxyribose), and at least one phosphate group. A nucleoside is composed of a nitrogenous base and a 5-carbon sugar. Thus, a nucleoside with a phosphate group yields a nucleotide.

The term "natural nucleotide", as used herein, generally refers to a nucleotide occurring in nature. For example, the natural nucleotide may comprise cytidine, adenosine, guanosine, uridine. In some embodiments, "natural nucleic acid" also comprises synthesized or modified nucleotides not impeding amplification and/or sequencing.

The term "reference aptamer", as used herein, generally refers to an aptamer which competitively binds to a target as the aptamer of the present disclosure. In some embodiments, the reference aptamer may bind to the same target as that of the aptamer of the present disclosure.

The term "competes", as used herein, generally refers to one chemical substance inhibiting the effect of another by competing with it for binding or bonding. For example, a reference aptamer may competitively bind to the target with the aptamer of the present disclosure. As another example, an aptamer of the present disclosure may competitively bind to the target with a receptor or a ligand of the target.

The term "secondary structure", as used herein, generally refers to a higher-ordered structure of a nucleic acid molecule. The secondary structure may be formed through base pairing interactions within a single nucleic acid polymer or between two polymers. It can be represented as a list of bases which are paired in a nucleic acid molecule. The secondary structure may be generally divided into helices (contiguous base pairs), and various kinds of loops (unpaired nucleotides surrounded by helices). Frequently, these elements, or combinations of them, can be further classified into additional categories comprising stems, bulges, loops, and helix. In the present disclosure, the secondary structure may be determined by using the NUPACK software suite.

The term "5'-3'", as used herein, generally refers to the order from the 5'-end to the 3'-end of a DNA or an RNA strand. The 5'-end may refer to the end of the DNA or RNA strand that has the fifth carbon in the sugar-ring of the deoxyribose or ribose at its terminus. A phosphate group attached to the 5'-end permits ligation of two nucleotides, i.e., the covalent binding of a 5'-phosphate to the 3'-hydroxyl group of another nucleotide, to form a phosphodiester bond. The 3'-end may refer to a termination at the hydroxyl group of the third carbon in the sugar-ring, and is also known as the tail end. The 3'-hydroxyl is often required in the synthesis of new nucleic acid molecules as it is ligated (joined) to the 5'-phosphate of a separate nucleotide, allowing the formation of strands of linked nucleotides.

The term "stem", as used herein, generally refers to a region of a nucleic acid secondary structure, and a stem comprises base-paired helix.

The term "bulge", as used herein, generally refers to a region of a nucleic acid secondary structure in which one strand of a helix has "extra" inserted bases with no counterparts in the opposite strand in the secondary structure of a nucleic acid molecule.

The term "loop", as used herein, generally refers to a region of a nucleic acid secondary structure in which one strand of a helix has one or more bases with no complementary counterpart in the opposite strand in the secondary structure of a nucleic acid molecule.

The term "consensus sequence", as used herein, generally refers to certain positions, not necessarily contiguous, of an oligonucleotide that are specified. By "specified", it is meant that the composition of the position may be other than completely random. Not all oligonucleotides in a mixture may have the same nucleotide at such position; for example, the consensus sequence may comprise a known ratio of particular nucleotides.

The term "truncate", as used herein, generally refers to an aptamer that has been truncated by deletion of nucleotides but still possesses a desired or even improved binding characteristic. Truncates may vary in length in accordance with the length of the starting aptamer and as defined herein for the term "aptamer". Truncations in the truncate may occur in fixed or variable regions, or both fixed and variable regions, of the starting aptamer.

The term "modulating the biological activity", as used herein, generally refers to adjusting (e.g., increasing or decreasing) a biological activity of a target molecule (e.g., a protein, such as a receptor or a ligand). For example, the anti-VEGF aptamer of the present disclosure may modulate the biological activity of a VEGF and/or a VEGF receptor.

The term "neovascular disease or disorder", as used herein, generally refers to a disease or a disorder related to neovascularization. A neovascular disease or disorder may comprise ocular neovascular disease (e.g., retinal and choroidal neovascular diseases), rubeotic glaucoma, pterygia, solid tumor cancers, osteoarthritis, rheumatoid arthritis, vascular anomalies and malformations (e.g., hemangiomas, lymphangiomas, and the like), and psoriasis.

The term "ocular neovascular disease", as used herein, generally refers to a disease characterized by ocular neovascularization, i.e. the development of abnormal blood vessels in the eye of a subject.

The term "VEGF related disease, disorder or condition", as used herein, generally refers to disease, disorder or condition associated with an abnormal activity or loss of activity of VEGF. For example, the VEGF related disease, disorder or condition may comprise aberrant angiogenesis. For example, the VEGF related disease, disorder or condition may comprise cancer, rheumatoid arthritis, the bullous diseases (including bullous pemphigoid, dermatitis herpetiformis, and erythema multiforme), and psoriasis.

The term "age-related macular degeneration", or "AMD", as used herein, generally refers to a macular degeneration which is related to aging. The macular degeneration may affect a central region of the retina known as the macula, and it may lead to a gradual or rapid loss of vision to the level of 20/200 or less. And the AMD may affect central vision, such as for reading and watching television, resulting lost while peripheral vision remains relatively intact.

The term "diabetic retinopathy", or "DR", as used herein, generally refers to a late microvascular complication of diabetes, for example, diabetes Type II. The diabetic retinopathy is a retinal microvascular disease that may be manifested as a cascade of stages with increasing levels of severity and worsening prognoses for vision. DR may be broadly classified into 2 major clinical stages: nonproliferative diabetic retinopathy (NPDR) and proliferative diabetic retinopathy (PDR), where the term "proliferative" refers to the presence of retinal neovascularization.

The term "diabetic macular edema", as used herein, generally refers to a symptom attached at any stage of diabetic retinopathy causing a marked reduction of central visual acuity.

The term "retinal vein occlusion", as used herein, generally refers to a fully or partially occluded retinal vessel that limits the flow of blood through the retinal tissue. The site of the occlusion typically occurs on the venous side and may occur in either the branch vessel (branch retinal vein occlusion-BRVO) or in the central retinal vein (central retinal vein occlusion-CRVO).

The term "myopic choroidal neovascularization", as used herein, generally refers to disease causing visual impairment in persons with pathologic myopia. When vessels are newly generated in the macular area, pigmented fibrous scars, which result in scotoma in the center of vision, are often formed. The myopic choroidal neovascularization belongs to choroidal neovascularization.

The term "anti-VEGF agent", as used herein, generally refers to a compound that inhibits the activity or production of vascular endothelial growth factor ("VEGF").

The term "composition", as used herein, generally refers to a distribution of individual substances that constitute a mixture. The individual substances can be named as components.

The term "pharmaceutical composition", as used herein, generally refers to a formulation prepared in a form suitable for pharmaceutical administration. A pharmaceutical composition may be typically formulated to be compatible with its intended route of administration. Examples of routes of administration may include, but are not limited to, oral and parenteral, e.g., intravenous, intradermal, subcutaneous, inhalation, topical, transdermal, transmucosal, and rectal administration.

The term "pharmaceutically acceptable excipient or carrier", as used herein, generally refers to any excipient or carrier approved by a regulatory agency of a federal or a state government or listed in the U.S. Pharmacopoeia or other generally recognized pharmacopoeia for use in animals and, more particularly, in humans. The term "carrier" may refer to a diluent, adjuvant, excipient, or vehicle with which therapeutic is administered and includes, but is not limited to, such sterile liquids as water and oils.

The term "effective amount", as used herein, generally refers to an amount necessary to ameliorate at least one symptom of a disorder or condition to be prevented, reduced, or treated as described herein. The phrase "therapeutically effective amount" as it relates to an anti-VEGF aptamer, an anti-Ang2 aptamer, or a bispecific aptamer, a composition or an agent of the present disclosure means that the amount of the aptamer shall provide the desired specific pharmacological response after being administered in a significant number of individuals in need of such treatment. It is emphasized that a therapeutically effective amount of an aptamer that is administered to a particular individual in a particular instance will not always be effective in treating the conditions/diseases described herein, even though such dosage is deemed to be a therapeutically effective amount by those of skill in the art.

The term "Ang2", as used herein, generally refers to Angiopoietin-2, which is an angiogenesis factor belonging to the E2F family. Ang2 is thought to be a naturally occurring antagonist for Tie2. Not only human Ang2, but also Ang2 from various species shall be considered to be covered by the term, unless explicitly specified otherwise. The term "Ang2" also encompasses functional fragments and components of the full length Ang2. Human Ang2 is also known as Ensembl:ENSG00000091879, or MIM: 601922.

The term "an interaction between said Ang2 and Tie2", as used herein, generally refers to an activity of an Ang2 binding to a Tie2. Tie2 is an endothelial receptor tyrosine kinase (RTK) that is involved in both embryonic vascular development and pathological angiogenesis.

The term "does not substantially bind", as used herein, generally refers to little or almost no binding to a particular substance. For example, very few or almost no (e.g., less than 10%, less than 9%, less than 8%, less than 7%, less than 6%, less than 5%, less than 4%, less than 3%, less than 2%, less than 1%, less than 0.5%, less than 0.1%, or less than 0.01%) aptamer of the present disclosure may bind to the target thereof.

The term "anti-Ang2 aptamer", as used herein, generally refers to a nucleic acid molecule having a specific binding affinity for Ang2. In some cases, the anti-Ang2 aptamer may comprise one or more (e.g., 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2) non-nucleotide substitutions, as defined herein. For example, one or more nucleotides of the anti-Ang2 aptamer may be substituted with a polyethylene glycol moiety or a linker comprising multiple (e.g., 1-10, 1-9, 1-8, 1-7, 1-6, 1-5, 1-4, 1-3, or 1-2) polyethylene glycol moieties. In some cases, the linker may be a hexaethylene glycol (H or PEG6) linker. Such substitution may occur to any nucleotide of the anti-VEGF aptamer, as long as it does not substantially affect the activity (e.g., binding activity, or inhibition activity) and/or function of the anti-Ang2 aptamer. In some cases, the substitution does not substantially affect the secondary structure of the anti-Ang2 aptamer, for example, the substitution may occur to a nucleotide comprised in a bulge or a loop region of the anti-Ang2 aptamer secondary structure. In some cases, the substitution does not occur to any nucleotide comprised in a stem region of the anti-Ang2 aptamer secondary structure.

The term "anti-Ang2 agent", as used herein, generally refers to an agent that inhibits the activity or production of Ang2.

The term "Aflibercept", as used herein, generally refers to a recombinant fusion protein consisting of vascular endothelial growth factor (VEGF)-binding portions from the extracellular domains of human VEGF receptors 1 and 2, that are fused to the Fc portion of the human IgG1 immunoglobulin.

The term "linker", as used herein, generally refers to an agent which is designed to facilitate the functional connection of two parts in to a linked one. For example, the linker may be used to make a single chain to achieve the desired biological activity. For example, the linker may be used to make a single chain to confer a degree of stability required for the resulted linked nucleotides.

The term "nucleotide linker", as used herein, generally refers to a linker made of nucleotides. The nucleotide linker that connects adjacent nucleotides can vary in length.

The term "modified nucleotide linker", as used herein, generally refers to a nucleotide linker with one or more modifications.

The term "hydrocarbon linker", as used herein, generally refers to a linker made of hydrocarbon. The hydrocarbon is an organic compound consisting entirely of hydrogen and carbon. Examples of hydrocarbons include but are not limited to, e.g., methane, ethane, propane, butane, pentane, hexane, heptane, octane, nonane, decane, undecane, and dodecane.

The term "polyethylene glycol linker", as used herein, generally refers to a linker made of one or more polyethylene glycol (PEG) subunits.

The term "a fragment thereof", as used herein, generally refers to a partial region obtainable from an intact parent molecule (e.g., an aptamer of the present disclosure). The fragment may still retain the properties of the parent molecule that it is derived from. In some case, the fragments may offer a number of advantages over the intact parent molecule for manufacturing and/or medical use.

The term "variant", as used herein, generally refers to an aptamer molecule that differs from a parent molecule (e.g., an aptamer) by at least one nucleotide acid. A variant may refer to the molecule itself, a composition comprising the molecule. It may also refer to the nucleotide acid sequence of the molecule, when such a molecule is a DNA or RNA. In some cases, a variant differs from its parent molecule (e.g., an aptamer) by an addition, deletion or substitution of one or more nucleotide acid, such as 1-50, 1-40, 1-30, 1-20, 1-15, 1-14, 1-13, 1-12, 1-11, 1-10, 1-9, 1-8, 1-7, 1-6, 1-5, 1-4, 1-3, or 1-2 nucleotide acid. In some cases, the variant may possess at least about 80% (e.g., at least 85%, at least 90%, at least 91%, at least 92%, at least 93%, at least 94%, at least 95%, at least 96%, at least 97%, at least 98%, at least 99% or higher) sequence homology/identity with the nucleotide acid sequence of its parent molecule.

The term "reducing neovascularization", as used herein, generally refers to that the degree of neovascularization is reduced. Neovascularization is the natural formation of new blood vessels, usually in the form of functional microvascular networks, may be capable of perfusion by red blood cells, that form to serve as collateral circulation in response to local poor perfusion or ischemia. In the present disclosure, it may be interchangeably used with "angiogenesis".

The term "reducing vascular permeability", as used herein, generally refers to that the degree of vascular permeability in a tissue is reduced. Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). And disease states associated with angiogenesis and/or increased vascular permeability may be cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

The term "mouse oxygen-induced ischemic retinopathy (OIR) model", as used herein, generally refers to an animal model developing oxygen-induced retinopathy in the mouse with reproducible and quantifiable proliferative retinal neovascularization. The model may be suitable for examining pathogenesis and therapeutic intervention for retinal neovascularization in retinopathy of prematurity (ROP) and other vascular pathologies. The preparation method of the model is described in, e.g., Smith L E, et al. Oxygen-induced retinopathy in the mouse. Invest. Opthalmol. Vis. Sci. 1994; 35:101-111.

The term "Ang2 related disease, disorder or condition", as used herein, generally refers to a disease, disorder or condition that is associated with an abnormal activity or loss of activity of Ang2. For example, the Ang2 related disease, disorder or condition may have effects on angiogenesis. Examples for such disease, disorder or condition may be cancer or cancerous diseases, eye diseases such as age-related macular degeneration and diabetic retinopathy, and/or chronic kidney diseases such as diabetic nephropathy, postrenal failure, prerenal azotemia and intrinsic renal failure.

As used herein, the singular forms "a", "and", and "the" include plural referents unless the context clearly dictates otherwise. Thus, for example, reference to "a particle" includes a plurality of such particles and reference to "the sequence" includes reference to one or more said sequences and equivalents thereof known to those skilled in the art, and so forth.

The term "about", as used herein, generally refers to an approximation to a given value that would reasonably be inferred based on the ordinary skill in the art, including equivalents and approximations due to the experimental and/or measurement conditions for such given value. For example, it may refer to a value that is no more than 10% above or below the value being modified by the term.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

Anti-VEGF Aptamer

In one aspect, the present disclosure provides an anti-VEGF aptamer, which binds to VEGF-121 with a $K_D$ value of about 20 nanomolar (nM) or less, and binds to VEGF-165 with a $K_D$ value of about 20 nanomolar (nM) or less.

For example, the anti-VEGF aptamer may bind to VEGF-121 with a $K_D$ value of about 20 nanomolar (nM) or less, 18 nanomolar (nM) or less, 16 nanomolar (nM) or less, 14 nanomolar (nM) or less, 12 nanomolar (nM) or less, 10 nanomolar (nM) or less, 8 nanomolar (nM) or less, 6 nanomolar (nM) or less, 4 nanomolar (nM) or less, 2 nanomolar (nM) or less, 1 nanomolar (nM) or less, 0.5 nanomolar (nM) or less, 0.4 nanomolar (nM) or less, 0.2 nanomolar (nM) or less, 0.1 nanomolar (nM) or less, 0.09 nanomolar (nM) or less, 0.08 nanomolar (nM) or less, 0.07 nanomolar (nM) or less, 0.06 nanomolar (nM) or less, 0.05 nanomolar (nM) or less, 0.04 nanomolar (nM) or less, or 0.03 nanomolar (nM) or less.

For example, the anti-VEGF aptamer may bind to VEGF-165 with a $K_D$ value of about 20 nanomolar (nM) or less, 18 nanomolar (nM) or less, 16 nanomolar (nM) or less, 14 nanomolar (nM) or less, 12 nanomolar (nM) or less, 10 nanomolar (nM) or less, 8 nanomolar (nM) or less, 6 nanomolar (nM) or less, 4 nanomolar (nM) or less, 2 nanomolar (nM) or less, 1 nanomolar (nM) or less, 0.5 nanomolar (nM) or less, 0.4 nanomolar (nM) or less, 0.2 nanomolar (nM) or less, 0.18 nanomolar (nM) or less, 0.15 nanomolar (nM) or less, 0.12 nanomolar (nM) or less, 0.1 nanomolar (nM) or less, 0.09 nanomolar (nM) or less, 0.08 nanomolar (nM) or less, 0.07 nanomolar (nM) or less, 0.06 nanomolar (nM) or less, 0.05 nanomolar (nM) or less, 0.04 nanomolar (nM) or less, or 0.03 nanomolar (nM) or less.

The VEGF-121 may be a human VEGF-121, a mouse VEGF-120, a monkey VEGF-121, a rabbit VEGF-121, and/or a rat VEGF-120. The VEGF-165 may be a human VEGF-165, a mouse VEGF-164, a monkey VEGF-165, a rabbit VEGF-165, and/or a rat VEGF-164.

The human VEGF-121 (NCBI No. P15692-9) may comprise an amino acid sequence as set forth in SEQ ID NO: 29. The mouse VEGF-120 (NCBI No. Q00731-3) may comprise an amino acid sequence as set forth in SEQ ID NO: 44. The rat VEGF-120 (NCBI No. P16612-4) may comprise an amino acid sequence as set forth in SEQ ID NO: 42.

The human VEGF-165 (NCBI No. P15692-4) may comprise an amino acid sequence as set forth in SEQ ID NO: 35. The mouse VEGF-164 (NCBI No. Q00731-2) may comprise an amino acid sequence as set forth in SEQ ID NO: 43. The monkey VEGF-165 (NCBI No. H9EQI6) may comprise an amino acid sequence as set forth in SEQ ID NO: 35. The rat VEGF-164 (NCBI No. P16612-2) may comprise an amino acid sequence as set forth in SEQ ID NO: 39.

The rabbit VEGF-189 (NCBI No. G1T1L9) may comprise an amino acid sequence as set forth in SEQ ID NO: 36.

The anti-VEGF aptamer may specifically bind to both 1) a VEGF receptor-binding domain of VEGF-121 or a fragment thereof; and 2) a VEGF receptor-binding domain of VEGF-165 or a fragment thereof.

The VEGF receptor-binding domain of VEGF-121 may comprise an amino acid sequence as set forth in any one of SEQ ID NO: 30-34, 40, 41, and 45. The VEGF receptor-binding domain of VEGF-165 may comprise an amino acid sequence as set forth in any one of SEQ ID NO: 30-34, 40, and 41.

The receptor binding domain 1 of human VEGF-121 may comprise an amino acid sequence as set forth in SEQ ID NO: 30. The receptor binding domain 2 of human VEGF-121 may comprise an amino acid sequence as set forth in SEQ ID NO: 31. The receptor binding domain 3 of human VEGF-121 may comprise an amino acid sequence as set forth in SEQ ID NO: 32. The receptor binding domain 4 of human VEGF-121 may comprise an amino acid sequence as set forth in SEQ ID NO: 33. The receptor binding domain 5 of human VEGF-121 may comprise an amino acid sequence as set forth in SEQ ID NO: 34.

The receptor binding domain 1 of human VEGF-165 may comprise an amino acid sequence as set forth in SEQ ID NO: 30. The receptor binding domain 2 of human VEGF-165 may comprise an amino acid sequence as set forth in SEQ ID NO: 31. The receptor binding domain 3 of human VEGF-165 may comprise an amino acid sequence as set forth in SEQ ID NO: 32. The receptor binding domain 4 of human VEGF-165 may comprise an amino acid sequence as set forth in SEQ ID NO: 33. The receptor binding domain 5 of human VEGF-165 may comprise an amino acid sequence as set forth in SEQ ID NO: 34.

The receptor binding domain 1 of Monkey VEGF-165 may comprise an amino acid sequence as set forth in SEQ ID NO:30. The receptor binding domain 2 of Monkey VEGF-165 may comprise an amino acid sequence as set forth in SEQ ID NO:31. The receptor binding domain 3 of Monkey VEGF-165 may comprise an amino acid sequence as set forth in SEQ ID NO: 32. The receptor binding domain 4 of Monkey VEGF-165 may comprise an amino acid sequence as set forth in SEQ ID NO: 33. The receptor binding domain 5 of Monkey VEGF-165 may comprise an amino acid sequence as set forth in SEQ ID NO: 34.

The receptor binding domain 1 of rabbit VEGF-189 may comprise an amino acid sequence as set forth in SEQ ID NO:37. The receptor binding domain 2 of rabbit VEGF-189 may comprise an amino acid sequence as set forth in SEQ ID NO: 31. The receptor binding domain 3 of rabbit VEGF-189 may comprise an amino acid sequence as set forth in SEQ ID NO: 38. The receptor binding domain 4 of rabbit VEGF-189 may comprise an amino acid sequence as set forth in SEQ ID NO: 33. The receptor binding domain 5 of rabbit VEGF-189 may comprise an amino acid sequence as set forth in SEQ ID NO: 34.

The receptor binding domain 1 of rat VEGF-164 may comprise an amino acid sequence as set forth in SEQ ID NO: 30. The receptor binding domain 2 of rat VEGF-164 may comprise an amino acid sequence as set forth in SEQ ID NO: 31. The receptor binding domain 3 of rat VEGF-164 may comprise an amino acid sequence as set forth in SEQ ID NO: 40. The receptor binding domain 4 of rat VEGF-164 may comprise an amino acid sequence as set forth in SEQ ID NO: 33. The receptor binding domain 5 of rat VEGF-164 may comprise an amino acid sequence as set forth in SEQ ID NO:41.

The receptor binding domain 1 of rat VEGF-120 may comprise an amino acid sequence as set forth in SEQ ID NO: 30. The receptor binding domain 2 of rat VEGF-120 may comprise an amino acid sequence as set forth in SEQ ID NO: 31. The receptor binding domain 3 of rat VEGF-120 may comprise an amino acid sequence as set forth in SEQ ID NO: 40. The receptor binding domain 4 of rat VEGF-120 may comprise an amino acid sequence as set forth in SEQ ID NO: 33. The receptor binding domain 5 of rat VEGF-120 may comprise an amino acid sequence as set forth in SEQ ID NO: 41.

The receptor binding domain 1 of mouse VEGF-164 may comprise an amino acid sequence as set forth in SEQ ID NO: 30. The receptor binding domain 2 of mouse VEGF-164 may comprise an amino acid sequence as set forth in SEQ ID NO: 31. The receptor binding domain 3 of mouse VEGF-164 may comprise an amino acid sequence as set forth in SEQ ID NO: 40. The receptor binding domain 4 of mouse VEGF-164 may comprise an amino acid sequence as set forth in SEQ ID NO:33. The receptor binding domain 5 of mouse VEGF-164 may comprise an amino acid sequence as set forth in SEQ ID NO: 41.

The receptor binding domain 1 of mouse VEGF-120 may comprise an amino acid sequence as set forth in SEQ ID NO:30. The receptor binding domain 2 of mouse VEGF-120 may comprise an amino acid sequence as set forth in SEQ ID NO: 31. The receptor binding domain 3 of mouse VEGF-120 may comprise an amino acid sequence as set forth in SEQ ID NO: 40. The receptor binding domain 4 of mouse VEGF-120 may comprise an amino acid sequence as set forth in SEQ ID NO: 45. The receptor binding domain 5 of mouse VEGF-120 may comprise an amino acid sequence as set forth in SEQ ID NO: 41.

The anti-VEGF aptamer may inhibit an interaction between the VEGF-121 and VEGF-R1. The anti-VEGF aptamer may inhibit an interaction between the VEGF-121 and VEGF-R2. The anti-VEGF aptamer may inhibit an interaction between the VEGF-165 and VEGF-R1. The anti-VEGF aptamer may also or in addition inhibit an interaction between the VEGF-165 and VEGF-R2.

The anti-VEGF aptamer of the present disclosure may be capable of reducing and/or ameliorating neovascularization and/or leakage in an animal model, such as an ocular animal model.

The animal model may be a vertebrate animal model, in some cases, the animal model may be a mammal model. The animal may be a rat, a mouse, a rabbit, a goat, a sheep, a non-human primate, or any other suitable animal.

In some embodiments, the anti-VEGF aptamer of the present disclosure may be capable of reducing and/or ameliorating a lesion and/or a leakage in a laser-induced choroidal neovascularization (CNV) model (such as a rat model or a non-human primate (NHP) model).

The anti-VEGF aptamer of the present disclosure may be highly soluble. For example, the anti-VEGF aptamer may be dissolved in the solvent with a relatively high degree (e.g. 80% of the whole weight or more, 85% of the whole weight or more, 90% of the whole weight or more, 95% of the whole weight or more, 99% of the whole weight or more). For example, the anti-VEGF aptamer may be formulated at a concentration of 100 mg/ml or more, or at a concentration of 150 mg/ml or more, such as at a concentration of 200 mg/ml or more.

The anti-VEGF aptamer may be an RNA aptamer, a DNA aptamer, or a combination thereof. For example, the anti-VEGF aptamer may comprise primarily RNA, it may comprise primarily DNA, or it may comprise both RNA and DNA.

The anti-VEGF aptamer may comprise one or more (e.g. 1, 2, 3, 4, 5, 6, 7, 8, 9, 10, 11, 12, 13, 14, 15 or more) modified nucleotide. In some cases, all of the nucleotides of the anti-VEGF aptamer may be modified nucleotides. For instance, the anti-VEGF aptamer may have 20 nucleotides, and all of these 20 nucleotides may be modified nucleotide.

In some cases, the anti-VEGF aptamer of the present disclosure may be nuclease resistant.

The modified nucleotide may comprise a chemical substitution or modification at one or more positions independently selected from a ribose position, a deoxyribose position, a phosphate position, and a base position. The modified nucleotide may comprise one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. The 5-position modified pyrimidine is selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

The anti-VEGF aptamer may comprise at least one (e.g. 1, 2, 3, 4, 5, 6, 7, 8, 9, 10, 11, 12, 13, 14, 15 or more) 2'-modified nucleotide. In some embodiments, all the nucleotides may be 2'-modified nucleotides. The 2'-modified nucleotide may be selected from a 2'-amino modified nucleotide, a 2'-fluoro-modified nucleotide, a 2'-O-methyl-modified nucleotide, and a 2'-O-(2-methoxyethyl)-modified nucleotide.

In some cases, all the cytidines may be 2'-modified cytidines. In some cases, all the cytidines may be 2'-fluoro-modified cytidines and/or 2'-O-methyl-modified cytidines. In some cases, all the cytidines may be 2'-deoxy-2'-fluoro-cytidines. In some cases, all the uridines may be 2'-modified uridines. In some cases, all the uridines may be 2'-fluoro-modified uridines and/or 2'-O-methyl-modified uridines. In some cases, all the uridines may be 2'-deoxy-2'-fluorouridines. In some cases, all the adenosines may be 2'-modified adenosines. In some cases, all the adenosines may be 2'-fluoro-modified adenosines and/or 2'-O-methyl-modified adenosines. In some cases, all the adenosines may be 2'-deoxy-2'-fluoroadenosines. In some cases, all the guanosines may be 2'-modified guanosines. In some cases, all the guanosines may be 2'-fluoro-modified guanosines and/or 2'-O-methyl-modified guanosines. In some cases, all the guanosines may be 2'-deoxy-2'-fluoroguanosines.

For example, the anti-VEGF aptamer comprising the at least one 2'-modified nucleotide. In some embodiments, all the nucleotides of the anti-VEGF aptamer may be 2'-modified nucleotides. In some embodiments, all the nucleotides of the anti-VEGF aptamer may be 2'-fluoro-modified nucleotides and/or 2'-O-methyl-modified nucleotides. For example, the 2'-fluoro-modified nucleotides may be 2'-fluoro (2'-F)-modified nucleotides or 2'-fluoro-2'-deoxy-modified nucleotides. For example, the 2'-fluoro-modified nucleotides may comprise the following structure:

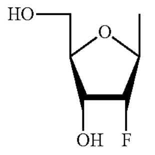

.

In some cases, the anti-VEGF aptamer does not comprise any natural nucleotide (e.g., unmodified A, C, T, U or G).

The anti-VEGF aptamer may comprise about 10 to about 150 nucleotides. For example, the anti-VEGF aptamer may comprise about 10 to about 150 nucleotides, about 10 to about 140 nucleotides, about 10 to about 130 nucleotides, about 10 to about 120 nucleotides, about 10 to about 110 nucleotides, about 10 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, about 10 to about 20 nucleotides.

The anti-VEGF aptamer may compete with an anti-VEGF reference aptamer for binding to the VEGF-165 and/or to the VEGF-121.

The anti-VEGF reference aptamer or the anti-VEGF aptamer of the present disclosure may comprise a nucleotide sequence with or without modifications. For example, the aptamer may comprise natural and/or modified nucleotides. When an aptamer is defined as comprising or consisting of a nucleotide sequence as set forth in a particular SEQ ID NO, the nucleotides within the sequence may be further modified.

According to the present disclosure, the anti-VEGF aptamer r-AMS0431.0 has natural nucleotides, and its nucleotide sequence is as set forth in SEQ ID NO: 46; the anti-VEGF aptamer AMS0431.0 has the corresponding 2'-fluoro-modified nucleotides, and its nucleotide sequence is as set forth in SEQ ID NO: 91. Thus, an aptamer comprising a nucleotide sequence as set forth in SEQ ID NO: 46 may encompass both r-AMS0431.0 and AMS0431.0, but an aptamer comprising a nucleotide sequence as set forth in SEQ ID NO: 91 may not encompass r-AMS0431.0.

Similarly, in the present disclosure, generally, aptamers (e.g. an aptamer of the present disclosure) named with "r-AMSxxxx" (e.g., r-AMS0433) has natural nucleotides (but could comprise linkers, e.g, the H linker as described herein), and the aptamer comprising corresponding 2'-fluoro-modified nucleotides are named as "AMSxxxx" (e.g., AMS0433).

The anti-VEGF reference aptamer or the anti-VEGF aptamer of the present disclosure may comprise a secondary structure comprising (e.g., from 5' to 3' direction), a first stem, a first loop, a second stem and a second loop. The anti-VEGF aptamer may comprise a secondary structure consisting of (e.g., from 5' to 3' direction), a first stem, a first loop, a second stem and a second loop.

The anti-VEGF reference aptamer or the anti-VEGF aptamer of the present disclosure may comprise a first consensus sequence comprising a nucleotide sequence as set forth in any of SEQ ID NO: 136-137.

Alternatively, or in addition, the anti-VEGF reference aptamer or the anti-VEGF aptamer of the present disclosure may comprise a second consensus sequence comprising a nucleotide sequence as set forth in any of SEQ ID NO: 138-139.

For example, the anti-VEGF reference aptamer or the anti-VEGF aptamer of the present disclosure may comprise a first consensus sequence comprising a nucleotide sequence as set forth is as set forth in SEQ ID NO: 136, as well as a second consensus sequence comprising a nucleotide sequence as set forth is as set forth in SEQ ID NO: 138; the anti-VEGF reference aptamer or the anti-VEGF aptamer of the present disclosure may comprise a first consensus sequence comprising a nucleotide sequence as set forth is as set forth in SEQ ID NO: 137, as well as a second consensus sequence comprising a nucleotide sequence as set forth is as set forth in SEQ ID NO: 139.

The first consensus sequence may comprise the nucleotide sequence forming the first stem and the first loop of the anti-VEGF reference aptamer or the anti-VEGF aptamer of the present disclosure. In some cases, the first consensus sequence may not be comprised in the nucleotide sequence forming the second stem or the second loop of the anti-VEGF reference aptamer or the anti-VEGF aptamer of the present disclosure.

The second consensus sequence may comprise the nucleotide sequence forming the second stem and the second loop of the anti-VEGF reference aptamer or the anti-VEGF aptamer of the present disclosure. In some cases, the second consensus sequence may not be comprised in the nucleotide sequence forming the first stem or the first loop of the anti-VEGF reference aptamer or the anti-VEGF aptamer of the present disclosure.

The anti-VEGF reference aptamer or the anti-VEGF aptamer of the present disclosure may comprise the first consensus sequence and the second consensus sequence, wherein the first consensus sequence may be located 5' to the second consensus sequence.

In some cases, the anti-VEGF reference aptamer or the anti-VEGF aptamer of the present disclosure may comprise the first consensus sequence and the second consensus sequence, wherein the second consensus sequence may be located 5' to the first consensus sequence.

The anti-VEGF reference aptamer or the anti-VEGF aptamer of the present disclosure may comprise a nucleotide sequence as set forth in any of SEQ ID NO: 46-135, SEQ ID NO: 200-201, or a variant or truncate thereof. The variant may comprise a nucleotide sequence that is at least 50% identical to the nucleotide sequence as set forth in any of SEQ ID NO: 46-135, SEQ ID NO: 200-201. The variant may comprise a nucleotide sequence as set forth in any of SEQ ID NO: 46-135, SEQ ID NO: 200-201, with one or more (e.g., 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, or more) nucleotide addition, deletion, and/or substitution.

The anti-VEGF reference aptamer may comprise about 10 to about 150 nucleotides. For example, the anti-VEGF reference aptamer may comprise about 10 to about 150 nucleotides, about 10 to about 140 nucleotides, about 10 to about 130 nucleotides, about 10 to about 120 nucleotides, about 10 to about 110 nucleotides, about 10 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, or about 10 to about 30 nucleotides, about 10 to about 20 nucleotides.

The anti-VEGF aptamer may be used for modulating the biological activity of a VEGF or a VEGF receptor.

The anti-VEGF aptamer may be used for preventing, treating, and/or ameliorating a VEGF related disease, disorder or condition. For example, the VEGF related disease, disorder or condition may be a neovascular disease, disorder or condition. For example, the VEGF related disease, disorder or condition may be an ocular neovascular disease, disorder or condition. For example, the VEGF related disease, disorder or condition may be selected from age-related macular degeneration, choroidal neovascularization, diabetic macular edema, retinal vein occlusion, and diabetic retinopathy. For example, the VEGF related disease, disorder or condition may be selected from wet age-related macular degeneration, myopic choroidal neovascularization, and proliferative diabetic retinopathy.

In one aspect, the present disclosure provides an anti-VEGF agent, comprising the aptamer of the present disclosure. The anti-VEGF agent may further comprise a polyethylene glycol (PEG) moiety. For example, the PEG moiety may be conjugated to the 5' terminus and/or the 3' terminus of the anti-VEGF aptamer.

In another aspect, the present disclosure provides a composition comprising the anti-VEGF aptamer, and/or the anti-VEGF agent of the present application.

In some cases, the composition may be a pharmaceutical composition. For example, the composition may comprise a pharmaceutically acceptable excipient or carrier.

In some cases, the composition may be presented as discrete dosage forms, with each dosage containing a predetermined amount of an active ingredient as a powder or in granules, a solution, or a suspension in an aqueous or non-aqueous liquid. Such dosage forms can be prepared by any of the methods known to a skilled person, for example, it may include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The composition may comprise a therapeutically effective amount of the active composition (e.g., the anti-VEGF aptamer or the anti-VEGF agent of the present disclosure). A therapeutically effective amount may be an amount of the subject composition capable of preventing and/or curing (at least partially) a neovascular disease or disorder and/or any complications thereof in a subject suffering from or having a risk of developing the condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

The composition may further comprise an effective amount of an additional therapeutically active component, for example, an additional therapeutically active component for preventing, treating and/or ameliorating a neovascular disease or disorder. Each of the active components may be present in the pharmaceutical composition in a pharmaceutically effective amount. The anti-VEGF aptamer of the present application may or may not be associated with the additional active component.

Described below are non-limiting exemplary compositions and methods for preparing such a composition. The composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The composition may be in unit dosage forms suitable for single administration of precise dosages. In some embodiments, the composition may be a liquid pharmaceutical composition.

In the composition, the anti-VEGF aptamer may be combined in an intimate admixture with a pharmaceutical carrier according to conventional pharmaceutical compounding techniques. The carrier may take a wide variety of forms depending on the form of preparation desired for administration.

The composition may further include one or more pharmaceutically acceptable additives and excipients. Such additives and excipients include, without limitation, detackifiers, anti-foaming compositions, buffering compositions, polymers, antioxidants, preservatives, chelating compositions, viscomodulators, tonicifiers, flavorants, colorants, odorants, opacifiers, suspending compositions, binders, fillers, plasticizers, lubricants, and/or mixtures thereof.

In another aspect, the present disclosure provides a method for modulating the biological activity of a VEGF or a VEGF receptor, comprising administering to a subject in need thereof an effective amount of the anti-VEGF aptamer or the anti-VEGF agent of the present disclosure.

In another aspect, the present disclosure provides a method for preventing, treating, and/or ameliorating a VEGF related disease, disorder or condition, comprising administering to a subject in need thereof an effective amount of the anti-VEGF aptamer, or the anti-VEGF agent of the present disclosure.

For example, the VEGF related disease, disorder or condition may be a neovascular disease, disorder or condition. For example, the VEGF related disease, disorder or condition may be an ocular neovascular disease, disorder or condition. For example, the VEGF related disease, disorder or condition may be selected from age-related macular degeneration, choroidal neovascularization, diabetic macular edema, retinal vein occlusion, and diabetic retinopathy. For example, the VEGF related disease, disorder or condition may be selected from wet age-related macular degeneration, myopic choroidal neovascularization, and proliferative diabetic retinopathy.

In one aspect, the present disclosure provides a use of the anti-VEGF aptamer, or the anti-VEGF agent of the present disclosure in the manufacture of an agent for modulating the biological activity of a VEGF or a VEGF receptor.

In one aspect, the present disclosure provides a use of the aptamer of the present disclosure, or the anti-VEGF agent of the present disclosure, in the manufacture of a medicament for preventing, treating, and/or ameliorating a VEGF related disease, disorder or condition.

The VEGF related disease, disorder or condition may be a neovascular disease, disorder or condition. For example, the VEGF related disease, disorder or condition may be an ocular neovascular disease, disorder or condition. For example, the VEGF related disease, disorder or condition may be selected from age-related macular degeneration, choroidal neovascularization, diabetic macular edema, retinal vein occlusion, and diabetic retinopathy. For example, the VEGF related disease, disorder or condition may be selected from wet age-related macular degeneration, myopic choroidal neovascularization, and proliferative diabetic retinopathy.

Anti-Ang2 Aptamer

In one aspect, the present disclosure provides an aptamer that specifically binds to Ang2 with a $K_D$ value of about 500 picomolar (pM) or less. For example, the anti-Ang2 aptamer may bind to Ang2 with a $K_D$ value of about 500 picomolar (pM) or less, about 400 picomolar (pM) or less, about 300 picomolar (pM) or less, about 200 picomolar (pM) or less, about 100 picomolar (pM) or less, about 90 picomolar (pM) or less, about 80 picomolar (pM) or less, about 70 picomolar (pM) or less, about 60 picomolar (pM) or less, about 50 picomolar (pM) or less, about 40 picomolar (pM) or less, about 30 picomolar (pM) or less, or about 20 picomolar (pM) or less.

The Ang2 may be a human Ang2, a mouse Ang2, a monkey Ang2, a rabbit Ang2, and/or a rat Ang2.

The anti-Ang2 aptamer may not substantially bind to human Ang1. For example, the anti-Ang2 aptamer may bind to Ang1 with an affinity that is significantly lower (e.g. at least 1-fold lower, at least 2 folds lower, at least 3 folds lower, at least 4 or more folds lower) than its affinity for Ang2. In some cases, the anti-Ang2 aptamer may bind to Ang1 with a $K_D$ value that is not measurable using Ligand Binding Assays with radioactive or fluorescent measurement, Surface Plasmon Resonance (SPR), Bio-Layer Interferometry (BLI, e.g., the Octet® Systems), SRU biosystems BIND®, Isothermal Titration Calorimetry (ITC), or MicroscaleThermophoresis (MST).

The anti-Ang2 aptamer may inhibit an interaction between the Ang2 and Tie2.

The anti-Ang2 aptamer of the present disclosure may be capable of reducing and/or ameliorating neovascularization and/or vascular permeability in an animal model, such as in an ocular animal model. For example, the ocular animal model may be an oxygen-induced ischemic retinopathy (OIR) model. The animal model may be a vertebrate animal model, in some cases, the animal model may be a mammal model. The animal may be a rat, a mouse, a rabbit, a goat, a sheep, a non-human primate, or any other suitable animal.

The anti-Ang2 aptamer of the present disclosure may be capable of reducing neovascularization and/or reducing vascular permeability in a mouse oxygen-induced ischemic retinopathy (OIR) model.

The anti-Ang2 aptamer of the present disclosure may be highly soluble. For example, the anti-Ang2 aptamer may be soluble in the solvent with a relatively high degree (e.g. 80% of the whole weight or more, 85% of the whole weight or more, 90% of the whole weight or more, 95% of the whole weight or more, 99% of the whole weight or more). For example, the anti-Ang2 aptamer may be formulated at a concentration of 100 mg/ml or more, at a concentration of 150 mg/ml or more, such as at least 200 mg/ml.

The anti-Ang2 aptamer may be an RNA aptamer, a DNA aptamer, or a combination thereof. For example, the anti-VEGF aptamer may comprise primarily RNA, it may comprise primarily DNA, or it may comprise both RNA and DNA.

The anti-Ang2 aptamer may comprise one or more modified nucleotide. In some cases, all the nucleotides of the anti-Ang2 aptamer may be modified nucleotides.

For example, the modified nucleotide may comprise a chemical substitution or modification at one or more positions independently selected from a ribose position, a deoxyribose position, a phosphate position, and a base position. The modified nucleotide may comprise one or more modifications independently selected from a 2'-position sugar modification, a 2'-amino (2'-$NH_2$) modification, a 2'-fluoro (2'-F) modification, a 2'-O-methyl (2'-OMe) modification, a 2'-O-(2-Methoxyethyl) (2'-O-MOE) modification, a 5-position modified pyrimidine, a modification at a cytosine exocyclic amine, a substitution with 5'-bromouracil, a substitution with 5'-bromodeoxyuridine, a substitution with 5'-bromodeoxycytidine, a backbone modification, a locked nucleic acid (LNA), a methylation, a 3' cap, and a 5' cap. The 5-position modified pyrimidine may be selected from 5-carboxy-2'-deoxyuridine, 5-aminoallyl-2'-deoxyuridine, 5-[(3-indolyl)propionamide-N-allyl]-2'-deoxyuridine, 5-carboxy-2'-deoxycytidine, 5-aminoallyl-2'-deoxycytidine, biotin-16-aminoallyl-2'-deoxycytidine, 5-(N-benzylcarboxyamide)-2'-deoxyuridine, 5-(N-isobutylcarboxyamide)-2'-deoxyuridine, 5-(N-naphthylmethylcarboxyamide)-2'-deoxyuridine, and 5-(N-tryptaminocarboxyamide)-2'-deoxyuridine.

The anti-Ang2 aptamer may comprise at least one (e.g. 1, 2, 3, 4, 5, 6, 7, 8, 9, 10, 11, 12, 13, 14, 15 or more) 2'-modified nucleotide. In some cases, all the nucleotides of the anti-Ang2 aptamer may be 2'-modified nucleotides. The 2'-modified nucleotide may be selected from a 2'-amino modified nucleotide, a 2'-fluoro-modified nucleotide, a 2'-O-methyl-modified nucleotide, and a 2'-O-(2-methoxyethyl)-modified nucleotide. For example, the 2'-fluoro-modified nucleotides may be 2'-fluoro (2'-F)-modified nucleotides or 2'-fluoro-2'-deoxy-modified nucleotides. For example, the 2'-fluoro-modified nucleotides may comprise the following structure:

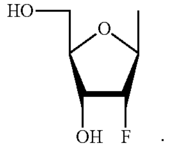

The anti-Ang2 aptamer may comprise at least one 2'-fluoro-modified nucleotide, at least one 2'-O-methyl-modified nucleotide, and/or at least one LNA.

In some cases, all the cytidines of the anti-Ang2 aptamer may be 2'-modified cytidines. In some cases, all the cytidines may be 2'-fluoro-modified cytidines and/or 2'-O-methyl-modified cytidines. In some cases, all the cytidines may be 2'-deoxy-2'-fluorocytidines. In some cases, all the uridines may be 2'-modified uridines. In some cases, all the uridines may be 2'-fluoro-modified uridines and/or 2'-O-methyl-modified uridines. In some cases, all the uridines may be 2'-deoxy-2'-fluorouridines. In some cases, all the adenosines may be 2'-modified adenosines. In some cases, all the adenosines may be 2'-fluoro-modified adenosines and/or 2'-O-methyl-modified adenosines. In some cases, all the adenosines may be 2'-deoxy-2'-fluoroadenosines. In some cases, all the guanosines may be 2'-modified guanosines. In some cases, all the guanosines may be 2'-fluoro-modified guanosines and/or 2'-O-methyl-modified guanosines. In some cases, all the guanosines may be 2'-deoxy-2'-fluoroguanosines. In some cases, all the nucleotides may be 2'-fluoro-modified nucleotides and/or 2'-O-methyl-modified nucleotides. In some cases, all the nucleotides may be 2'-fluoro-modified nucleotides.

In some cases, the anti-Ang2 aptamer does not comprise any natural nucleotide (e.g., unmodified A, C, T, U or G).

The anti-Ang2 aptamer may comprise about 10 to about 150 nucleotides. For example, the anti-Ang2 aptamer may comprise about 10 to about 150 nucleotides, about 10 to about 140 nucleotides, about 10 to about 130 nucleotides, about 10 to about 120 nucleotides, about 10 to about 110 nucleotides, about 10 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, or about 10 to about 20 nucleotides.

The anti-Ang2 aptamer may compete with an anti-Ang2 reference aptamer for binding to the Ang2.

The anti-Ang2 reference aptamer or the anti-Ang2 aptamer of the present disclosure may comprise a nucleotide sequence with or without modifications. For example, the aptamer may comprise natural and/or modified nucleotides. When an aptamer is defined as comprising or consisting of a nucleotide sequence as set forth in a particular SEQ ID NO, the nucleotides within the sequence may be further modified.

According to the present disclosure, the anti-Ang2 aptamer r-AMS0526 has natural nucleotides, and the nucleotide sequence is as set forth in SEQ ID NO: 2; and the anti-Ang2 aptamer AMS0526 has the corresponding 2'-fluoro-modified nucleotides, and the nucleotide sequence is as set forth in SEQ ID NO: 6. Thus, an aptamer comprising a nucleotide sequence as set forth in SEQ ID NO: 2 may encompass both r-AMS0526 and AMS0526, but an aptamer comprising a nucleotide sequence as set forth in SEQ ID NO: 6 may not encompass r-AMS0526.

Similarly, the anti-Ang2 aptamer r-AMS0525 has natural nucleotides, and the nucleotide sequence is as set forth in SEQ ID NO: 1; and the anti-Ang2 aptamer AMS0525 has the corresponding 2'-fluoro-modified nucleotides, and the nucleotide sequence is as set forth in SEQ ID NO: 5. The anti-Ang2 aptamer r-AMS0525.3 has natural nucleotides, and the nucleotide sequence is as set forth in SEQ ID NO: 3; and the anti-Ang2 aptamer AMS0525.3 has the corresponding 2'-fluoro-modified nucleotides, and the nucleotide sequence is as set forth in SEQ ID NO: 7. The anti-Ang2 aptamer r-AMS0525.4 has natural nucleotides, and the nucleotide sequence is as set forth in SEQ ID NO: 4; and the anti-Ang2 aptamer AMS0525.4 has the corresponding 2'-fluoro-modified nucleotides, and the nucleotide sequence is as set forth in SEQ ID NO: 8. The anti-Ang2 aptamer r-AMS0525 has natural nucleotides, and its nucleotide sequence is as set forth in SEQ ID NO: 1; and the anti-Ang2 aptamers AMS0525.5, AMS0525.6, AMS0525.7, or AMS0525.8 have the corresponding nucleotides with various modifications, and their nucleotide sequences are as set forth in SEQ ID NO: 9-12.

The anti-Ang2 reference aptamer or the anti-Ang2 aptamer of the present disclosure may comprise a secondary structure comprising, from 5' to 3' direction, a first stem, a first bulge, a second stem, a second bulge, a third stem, a third bulge, a fourth stem, and a first loop. The anti-Ang2 aptamer may comprise a secondary structure consisting of, from 5' to 3' direction, a first stem, a first bulge, a second stem, a second bulge, a third stem, a third bulge, a fourth stem, and a first loop.

The anti-Ang2 reference aptamer or the anti-Ang2 aptamer of the present disclosure may comprise a first consensus sequence comprising a nucleotide sequence as set forth in any of SEQ ID NO: 13-20.

Alternatively, or in addition, the anti-Ang2 reference aptamer or the anti-Ang2 aptamer of the present disclosure may comprise a second consensus sequence comprising a nucleotide sequence as set forth in any of SEQ ID NO: 21-28.

For example, the anti-Ang2 reference aptamer or the anti-Ang2 aptamer of the present disclosure may comprise a first consensus sequence comprising a nucleotide sequence as set forth is as set forth in SEQ ID NO: 13, as well as a second consensus sequence comprising a nucleotide sequence as set forth is as set forth in SEQ ID NO: 21; the anti-Ang2 reference aptamer or the anti-Ang2 aptamer of the present disclosure may comprise a first consensus sequence comprising a nucleotide sequence as set forth is as set forth in SEQ ID NO:14, as well as a second consensus sequence comprising a nucleotide sequence as set forth is as set forth in SEQ ID NO: 22; the anti-Ang2 reference aptamer or the anti-Ang2 aptamer of the present disclosure may comprise a first consensus sequence comprising a nucleotide sequence as set forth is as set forth in SEQ ID NO: 15, as well as a second consensus sequence comprising a nucleotide sequence as set forth is as set forth in SEQ ID NO: 23; the anti-Ang2 reference aptamer or the anti-Ang2 aptamer of the present disclosure may comprise a first consensus sequence comprising a nucleotide sequence as set forth is as set forth in SEQ ID NO: 16, as well as a second consensus sequence comprising a nucleotide sequence as set forth is as set forth in SEQ ID NO: 24; the anti-Ang2 reference aptamer or the anti-Ang2 aptamer of the present disclosure may comprise a first consensus sequence comprising a nucleotide sequence as set forth is as set forth in SEQ ID NO: 17, as well as a second consensus sequence comprising a nucleotide sequence as set forth is as set forth in SEQ ID NO: 25; the anti-Ang2 reference aptamer or the anti-Ang2 aptamer of the present disclosure may comprise a first consensus sequence comprising a nucleotide sequence as set forth is as set forth in SEQ ID NO: 18, as well as a second consensus sequence comprising a nucleotide sequence as set forth is as set forth in SEQ ID NO: 26; the anti-Ang2 reference aptamer or the anti-Ang2 aptamer of the present disclosure may comprise a first consensus sequence comprising a nucleotide sequence as set forth is as set forth in SEQ ID NO: 19, as well as a second consensus sequence comprising a nucleotide sequence as set forth is as set forth in SEQ ID NO: 27; the anti-Ang2 reference aptamer or the anti-Ang2 aptamer of the present disclosure may comprise a first consensus sequence comprising a nucleotide sequence as set forth is as set forth in SEQ ID NO: 20, as well as a second consensus sequence comprising a nucleotide sequence as set forth is as set forth in SEQ ID NO: 28.

The first consensus sequence may be comprised in the nucleotide sequence forming the first stem, the first bulge, the second stem, the second bulge, the third stem, the third bulge and/or the fourth stem of the anti-Ang2 reference aptamer of the anti-Ang2 aptamer of the present disclosure. In some cases, the first consensus sequence may not be comprised in the nucleotide sequence forming the first loop of the anti-Ang2 reference aptamer or the anti-Ang2 aptamer of the present disclosure. For example, the first consensus sequence may be present anywhere within the aptamer, except in the region forming the first loop.

In some cases, the first consensus sequence may be comprised in the first stem, the first bulge and the second stem. In some cases, the first consensus sequence may be comprised in the first stem, the first bulge, the second stem, and the second bulge. In some cases, the first consensus sequence may be comprised in the first stem, the first bulge, the second stem, the second bulge and the third stem. In some cases, the first consensus sequence may be comprised in the first stem, the first bulge, the second stem, the second bulge, the third stem, and the third bulge. In some cases, the first consensus sequence may be comprised in the first stem, the first bulge, the second stem, the second bulge, the third stem, the third bulge, and the fourth stem. In some cases, the first consensus sequence may be comprised in the second stem, the second bulge and the third stem. In some cases, the first consensus sequence may be comprised in the second stem, the second bulge, the third stem, and the third bulge. In some cases, the first consensus sequence may be comprised in the second stem, the second bulge, the third stem, the third bulge and the fourth stem. In some cases, the first consensus sequence may be comprised in the third stem, the third bulge and the fourth stem.

The second consensus sequence may be comprised in the nucleotide sequence forming the first stem, the first bulge, the second stem, the second bulge, the third stem, the third bulge and/or the fourth stem of the anti-Ang2 reference aptamer or the anti-Ang2 aptamer of the present disclosure. In some cases, the second consensus sequence may not be comprised in the nucleotide sequence forming the first loop of the anti-Ang2 reference aptamer or the anti-Ang2 aptamer of the present disclosure. For example, the second consensus sequence may be present anywhere within the aptamer, except in the region forming the first loop.

In some cases, the second consensus sequence may be comprised in the first stem, the first bulge and the second stem. In some cases, the second consensus sequence may be comprised in the first stem, the first bulge, the second stem, and the second bulge. In some cases, the second consensus sequence may be comprised in the first stem, the first bulge, the second stem, the second bulge and the third stem. In some cases, the second consensus sequence may be comprised in the first stem, the first bulge, the second stem, the second bulge, the third stem, and the third bulge. In some cases, the second consensus sequence may be comprised in the first stem, the first bulge, the second stem, the second bulge, the third stem, the third bulge, and the fourth stem. In some cases, the second consensus sequence may be comprised in the second stem, the second bulge and the third stem. In some cases, the second consensus sequence may be comprised in the second stem, the second bulge, the third stem, and the third bulge. In some cases, the second consensus sequence may be comprised in the second stem, the second bulge, the third stem, the third bulge and the fourth stem. In some cases, the second consensus sequence may be comprised in the third stem, the third bulge and the fourth stem.

The first consensus sequence and the second consensus sequence may be paired to make sure that the secondary structure of the aptamer is properly formed. For example, when a first consensus sequence is chosen, those skilled in the art may be able to adjust the nucleotide sequence of the second consensus sequence, as long as the secondary structure of the aptamer can be properly formed.

The anti-Ang2 reference aptamer or the anti-Ang2 aptamer of the present disclosure may comprise the first consensus sequence and the second consensus sequence, wherein the first consensus sequence may be located 5' to the second consensus sequence.

In some cases, the anti-Ang2 reference aptamer or the anti-Ang2 aptamer of the present disclosure may comprise the first consensus sequence and the second consensus sequence, wherein the second consensus sequence may be located 5' to the first consensus sequence.

For example, 1) the first consensus sequence may be comprised in the second stem, the second bulge, the third stem, the third bulge and the fourth stem; while the second consensus sequence may be comprised in the fourth stem, the third bulge, the third stem, the second bulge and the second stem; 2) the first consensus sequence may be in first bulge, the second stem, the second bulge, the third stem, the third bulge and the fourth stem; while the second consensus sequence may be comprised in the in the fourth stem, the third bulge, the third stem, the second bulge, the second stem and the first bulge; or, 3) the first consensus sequence may be comprised in the nucleotide sequence forming the first stem, the second stem, the second bulge, the third stem, the third bulge and the fourth stem; while the second consensus sequence may be comprised in the fourth stem, the third bulge, the third stem, the second bulge and the second stem, the first bulge and the first stem.

For example, 1) the second consensus sequence may be comprised in the second stem, the second bulge, the third stem, the third bulge and the fourth stem; while the first consensus sequence may be comprised in the fourth stem, the third bulge, the third stem, the second bulge and the second stem; 2) the second consensus sequence may be in first bulge, the second stem, the second bulge, the third stem, the third bulge and the fourth stem; while the first consensus sequence may be comprised in the in the fourth stem, the third bulge, the third stem, the second bulge, the second stem and the first bulge; or, 3) the second consensus sequence may be comprised in the nucleotide sequence forming the first stem, the second stem, the second bulge, the third stem, the third bulge and the fourth stem; while the first consensus sequence may be comprised in the fourth stem, the third bulge, the third stem, the second bulge and the second stem, the first bulge and the first stem.

The first loop of the anti-Ang2 reference aptamer or the anti-Ang2 aptamer of the present disclosure may comprises 2-30 nucleotides (e.g., at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides).

The anti-Ang2 reference aptamer or the anti-Ang2 aptamer of the present disclosure may comprise a nucleotide sequence as set forth in any of SEQ ID NO: 1-12, or a variant or truncate thereof. The variant may comprise a nucleotide sequence that is at least 50% identical to the nucleotide sequence as set forth in any of SEQ ID NO: 1-12. The variant may comprise a nucleotide sequence as set forth in any of SEQ ID NO: 1-12, with one or more (e.g., 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, or more) nucleotide addition, deletion, and/or substitution.

The anti-Ang2 reference aptamer may comprise about 10 to about 150 nucleotides. For example, the anti-Ang2 reference aptamer may comprise about 10 to about 150 nucleotides, about 10 to about 140 nucleotides, about 10 to about 130 nucleotides, about 10 to about 120 nucleotides, about 10 to about 110 nucleotides, about 10 to about 100 nucleotides, about 10 to about 90 nucleotides, about 10 to about 80 nucleotides, about 10 to about 70 nucleotides, about 10 to about 60 nucleotides, about 10 to about 50 nucleotides, about 10 to about 40 nucleotides, about 10 to about 30 nucleotides, or about 10 to about 20 nucleotides.

The anti-Ang2 aptamer may be used for modulating the biological activity of Ang2 or Tie2.

The anti-Ang2 aptamer may be used for preventing, treating, and/or ameliorating a Ang2 related disease, disorder or condition. For example, the Ang2 related disease, disorder or condition may be a neovascular disease, disorder or condition. For example, the Ang2 related disease, disorder or condition may be an ocular neovascular disease, disorder or condition. For example, the Ang2 related disease, disorder or condition may be selected from age-related macular degeneration, choroidal neovascularization, diabetic macular edema, retinal vein occlusion, and diabetic retinopathy. For example, the Ang2 related disease, disorder or condition may be selected from wet age-related macular degeneration, myopic choroidal neovascularization, and proliferative diabetic retinopathy.

In one aspect, the present disclosure provides an anti-Ang2 agent, comprising the aptamer of the present disclosure. The anti-Ang2 agent may further comprise a polyethylene glycol (PEG) moiety. For example, the PEG moiety may be conjugated to the 5' terminus and/or the 3' terminus of the anti-Ang2 aptamer.

In another aspect, the present disclosure provides a composition comprising the anti-Ang2 aptamer, and/or the anti-Ang2 agent of the present application.

In some cases, the composition may be a pharmaceutical composition. For example, the composition may comprise a pharmaceutically acceptable excipient or carrier.

In some cases, the composition may be presented as discrete dosage forms, with each dosage containing a predetermined amount of an active ingredient as a powder or in granules, a solution, or a suspension in an aqueous or non-aqueous liquid. Such dosage forms can be prepared by any of the methods known to a skilled person, for example, it may include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The composition may comprise a therapeutically effective amount of the active composition (e.g., the anti-Ang2 aptamer or the anti-Ang2 agent of the present disclosure). A therapeutically effective amount may be an amount of the subject composition capable of preventing and/or curing (at least partially) a neovascular disease or disorder and/or any complications thereof in a subject suffering from or having a risk of developing the condition or disorder. The specific amount/concentration of the active agent comprised may vary according to the method of administration and the need of a patient, and can be determined based on e.g., volume, viscosity, and/or body weight of a patient etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

The composition may further comprise an effective amount of an additional therapeutically active component, for example, an additional therapeutically active component for preventing, treating and/or ameliorating a neovascular disease or disorder. Each of the active components may be present in the pharmaceutical composition in a pharmaceutically effective amount. The anti-Ang2 aptamer of the present application may or may not be associated with the additional active component.

In some cases, the additional therapeutically active component may be an anti-VEGF agent. The anti-VEGF agent may comprise Aflibercept. The anti-VEGF agent may also comprise the anti-VEGF aptamer of the present disclosure.

Described below are non-limiting exemplary compositions and methods for preparing such a composition. The composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The composition may be in unit dosage forms suitable for single administration of precise dosages. In some embodiments, the composition may be a liquid pharmaceutical composition.

In the composition, the anti-Ang2 aptamer may be combined in an intimate admixture with a pharmaceutical carrier according to conventional pharmaceutical compounding techniques. The carrier may take a wide variety of forms depending on the form of preparation desired for administration.

The composition may further include one or more pharmaceutically acceptable additives and excipients. Such additives and excipients include, without limitation, detackifiers, anti-foaming compositions, buffering compositions, polymers, antioxidants, preservatives, chelating compositions, viscomodulators, tonicifiers, flavorants, colorants, odorants, opacifiers, suspending compositions, binders, fillers, plasticizers, lubricants, and/or mixtures thereof.

In one aspect, the present disclosure provides a method for modulating the biological activity of Ang2 or Tie2, comprising administering to a subject in need thereof an effective amount of the anti-Ang2 aptamer, or the anti-Ang2 agent of the present disclosure.

In one aspect, the present disclosure provides a method for preventing, treating, and/or ameliorating an Ang2 related disease, disorder or condition, comprising administering to a subject in need thereof an effective amount of the anti-Ang2 aptamer, or the anti-Ang2 agent of the present disclosure.

For example, the Ang2 related disease, disorder or condition may be a neovascular disease, disorder or condition may be a neovascular disease, disorder or condition. The Ang2 related disease, disorder or condition may be an ocular neovascular disease, disorder or condition. The Ang2 related disease, disorder or condition may be selected from age-related macular degeneration, choroidal neovascularization, diabetic macular edema, retinal vein occlusion, and diabetic retinopathy. The Ang2 related disease, disorder or condition may be selected from wet age-related macular degeneration, myopic choroidal neovascularization, and proliferative diabetic retinopathy.

The method may further comprise administering to the subject an anti-VEGF agent. The anti-VEGF agent may comprise Aflibercept and/or the anti-VEGF aptamer of the present disclosure.

In another aspect, the present disclosure provides a use of the anti-Ang2 aptamer, or the anti-Ang2 agent of the present disclosure in the manufacture of an agent for modulating the biological activity of Ang2 or Tie2.

In one aspect, the present disclosure provides a use of the aptamer of the present disclosure, or the anti-Ang2 agent of the present disclosure, in the manufacture of a medicament for preventing, treating, and/or ameliorating an Ang2 related disease, disorder or condition.

For example, the Ang2 related disease, disorder or condition may be a neovascular disease, disorder or condition may be a neovascular disease, disorder or condition. The Ang2 related disease, disorder or condition may be an ocular neovascular disease, disorder or condition. The Ang2 related disease, disorder or condition may be selected from age-related macular degeneration, choroidal neovascularization, diabetic macular edema, retinal vein occlusion, and diabetic retinopathy. The Ang2 related disease, disorder or condition may be selected from wet age-related macular degeneration, myopic choroidal neovascularization, and proliferative diabetic retinopathy.

In one aspect, the present disclosure provides a use of 1) the anti-Ang2 aptamer, or the anti-Ang2 agent of the present disclosure in combination with 2) an anti-VEGF agent (e.g., Aflibercept and/or an anti-VEGF aptamer of the present disclosure) in the manufacture of a medicament for preventing, treating, and/or ameliorating a neovascular disease, disorder or condition.

The anti-Ang2 aptamer, or the anti-Ang2 agent of the present disclosure may be administered simultaneously or sequentially with the anti-VEGF agent.

The neovascular disease, disorder or condition may be an ocular neovascular disease, disorder or condition. The neovascular disease, disorder or condition may be selected from age-related macular degeneration, choroidal neovascularization, diabetic macular edema, retinal vein occlusion, and diabetic retinopathy. The neovascular disease, disorder or condition may be selected from wet age-related macular degeneration, myopic choroidal neovascularization, and proliferative diabetic retinopathy.

Bispecific Aptamer

In one aspect, the present disclosure provides a bispecific aptamer comprising an anti-Ang2 aptamer of the present disclosure and an anti-VEGF aptamer of the present disclosure. The bispecific aptamer may be comprised in the composition of the present disclosure.

The bispecific aptamer may be of the formula A1-(L)n-A2, wherein: A1 is an anti-VEGF aptamer of the present disclosure and A2 is an anti-Ang2 aptamer of the present disclosure; or A1 is an anti-Ang2 aptamer of the present disclosure and A2 is an anti-VEGF aptamer of the present disclosure; L is a linker; and n is a number of at least 0. For example, n may be 0 to 20, such as 0, 1, 2, 3, 4, 5, 6, 7, 8, 9, 10, 11, 12, 13, 14, 15, 16, 17, 18, 19, or 20.

The bispecific aptamer may be capable of specifically binding to both VEGF and Ang2.

For example, the bispecific aptamer may bind to VEGF-121 with a $K_D$ value of about 500 pM or less (for example, the bispecific aptamer may bind to VEGF-121 with a $K_D$ value of about 500 picomolar (pM) or less, about 400 picomolar (pM) or less, about 300 picomolar (pM) or less, about 200 picomolar (pM) or less, about 100 picomolar (pM) or less, about 90 picomolar (pM) or less, about 80 picomolar (pM) or less, about 70 picomolar (pM) or less, about 60 picomolar (pM) or less, about 50 picomolar (pM) or less, about 40 picomolar (pM) or less, about 30 picomolar (pM) or less, or about 20 picomolar (pM) or less), and the bispecific aptamer may bind to Ang2 with a $K_D$ value of about 500 pM or less (for example, the bispecific aptamer may bind to Ang2 with a $K_D$ value of about 500 picomolar (pM) or less, about 400 picomolar (pM) or less, about 300 picomolar (pM) or less, about 200 picomolar (pM) or less, about 100 picomolar (pM) or less, about 90 picomolar (pM) or less, about 80 picomolar (pM) or less, about 70 picomolar (pM) or less, about 60 picomolar (pM) or less, about 50 picomolar (pM) or less, about 40 picomolar (pM) or less, about 30 picomolar (pM) or less, or about 20 picomolar (pM) or less).

The L may be selected from a naturally occurring nucleotide linker, a modified nucleotide linker, a hydrocarbon linker, a polyethylene glycol linker and a combination thereof.

In some cases, at least one L may be a polyethylene glycol linker. In some cases, at least one L may be a hexaethylene glycol (also indicated as H or PEG6) linker. For example, the L may be a hexaethylene glycol linker, and n may be 0 to 10 (for example, n is 0, 1, 2, 3, 4, 5, 6, 7, 8, 9 or 10).

For example, A1 may be an anti-VEGF aptamer comprising a nucleotide sequence as set forth in any of SEQ ID NO: 46-135, SEQ ID NO: 200-201, or a variant or truncate thereof; and A2 may be an anti-Ang2 aptamer comprising a nucleotide sequence as set forth in any of SEQ ID NO: 1-12, or a variant or truncate thereof.

As another example, A1 may be an anti-Ang2 aptamer comprising a nucleotide sequence as set forth in any of SEQ ID NO: 1-12, or a variant or truncate thereof; and A2 may be an anti-VEGF aptamer comprising a nucleotide sequence as set forth in any of SEQ ID NO: 46-135, SEQ ID NO: 200-201, or a variant or truncate thereof.

In some cases of the bispecific aptamer, A1 is an anti-VEGF aptamer comprising a nucleotide sequence as set forth in SEQ ID NO: 83, or a truncate thereof, A2 is an anti-Ang2 aptamer comprising a nucleotide sequence as set forth in SEQ ID NO: 2, or a truncate thereof, L is a hexaethylene glycol linker, and n is 0 to 10.

In some cases of the bispecific aptamer, A1 is an anti-VEGF aptamer comprising a nucleotide sequence as set forth in SEQ ID NO: 128, or a truncate thereof, A2 is an anti-Ang2 aptamer comprising a nucleotide sequence as set forth in SEQ ID NO: 6, or a truncate thereof, L is a hexaethylene glycol linker, and n is 0 to 10.

In some cases of the bispecific aptamer, A1 is an anti-Ang2 aptamer comprising a nucleotide sequence as set forth in SEQ ID NO: 2, or a truncate thereof, A2 is an anti-VEGF aptamer comprising a nucleotide sequence as set forth in SEQ ID NO: 83, or a truncate thereof, L is a hexaethylene glycol linker, and n is 0 to 10.

In some cases of the bispecific aptamer, A1 is an anti-Ang2 aptamer comprising a nucleotide sequence as set forth in SEQ ID NO: 6, or a truncate thereof, A2 is an anti-VEGF aptamer comprising a nucleotide sequence as set forth in SEQ ID NO: 128, or a truncate thereof, L is a hexaethylene glycol linker, and n is 0 to 10.

In some cases, the bispecific aptamer may comprise a nucleotide sequence as set forth in any of SEQ ID NO: 140-195, SEQ ID NO: 202-204.

The bispecific aptamer may be selected from r-AMSB107.0, r-AMSB108.0, r-AMSB107.1, r-AMSB107.2, r-AMSB107, r-AMSB107.4, r-AMSB107.5, r-AMSB107.6, r-AMSB107.7, r-AMSB107.8, r-AMSB107.9, r-AMSB107.10, r-AMSB107.11, r-AMSB107.12, r-AMSB107.13, r-AMSB107.14, r-AMSB107.15, r-AMSB107.16, r-AMSB107.17, r-AMSB107.18, r-AMSB107.19, r-AMSB107.22, r-AMSB107.23, r-AMSB107.24, r-AMSB107.25, r-AMSB107.26, r-AMSB107.27, AMSB107.0, AMSB108.0, AMSB107.1, AMSB107.2, AMSB107, AMSB107.4, AMSB107.5, AMSB107.6, AMSB107.7, AMSB107.8, AMSB107.9, AMSB107.10, AMSB107.11, AMSB107.12, AMSB107.13, AMSB107.14, AMSB107.15, AMSB107.16, AMSB107.17, AMSB107.18, AMSB107.19, AMSB107.20, AMSB107.21, AMSB107.22, AMSB107.23, AMSB107.24, AMSB107.25, AMSB107.26, AMSB107.P6, AMSB107.P40K, AMSB107P and AMSB107.27.

The bispecific aptamers r-AMSB107.22, r-AMSB107.23, r-AMSB107.24, r-AMSB107.25, AMSB107.22, AMSB107.23, AMSB107.24, and AMSB107.25 each comprises one or more hexaethylene glycol (also known as PEG6) as a linker (L) or a modification.

Compositions

In one aspect, the present disclosure provides a composition comprising the anti-Ang2 aptamer of the present disclosure, the anti-VEGF aptamer of the present disclosure, and/or the bispecific aptamer of the present disclosure. In some cases, the composition comprises an effective amount of the anti-Ang2 aptamer of the present disclosure and an effective amount of the anti-VEGF aptamer of the present disclosure. In some cases, the composition comprises an effective amount of the bispecific aptamer of the present disclosure.

The composition may be a pharmaceutical composition. The composition may comprise a pharmaceutically acceptable excipient or carrier.

The composition may be used for preventing, treating and/or ameliorating a neovascular disease, disorder or condition. The neovascular disease, disorder or condition may be an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

The composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The composition may be in unit dosage forms suitable for single administration of precise dosages. In some cases, the composition may be a liquid pharmaceutical composition.

The pharmaceutically acceptable excipient or carrier may include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and/or mixtures thereof.

In some cases, the composition may be presented as discrete dosage forms, with each dosage containing a predetermined amount of an active ingredient as a powder or in granules, a solution, or a suspension in an aqueous or non-aqueous liquid. Such dosage forms can be prepared by any of the methods known to a skilled person, for example, it may include the step of bringing the active ingredient into association with the carrier, which constitutes one or more other ingredients. In general, the compositions are prepared by uniformly and intimately mixing the active ingredient with liquid carriers or finely divided solid carriers or both, and then, if necessary, shaping the product into the desired presentation.

The composition may comprise a therapeutically effective amount of the active agent (e.g., the agent of the present disclosure). A therapeutically effective amount may be an amount of the subject composition capable of preventing and/or curing (at least partially) a neovascular disease or disorder and/or any complications thereof in a subject suffering from or having a risk of developing the condition or disorder. The specific amount/concentration of the active agent comprised may vary according to the method of administration and the need of a patient, and can be determined based on e.g., volume, viscosity, and/or body weight of a patient, etc. For example, an appropriate dosage may be about 0.1 mg or 1 mg/kg/day to about 50 mg/kg/day; sometimes, the dosage can be even higher. It shall be understood that these specific doses may be conveniently adjusted by a skilled person in the art (e.g., a doctor or a pharmacist) based on conditions of a specific patient, formulation, and/or disease.

Medical Use and Method

In another aspect, the present disclosure provides a method for preventing, treating and/or ameliorating a neovascular disease, disorder or condition, comprising administering to a subject in need thereof an effective amount of the anti-Ang2 aptamer of the present disclosure, an effective amount of the anti-VEGF aptamer of the present disclosure, an effective amount of the bispecific aptamer of the present disclosure, and/or an effective amount of the composition of the present disclosure.

In another aspect, the present disclosure provides use of the anti-Ang2 aptamer of the present disclosure, the anti-VEGF aptamer of the present disclosure, the bispecific aptamer of the present disclosure, and/or the composition of the present disclosure in the manufacture of a medicament for preventing, treating and/or ameliorating a neovascular disease, disorder or condition.

The neovascular disease, disorder or condition may be an ocular neovascular disease, disorder or condition. In some embodiments, the neovascular disease, disorder or condition is selected from age-related macular degeneration, choroidal neovascularization, diabetic macular edema, retinal vein occlusion, and diabetic retinopathy. In some embodiments, the neovascular disease, disorder or condition is selected from wet age-related macular degeneration, myopic choroidal neovascularization, and proliferative diabetic retinopathy.

Further Embodiments

The present disclosure further provides the following embodiments:

AMSB107.25, AMSB107.26, AMSB107.P6, AMSB107.P40K, AMSB107P

The present disclosure also relates to the following sequences:

| SEQ ID NO. | Name | Sequences |
|---|---|---|
| 1 | r-AMS0525 | GCAUAGAUAAGCCAACAAACGUACAUUCUCUGUUAGUAUUUU CUGCACACCGUCGCUUAGU |
| 2 | r-AMS0526 | CGCAUAGAUAAGCCAACAAACGUACAUUCUCUGUUAGUAUUU UCUGCG |
| 3 | r-AMS0525.3 | GCCUUAGAUAAGCCAACAAACGUACAUUCUCUGUUAGUAUUU UCAGGC |
| 4 | r-AMS0525.4 | CCGAUAAGCCAACAAACGUACAUUCUCUGUUAGUAUUCGG |

-continued

| SEQ ID NO. | Name | Sequences |
|---|---|---|
| 5 | AMS0525 | fGfCfAfUfAfGfAfUfAfAfGfCfCfAfAfCfAfAfAfCfGfUfAfCfAfUfUfCfU<br>fCfUfGfUfUfAfGfUfAfUfUfUfUfCfUfGfCfAfCfAfCfCfGfUfCfGfCfUfU<br>fAfGfU |
| 6 | AMS0526 | fCfGfCfAfUfAfGfAfUfAfAfGfCfCfAfAfCfAfAfAfCfGfUfAfCfAfUfUfC<br>fUfCfUfGfUfUfAfGfUfAfUfUfUfUfCfUfGfCfG |
| 7 | AMS0525.3 | fGfCfCfUfUfAfGfAfUfAfAfGfCfCfAfAfCfAfAfAfCfGfUfAfCfAfUfUfC<br>fUfCfUfGfUfUfAfGfUfAfUfUfUfUfCfAfGfGfC |
| 8 | AMS0525.4 | fCfCfGfAfUfAfAfGfCfCfAfAfCfAfAfAfCfGfUfAfCfAfUfUfCfUfCfUfG<br>fUfUfAfGfUfAfUfUfCfGfG |
| 9 | AMS0525.5 | $_{m}$CmGmCmAfUfAfGfAfUfAfAfGfCfCfAfAfCfAfAfAfCfGfUfAfCfAfUf<br>UfCfUfCfUfGfUfUfAfGfUfAfUfUfUfUfCmUmGmCmG |
| 10 | AMS0525.6 | LCLGLCLAfUfAfGfAfUfAfAfGfCfCfAfAfCfAfAfAfCfGfUfAfCfAfUfU<br>fCfUfCfUfGfUfUfAfGfUfAfUfUfUfUfCLULGLCLG |
| 11 | AMS0525.7 | fCfGfCfAfUfAfGfAfUfAfAfGfCfCfAfAfCfAfAfAHfUfUfCfUfCfUfGfUf<br>UfAfGfUfAfUfUfUfUfCfUfGfCfG |
| 12 | AMS0525.8 | fCfGfCfAfUfAfGfAfUfAfAfGfCfCfAfAfCfAfAfAfCHfAfUfUfCfUfCfUf<br>GfUfUfAfGfUfAfUfUfUfUfCfUfGfCfG |
| 13 | Ang2 1st consensus sequence f1 | fAfGfAfUfAfAfGfCfCfAfAfCfA |
| 14 | Ang2 1st consensus sequence f2 | fUfAfGfAfUfAfAfGfCfCfAfAfCfA |
| 15 | Ang2 1st consensus sequence f3 | fAfUfAfGfAfUfAfAfGfCfCfAfAfCfA |
| 16 | Ang2 1st consensus sequence f4 | fCfUfAfGfAfUfAfAfGfCfCfAfAfCfA |
| 17 | Ang2 1st consensus sequence 1 | AGAUAAGCCAACA |
| 18 | Ang2 1st consensus sequence 2 | UAGAUAAGCCAACA |
| 19 | Ang2 1st consensus sequence 3 | AUAGAUAAGCCAACA |
| 20 | Ang2 1st consensus sequence 4 | CUAGAUAAGCCAACA |
| 21 | Ang2 2nd consensus sequence f1 | fUfGfUfUfAfGfUfAfUfUfUfU |
| 22 | Ang2 2nd consensus sequence f2 | fUfGfUfUfAfGfUfAfUfUfUfUfC |
| 23 | Ang2 2nd consensus sequence f3 | fUfGfUfUfAfGfUfAfUfUfUfUfCfU |
| 24 | Ang2 2nd consensus sequence f4 | fUfGfUfUfAfGfUfAfUfUfUfUfCfG |
| 25 | Ang2 2nd consensus sequence 1 | UGUUAGUAUUUU |

-continued

| SEQ ID NO. | Name | Sequences |
|---|---|---|
| 26 | Ang2 2nd consensus sequence 2 | UGUUAGUAUUUUC |
| 27 | Ang2 2nd consensus sequence 3 | UGUUAGUAUUUUCU |
| 28 | Ang2 2nd consensus sequence 4 | UGUUAGUAUUUUCG |
| 29 | human VEGF121 | APMAEGGGQNHHEVVKFMDVYQRSYCHPIETLVDIFQEYPDEIEYI FKPSCVPLMRCGGCCNDEGLECVPTEESNITMQIMRIKPHQGQHIG EMSFLQHNKCECRPKKDRARQEKCDKPRR |
| 30 | VEGF receptor binding domain 1 | FMDVYQRSY |
| 31 | VEGF receptor binding domain 2 | DIFQEYPDEIEYIFK |
| 32 | VEGF receptor binding domain 3 | CNDEGL |
| 33 | VEGF receptor binding domain 4 | QIMRIKPHQGQHI |
| 34 | VEGF receptor binding domain 5 | KCECRPKK |
| 35 | human VEGF165,Monkey VEGF-165 | APMAEGGGQNHHEVVKFMDVYQRSYCHPIETLVDIFQEYPDEIEYI FKPSCVPLMRCGGCCNDEGLECVPTEESNITMQIMRIKPHQGQHIG EMSFLQHNKCECRPKKDRARQENPCGPCSERRKHLFVQDPQTCKC SCKNTDSRCKARQLELNERTCRCDKPRR |
| 36 | Rabbit VEGF-189 | APMAEEGDNKPHEVVKFMEVYRRSYCQPIETLVDIFQEYPDEIEYIF KPSCVPLVRCGGCCNDESLECVPTEEFNVTMQIMRIKPHQGQHIGE MSFLQHNKCECRPKKDRARQEKKSVRGKGKGQKRKRKKSRYKS WSVPCGPCSERRKHLFVQDPQTCKCSCKNTDSRCKARQLELNERT CRCDKPRR |
| 37 | Rabbit VEGF-189 receptor binding domain 1 | FMEVYRRSY |
| 38 | Rabbit VEGF-189 receptor binding domain 3 | CNDESL |
| 39 | Rat VEGF 164 | APTTEGEQKAHEVVKFMDVYQRSYCRPIETLVDIFQEYPDEIEYIFK PSCVPLMRCAGCCNDEALECVPTSESNVTMQIMRIKPHQSQHIGEM SFLQHSRCECRPKKDRTKPENHCEPCSERRKHLFVQDPQTCKCSCK NTDSRCKARQLELNERTCRCDKPRR |
| 40 | VEGF receptor binding domain 3' | CNDEAL |
| 41 | VEGF receptor binding domain 5' | RCECRPKK |

-continued

| SEQ ID NO. | Name | Sequences |
|---|---|---|
| 42 | Rat VEGF 120 | APTTEGEQKAHEVVKFMDVYQRSYCRPIETLVDIFQEYPDEIEYIFK PSCVPLMRCAGCCNDEALECVPTSESNVTMQIMRIKPHQSQHIGEM SFLQHSRCECRPKKDRTKPEKCDKPRR |
| 43 | Mouse VEGF 164 | APTTEGEQKSHEVIKFMDVYQRSYCRPIETLVDIFQEYPDEIEYIFKP SCVPLMRCAGCCNDEALECVPTSESNITMQIMRIKPHQSQHIGEMSF LQHSRCECRPKKDRTKPENHCEPCSERRKHLFVQDPQTCKCSCKNT DSRCKARQLELNERTCRCDKPRR |
| 44 | Mouse VEGF 120 | APTTEGEQKSHEVIKFMDVYQRSYCRPIETLVDIFQEYPDEIEYIFKP SCVPLMRCAGCCNDEALECVPTSESNITMQIMRIKPHQSQHIGEMSF LQHSRCECRPKKDRTKPEKCDKPRR |
| 45 | Mouse VEGF 120 receptor binding domain 4 | QIMRIKPHQSQHI |
| 46 | r-AMS0431.0 | AGUUAUUUGGUGGAGAGGAUCCAUUUAGCUUAUACAAUUC |
| 47 | r-AMS0432.0 | CCGGCCAUUGGUGGAGAUUAUCCUUUGAGUACGGUUAUUC |
| 48 | r-AMS0433.0 | ACCCUUGCUUGCGUAGCAUUUUACCAGUGAGUCGGAUCUC |
| 49 | r-AMS0434.0 | GACGCGACCUCGUACCCCCUUGUUGUUACGGUCGCGUC |
| 50 | r-AMS0435.0 | GACGCGACCUUUUUGUUCCUUGGCUCCAAGGUCGCGUC |
| 51 | r-AMS0436.0 | GACGCGACCUUGGCUUUAGAGAGUUCCUUGGUCGCGUC |
| 52 | r-AMS0437.0 | CCACAGUAAAUUUGAUUAGUCGUGUGAAGAAAACUGUCAA |
| 53 | r-AMS0438.0 | AAAUAGAAAAUUAAACGACCCUGGGAACGUGAAUACCCAG CCU |
| 54 | r-AMS0439.0 | CCUCGUACAAGGUUUGUAAUCCACAGUAAGGAUGAGCUGA |
| 55 | r-AMS0440.0 | GGAAUCUAAAAUCCGGAUAGAUAAGAAAGUUUGGUGAGCC |
| 56 | r-AMS0441.0 | CUGCUCCAUGUGCAGUUACAAAUGGCCAUCAAUUGGAUUU |
| 57 | r-AMS0442.0 | UGAAUAACGCGGAAAUCUAGAUAGUAAUACGGUUUUUCCC |
| 58 | r-AMS0443.0 | AGACUCUAGAAUGAUGCAUAUCGUUGCAUUACGGUUGUCU |
| 59 | r-AMS0444.0 | UGACUUCCUCUAGAAUACUAUGUACGGUUGGGGUCA |
| 60 | r-AMS0445.0 | AUAGAAGAAUGACGUCAAAAUAACCAAUGUACUGGGCUAC |
| 61 | r-AMS0446.0 | GCGACCUCUAGAAUAGUAAUACGGUUGGUCGC |
| 62 | r-AMS0447.0 | GCGACUUAUGUGUGUUCUAUUUUUUGGUCGC |
| 63 | r-AMS0448.0 | GCGACCUCUAGAAUGGUAACACGGUUGGUCGC |
| 64 | r-AMS0449.0 | GCGACCGUUUUAUGAAAAAGACUUGGGGUUCUACAUGGUCGC |
| 65 | r-AMS0450.0 | GCGACCUGUGUCCUAACUUUUGUAUCGAAUGAUCUGGGUCGC |
| 66 | r-AMS0451.0 | GCGACUUGUGUCUAAACUUUUAUCUAUCCUAGUUGGGUCGC |
| 67 | r-AMS0452.0 | GCGACCAAAGCAUCUAGAUAGUAAUACGGUUUGCUCGGUCGC |
| 68 | r-AMS0453.0 | GCGACCUCACACAAAAUGGUAGCCUAUUAUAUAUACGGUCGC |
| 69 | r-AMS0454.0 | GCGACCUGAAUUCUAGAAUGGUAACACGGUUAUUCUGGUCGC |
| 70 | r-AMS0433.1 | ACCCUUGCUUGCGUAGCAUUUUACCAGUGAGUCGGAUCUCCG CAUAUCUGCG |
| 71 | r-AMS0433.2 | UGCCAGUGAGUCGGAUCUCCGCAUAUCUGCGCGCAUAUCUGC G |
| 72 | r-AMS0433.3 | ACCCUUGCUUGCGUAGCAUUCUGCCAGUGAGUCGGAUCUCCGC AUAUCUGCG |

-continued

| SEQ ID NO. | Name | Sequences |
|---|---|---|
| 73 | r-AMS0433.4 | ACCCUUGCUUGCGCAGCAUUCUGCCAGUGAGUCGGAUCUCCGC<br>AUAUCUGCG |
| 74 | r-AMS0433.5 | CACCAUGCUUGCGUAGCAUCAUCCAGUGAGUCGGAUCUCCGCA<br>UAUCUGCG |
| 75 | r-AMS0433.6 | CCCCAUCUGCGAAGCAGUCAGCCAGUGAGUCGGAUCUCCGCAU<br>AUCUGCG |
| 76 | r-AMS0433.7 | CACAGAGAACUGUGUGCCAGUGAGUCGGAUCUCCGCAUAUCU<br>GCG |
| 77 | r-AMS0433.8 | CGUAGCAUUUUGCCAGUGAGUCGGAUCUCCGCAUAUCUGCG |
| 78 | r-AMS0433.9 | UGAGUCGGAUCUCCGCAUAUCUGCG |
| 79 | r-AMS0433.10 | UGCCAGUGAGUCGGAUCUCCUGUGAGAACACAG |
| 80 | r-AMS0433.11 | CACAGAGAACUGUGCCUAGCAUUUUGCCAGUGAGUCGGAUCU<br>CCGCAUAUCUGCG |
| 81 | r-AMS0433.12 | UGAGCUCGGAUGCUCCGCAUAUCUGCG |
| 82 | r-AMS0433.13 | UUUUGUGCUUGCGUAGCAACCCUCCAGUGAGUCGGAUCUCCG<br>CAUAUCUGCG |
| 83 | r-AMS0433 | UGCAUGCAUUUUACCAGUGAGUCGGAUCUCCGCAUAUCUGCG |
| 84 | r-AMS0433.15 | ACCCUUGCUUGCGUAGCAUUUUACCAGUGAGUCGGAUCUCUG<br>CAUGCA |
| 85 | r-AMS0433.16 | UUUUACCAGUGAGUCGGAUCUCUGCAUGCA |
| 86 | r-AMS0433.17 | UGCACUGCAUUUUACCAGUGAGUCGGAUCUCCGCAUAUCUGC<br>G |
| 87 | r-AMS0433.18 | UGCAUCUGCAUUUUACCAGUGAGUCGGAUCUCCGCAUAUCUG<br>CG |
| 88 | r-AMS0433.19 | CUGUACAGUUUUACCAGUGAGUCGGAUCUCCGCAUAUCUGCG |
| 89 | r-AMS0433.20 | UUUUGCAUGCAUUUUACCAGUGAGUCGGAUCUCCGCAUAUCU<br>GCG |
| 90 | r-AMS0433.21 | GCUGUACAGCUUUUACCAGUGAGUCGGAUCUCCGCAUAUCUG<br>CG |
| 91 | AMS0431.0 | fAfGfUfUfAfUfUfUfGfGfUfGfGfAfGfAfGfGfAfUfCfCfAfUfUfUfAfGf<br>CfUfUfAfUfAfCfAfAfUfUfC |
| 92 | AMS0432.0 | fCfCfGfGfCfCfAfUfUfGfGfUfGfGfAfGfAfUfUfAfUfCfCfUfUfUfGfAfG<br>fUfAfCfGfGfUfUfAfUfUfC |
| 93 | AMS0433.0 | fAfCfCfCfUfUfGfCfUfUfGfCfGfUfAfGfCfAfUfUfUfUfAfCfCfAfGfUfG<br>fAfGfUfCfGfGfAfUfCfUfC |
| 94 | AMS0434.0 | fGfAfCfGfCfGfAfCfCfUfCfGfUfAfCfCfCfCfCfUfUfGfUfUfGfUfUfAfC<br>fGfGfUfCfGfCfGfUfC |
| 95 | AMS0435.0 | fGfAfCfGfCfGfAfCfCfUfUfUfUfUfGfUfUfCfCfUfUfGfGfCfUfCfCfAfA<br>fGfGfUfCfGfCfGfUfC |
| 96 | AMS0436.0 | fGfAfCfGfCfGfAfCfCfUfUfGfGfCfUfUfUfAfGfAfGfAfGfUfUfCfCfUfU<br>fGfGfUfCfGfCfGfUfC |
| 97 | AMS0437.0 | fCfCfAfCfAfGfUfAfAfAfUfUfUfGfAfUfUfAfGfUfCfGfUfGfUfGfAfAf<br>GfAfAfAfAfCfUfGfUfCfAfA |
| 98 | AMS0438.0 | fAfAfAfUfAfGfAfAfAfAfUfUfAfAfAfCfGfAfCfCfCfUfGfGfGfAfAfCf<br>GfUfGfAfAfUfAfCfCfCfAfG fCfCfU |
| 99 | AMS0439.0 | fCfCfUfCfGfUfAfCfAfAfGfGfUfUfUfGfUfAfAfUfCfCfAfCfAfGfUfAfA<br>fGfGfAfUfGfAfGfCfUfGfA |
| 100 | AMS0440.0 | fGfGfAfAfUfCfUfAfAfAfAfUfCfCfGfGfAfUfAfGfAfUfAfAfGfAfAfAf<br>GfUfUfUfGfGfUfGfAfGfCfC |

-continued

| SEQ ID NO. | Name | Sequences |
|---|---|---|
| 101 | AMS0441.0 | fCfUfGfCfUfCfCfAfUfGfUfGfCfAfGfUfUfAfCfAfAfAfUfGfGfCfCfAfU<br>fCfAfAfUfUfGfGfAfUfUfU |
| 102 | AMS0442.0 | fUfGfAfAfUfAfAfCfGfCfGfGfAfAfAfUfCfUfAfGfAfUfAfGfUfAfAfUf<br>AfCfGfGfUfUfUfUfUfCfCfC |
| 103 | AMS0443.0 | fAfGfAfCfUfCfUfAfGfAfAfUfGfAfUfGfCfAfUfAfUfCfGfUfUfGfCfAf<br>UfUfAfCfGfGfUfUfGfUfCfU |
| 104 | AMS0444.0 | fUfGfAfCfUfUfCfCfUfCfUfAfGfAfAfUfAfCfUfAfUfGfUfAfCfGfGfUfU<br>fGfGfGfGfUfCfA |
| 105 | AMS0445.0 | fAfUfAfGfAfAfGfAfAfUfGfAfCfGfUfCfAfAfAfAfUfAfAfCfCfAfAfUf<br>GfUfAfCfUfGfGfGfCfUfAfC |
| 106 | AMS0446.0 | fGfCfGfAfCfCfUfCfUfAfGfAfAfUfAfGfUfAfAfUfAfCfGfGfUfUfGfGf<br>UfCfGfC |
| 107 | AMS0447.0 | fGfCfGfAfCfUfUfAfUfGfUfGfUfGfUfUfCfUfAfUfUfUfUfUfUfGfGfUf<br>CfGfC |
| 108 | AMS0448.0 | fGfCfGfAfCfCfUfCfUfAfGfAfAfUfGfGfUfAfAfCfAfCfGfGfUfUfGfGfU<br>fCfGfC |
| 109 | AMS0449.0 | fGfCfGfAfCfCfGfUfUfUfUfAfUfGfAfAfAfAfAfGfAfCfUfUfGfGfGfGf<br>UfUfCfUfAfCfAfUfGfGfUfCfGfC |
| 110 | AMS0450.0 | fGfCfGfAfCfCfUfGfUfGfUfCfCfUfAfAfCfUfUfUfUfGfUfAfUfCfGfAfA<br>fUfGfAfUfCfUfGfGfGfUfCfGfC |
| 111 | AMS0451.0 | fGfCfGfAfCfUfUfGfUfGfUfCfUfAfAfAfCfUfUfUfUfAfUfCfUfAfUfCfC<br>fUfAfGfUfUfGfGfGfUfCfGfC |
| 112 | AMS0452.0 | fGfCfGfAfCfCfAfAfAfGfCfAfUfCfUfAfGfAfUfAfGfUfAfAfUfAfCfGfG<br>fUfUfUfGfCUfCfGfGfUfCfGfC |
| 113 | AMS0453.0 | fGfCfGfAfCfCfUfCfAfCfAfCfAfAfAfAfUfGfGfUfAfGfCfCfUfAfUfUfA<br>fUfAfUfAfUfAfCfGfGfUfCfGfC |
| 114 | AMS0454.0 | fGfCfGfAfCfCfUfGfAfAfUfUfCfUfAfGfAfAfUfGfGfUfAfAfCfAfCfGfG<br>fUfUfAfUfUfCfUfGfGfUfCfGfC |
| 115 | AMS0433.1 | fAfCfCfCfUfUfGfCfUfUfGfCfGfUfAfGfCfAfUfUfUfUfAfCfCfAfGfUfG<br>fAfGfUfCfGfGfAfUfCfUfCfCfGfCfAfUfAfUfCfUfGfCfG |
| 116 | AMS0433.2 | fUfGfCfCfAfGfUfGfAfGfUfCfGfGfAfUfCfUfCfCfGfCfAfUfAfUfCfUfG<br>fCfGfCfGfCfAfUfAfUfCfUfGfCfG |
| 117 | AMS0433.3 | fAfCfCfCfUfUfGfCfUfUfGfCfGfUfAfGfCfAfUfUfCfUfGfCfCfAfGfUfG<br>fAfGfUfCfGfGfAfUfCfUfCfCfGfCfAfUfAfUfCfUfGfCfG |
| 118 | AMS0433.4 | fAfCfCfCfUfUfGfCfUfUfGfCfGfCfAfGfCfAfUfUfCfUfGfCfCfAfGfUfG<br>fAfGfUfCfGfGfAfUfCfUfCfCfGfCfAfUfAfUfCfUfGfCfG |
| 119 | AMS0433.5 | fCfAfCfCfAfUfGfCfUfUfGfCfGfUfAfGfCfAfUfCfAfUfCfCfAfGfUfGfA<br>fGfUfCfGfGfAfUfCfUfCfCfGfCfAfUfAfUfCfUfGfCfG |
| 120 | AMS0433.6 | fCfCfCfCfAfUfCfUfGfCfGfAfAfGfCfAfGfUfCfAfGfCfCfAfGfUfGfAfG<br>fUfCfGfGfAfUfCfUfCfCfGfCfAfUfAfUfCfUfGfCfG |
| 121 | AMS0433.7 | fCfAfCfAfGfAfGfAfAfCfUfGfUfGfUfGfCfCfAfGfUfGfAfGfUfCfGfGfA<br>fUfCfUfCfCfGfCfAfUfAfUfCfUfGfCfG |
| 122 | AMS0433.8 | fCfGfUfAfGfCfAfUfUfUfUfGfCfCfAfGfUfGfAfGfUfCfGfGfAfUfCfUfC<br>fCfGfCfAfUfAfUfCfUfGfCfG |
| 123 | AMS0433.9 | fUfGfAfGfUfCfGfGfAfUfCfUfCfCfGfCfAfUfAfUfCfUfGfCfG |
| 124 | AMS0433.10 | fUfGfCfCfAfGfUfGfAfGfUfCfGfGfAfUfCfUfCfCfUfGfUfGfAfGfAfAfC<br>fAfCfAfG |
| 125 | AMS0433.11 | fCfAfCfAfGfAfGfAfAfCfUfGfUfGfCfCfUfAfGfCfAfUfUfUfUfGfCfCfA<br>fGfUfGfAfGfUfCfGfGfAfUfCfUfCfCfGfCfAfUfAfUfCfUfGfCfG |
| 126 | AMS0433.12 | fUfGfAfGfCfUfCfGfGfAfUfGfCfUfCfCfGfCfAfUfAfUfCfUfGfCfG |

-continued

| SEQ ID NO. | Name | Sequences |
|---|---|---|
| 127 | AMS0433.13 | fUfUfUfUfGfUfGfCfUfUfGfCfGfUfAfGfCfAfAfCfCfCfUfCfCfAfGfUfG fAfGfUfCfGfGfAfUfCfUfCfCfGfCfAfUfAfUfCfUfGfCfG |
| 128 | AMS0433 | fUfGfCfAfUfGfCfAfUfUfUfUfAfCfCfAfGfUfGfAfGfUfCfGfGfAfUfCfU fCfCfGfCfAfUfAfUfCfUfGfCfG |
| 129 | AMS0433.15 | fAfCfCfCfUfUfGfCfUfUfGfCfGfUfAfGfCfAfUfUfUfUfAfCfCfAfGfUfG fAfGfUfCfGfGfAfUfCfUfCfUfGfCfAfUfGfCfA |
| 130 | AMS0433.16 | fUfUfUfUfAfCfCfAfGfUfGfAfGfUfCfGfGfAfUfCfUfCfUfGfCfAfUfGfC fA |
| 131 | AMS0433.17 | fUfGfCfAfCfUfGfCfAfUfUfUfUfAfCfCfAfGfUfGfAfGfUfCfGfGfAfUfC fUfCfCfGfCfAfUfAfUfCfUfGfCfG |
| 132 | AMS0433.18 | fUfGfCfAfUfCfUfGfCfAfUfUfUfUfAfCfCfAfGfUfGfAfGfUfCfGfGfAfU fCfUfCfCfGfCfAfUfAfUfCfUfGfCfG |
| 133 | AMS0433.19 | fCfUfGfUfAfCfAfGfUfUfUfUfAfCfCfAfGfUfGfAfGfUfCfGfGfAfUfCfU fCfCfGfCfAfUfAfUfCfUfGfCfG |
| 134 | AMS0433.20 | fUfUfUfUfGfCfAfUfGfCfAfUfUfUfUfAfCfCfAfGfUfGfAfGfUfCfGfGf AfUfCfUfCfCfGfCfAfUfAfUfCfUfGfCfG |
| 135 | AMS0433.21 | fGfCfUfGfUfAfCfAfGfCfUfUfUfUfAfCfCfAfGfUfGfAfGfUfCfGfGfAfU fCfUfCfCfGfCfAfUfAfUfCfUfGfCfG |
| 136 | VEGF 1st consensus sequence f1 | fCfCfAfGfUfGfAfGfUfCfGfGfAfUfCfUfC |
| 137 | VEGF 1st consensus sequence 1 | CCAGUGAGUCGGAUCUC |
| 138 | VEGF 2nd consensus sequence f1 | FCfGfCfAfUfAfUfCfUfGfCfG |
| 139 | VEGF 2nd consensus sequence 1 | CGCAUAUCUGCG |
| 140 | r-AMSB107.0 | ACCCUUGCUUGCGUAGCAUUUUACCAGUGAGUCGGAUCUCCG CAUAGAUAAGCCAACAAACGUACAUUCUCUGUUAGUAUUUUC UGCG |
| 141 | r-AMSB108.0 | CGCAUAGAUAAGCCAACAAACGUACAUUCUCUGUUAGUAUUU UCUGCGUGCCAGUGAGUCGGAUCUCCACAGUUCUCUGUG |
| 142 | r-AMSB 107.1 | UGCCAGUGAGUCGGAUCUCCGCAUAGAUAAGCCAACAAACGU ACAUUCUCUGUUAGUAUUUUCUGCG |
| 143 | r-AMSB 107.2 | UGCCAGUGAGUCGGAUCUCCACAGUAGAUAAGCCAACAAACG UACAUUCUCUGUUAGUAUUUUCCUGUG |
| 144 | r-AMSB 107 | UGCAUGCAUUUUACCAGUGAGUCGGAUCUCCGCAUAGAUAAG CCAACAAACGUACAUUCUCUGUUAGUAUUUUCUGCG |
| 145 | r-AMSB 107.4 | GCAUGCUUUUACCAGUGAGUCGGAUCUCCGCAUAGAUAAGCC AACAAACGUACAUUCUCUGUUAGUAUUUUCUGCG |
| 146 | r-AMSB107.5 | AUGCAUGCAUUUUUACCAGUGAGUCGGAUCUCCGCAUAGAUA AGCCAACAAACGUACAUUCUCUGUUAGUAUUUUCUGCG |
| 147 | r-AMSB107.6 | UGCAUGCAACCAGUGAGUCGGAUCUCCGCAUAGAUAAGCCAA CAAACGUACAUUCUCUGUUAGUAUUUUCUGCG |
| 148 | r-AMSB107.7 | UGCAUGCACAGUGAGUCGGAUCUCCGCAUAGAUAAGCCAACA AACGUACAUUCUCUGUUAGUAUUUUCUGCG |
| 149 | r-AMSB 107.8 | UUUUGCAUGCAUUUUACCAGUGAGUCGGAUCUCCGCAUAGAU AAGCCAACAAACGUACAUUCUCUGUUAGUAUUUUCUGCG |
| 150 | r-AMSB 107.9 | UGCAUGCAUUACCAGUGAGUCGGAUCUCCGCAUAGAUAAGCC AACAAACGUACAUUCUCUGUUAGUAUUUUCUGCG |

-continued

| SEQ ID NO. | Name | Sequences |
|---|---|---|
| 151 | r-<br>AMSB107.10 | UGCAUGCAUUUUUUACCAGUGAGUCGGAUCUCCGCAUAGAUA<br>AGCCAACAAACGUACAUUCUCUGUUAGUAUUUUCUGCG |
| 152 | r-<br>AMSB107.il | UGCAUGCAUUUUCCAGUGAGUCGGAUCUCCGCAUAGAUAAGC<br>CAACAAACGUACAUUCUCUGUUAGUAUUUUCUGCG |
| 153 | r-<br>AMSB107.12 | CUGUACAGUUUUACCAGUGAGUCGGAUCUCCGCAUAGAUAAG<br>CCAACAAACGUACAUUCUCUGUUAGUAUUUUCUGCG |
| 154 | r-<br>AMSB107.13 | CCGGUACCGGUUUUACCAGUGAGUCGGAUCUCCGCAUAGAUA<br>AGCCAACAAACGUACAUUCUCUGUUAGUAUUUUCUGCG |
| 155 | r-<br>AMSB107.14 | UGCACUGCAUUUUACCAGUGAGUCGGAUCUCCGCAUAGAUAA<br>GCCAACAAACGUACAUUCUCUGUUAGUAUUUUCUGCG |
| 156 | r-<br>AMSB107.15 | UGCAUCUGCAUUUUACCAGUGAGUCGGAUCUCCGCAUAGAUA<br>AGCCAACAAACGUACAUUCUCUGUUAGUAUUUUCUGCG |
| 157 | r-<br>AMSB107.16 | UGCAUGCAUUUUACCAGUGAGUCGGAUCUCUUUCGCAUAGAU<br>AAGCCAACAAACGUACAUUCUCUGUUAGUAUUUUCUGCG |
| 158 | r-<br>AMSB107.17 | GCUGUACAGCUUUUACCAGUGAGUCGGAUCUCCGCAUAGAUA<br>AGCCAACAAACGUACAUUCUCUGUUAGUAUUUUCUGCG |
| 159 | r-<br>AMSB107.18 | UGCAUGCAUUUUACCAGULGLALGUCGGAUCLUCCGCAUAGAU<br>AAGCCAACAAACGUACAUUCUCUGUUAGUAUUUUCUGCG |
| 160 | r-<br>AMSB107.19 | UGCAUGCAUUUUACCLALGLUGAGUCGGAUCUCCGCAUAGAUA<br>AGCCAACAAACGUACAUUCUCUGUUAGUAUUUUCUGCG |
| 161 | r-<br>AMSB107.22 | UGCAUGCAHCCAGUGAGUCGGAUCUCCGCAUAGAUAAGCCAA<br>CAAACGUACAUUCUCUGUUAGUAUUUUCUGCG |
| 162 | r-<br>AMSB107.23 | HUGCAUGCAUUUUACCAGUGAGUCGGAUCUCCGCAUAGAUAA<br>GCCAACAAACGUACAUUCUCUGUUAGUAUUUUCUGCG |
| 163 | r-<br>AMSB107.24 | UGCAUGCAUUUUACCAGUGAGUCGGAUCUCCGCAUAGAUAAG<br>CCAACAAAHUUCUCUGUUAGUAUUUUCUGCG |
| 164 | r-<br>AMSB107.25 | UGCAUGCAUUUUACCAGUGAGUCGGAUCUCCGCAUAGAUAAG<br>CCAACAAACHGUUCUCUGUUAGUAUUUUCUGCG |
| 165 | r-<br>AMSB107.26 | UGCAUGCAOOCCAGUGAGUCGGAUCUCCGCAUAGAUAAGCCA<br>ACAAACGUACAUUCUCUGUUAGUAUUUUCUGCG |
| 166 | r-<br>AMSB107.27 | UGCAUGCAOOOOCCAGUGAGUCGGAUCUCCGCAUAGAUAAGC<br>CAACAAACGUACAUUCUCUGUUAGUAUUUUCUGCG |
| 167 | AMSB107.0 | fAfCfCfCfUfUfGfCfUfUfGfCfGfUfAfGfCfAfUfUfUfUfAfCfCfAfGfUfG<br>fAfGfUfCfGfGfAfUfCfUfCfCfGfCfAfUfAfGfAfUfAfAfGfCfCfAfAfCfA<br>fAfAfCfGfUfAfCfAfUfUfCfUfCfUfGfUfUfAfGfUfAfUfUfUfUfCfUfGfC<br>fG |
| 168 | AMSB108.0 | fCfGfCfAfUfAfGfAfUfAfAfGfCfCfAfAfCfAfAfAfCfGfUfAfCfAfUfUfC<br>fUfCfUfGfUfUfAfGfUfAfUfUfUfUfCfUfGfCfGfUfGfCfCfAfGfUfGfAf<br>GfUfCfGfGfAfUfCfUfCfCfAfCfAfGfUfUfCfUfCfUfGfUfG |
| 169 | AMSB107.1 | fUfGfCfCfAfGfUfGfAfGfUfCfGfGfAfUfCfUfCfCfGfCfAfUfAfGfAfUfA<br>fAfGfCfCfAfAfCfAfAfAfCfGfUfAfCfAfUfUfCfUfCfUfGfUfUfAfGfUfA<br>fUfUfUfUfCfUfGfCfG |
| 170 | AMSB107.2 | fUfGfCfCfAfGfUfGfAfGfUfCfGfGfAfUfCfUfCfCfAfCfAfGfUfAfGfAfU<br>fAfAfGfCfCfAfAfCfAfAfAfCfGfUfAfCfAfUfUfCfUfCfUfGfUfUfAfGfU<br>fAfUfUfUfUfCfCfUfGfUfG |
| 171 | AMSB107 | fUfGfCfAfUfGfCfAfUfUfUfUfAfCfCfAfGfUfGfAfGfUfCfGfGfAfUfCfU<br>fCfCfGfCfAfUfAfGfAfUfAfAfGfCfCfAfAfCfAfAfAfCfGfUfAfCfAfUfU<br>fCfUfCfUfGfUfUfAfGfUfAfUfUfUfUfCfUfGfCfG |
| 172 | AMSB107.4 | fGfCfAfUfGfCfUfUfUfUfAfCfCfAfGfUfGfAfGfUfCfGfGfAfUfCfUfCfC<br>fGfCfAfUfAfGfAfUfAfAfGfCfCfAfAfCfAfAfAfCfGfUfAfCfAfUfUfCfU<br>fCfUfGfUfUfAfGfUfAfUfUfUfUfCfUfGfCfG |
| 173 | AMSB107.5 | fAfUfGfCfAfUfGfCfAfUfUfUfUfUfAfCfCfAfGfUfGfAfGfUfCfGfGfAf<br>UfCfUfCfCfGfCfAfUfAfGfAfUfAfAfGfCfCfAfAfCfAfAfAfCfGfUfAfCf<br>AfUfUfCfUfCfUfGfUfUfAfGfUfAfUfUfUfUfCfUfGfCfG |

-continued

| SEQ ID NO. | Name | Sequences |
|---|---|---|
| 174 | AMSB107.6 | fUfGfCfAfUfGfCfAfAfCfCfAfGfUfGfAfGfUfCfGfGfAfUfCfUfCfCfGfC<br>fAfUfAfGfAfUfAfAfGfCfCfAfAfCfAfAfAfCfGfUfAfCfAfUfUfCfUfCfU<br>fGfUfUfAfGfUfAfUfUfUfUfCfUfGfCfG |
| 175 | AMSB107.7 | fUfGfCfAfUfGfCfAfCfAfGfUfGfAfGfUfCfGfGfAfUfCfUfCfCfGfCfAfU<br>fAfGfAfUfAfAfGfCfCfAfAfCfAfAfAfCfGfUfAfCfAfUfUfCfUfCfUfGfU<br>fUfAfGfUfAfUfUfUfUfCfUfGfCfG |
| 176 | AMSB107.8 | fUfUfUfUfGfCfAfUfGfCfAfUfUfUfUfAfCfCfAfGfUfGfAfGfUfCfGfGf<br>AfUfCfUfCfCfGfCfAfUfAfGfAfUfAfAfGfCfCfAfAfCfAfAfAfCfGfUfAf<br>CfAfUfUfCfUfCfUfGfUfUfAfGfUfAfUfUfUfUfCfUfGfCfG |
| 177 | AMSB107.9 | fUfGfCfAfUfGfCfAfUfUfAfCfCfAfGfUfGfAfGfUfCfGfGfAfUfCfUfCfC<br>fGfCfAfUfAfGfAfUfAfAfGfCfCfAfAfCfAfAfAfCfGfUfAfCfAfUfUfCfU<br>fCfUfGfUfUfAfGfUfAfUfUfUfUfCfUfGfCfG |
| 178 | AMSB107.10 | fUfGfCfAfUfGfCfAfUfUfUfUfUfUfAfCfCfAfGfUfGfAfGfUfCfGfGfAf<br>UfCfUfCfCfGfCfAfUfAfGfAfUfAfAfGfCfCfAfAfCfAfAfAfCfGfUfAfCf<br>AfUfUfCfUfCfUfGfUfUfAfGfUfAfUfUfUfUfCfUfGfCfG |
| 179 | AMSB107.11 | fUfGfCfAfUfGfCfAfUfUfUfUfCfCfAfGfUfGfAfGfUfCfGfGfAfUfCfUfC<br>fCfGfCfAfUfAfGfAfUfAfAfGfCfCfAfAfCfAfAfAfCfGfUfAfCfAfUfUfC<br>fUfCfUfGfUfUfAfGfUfAfUfUfUfUfCfUfGfCfG |
| 180 | AMSB107.12 | fCfUfGfUfAfCfAfGfUfUfUfUfAfCfCfAfGfUfGfAfGfUfCfGfGfAfUfCfU<br>fCfCfGfCfAfUfAfGfAfUfAfAfGfCfCfAfAfCfAfAfAfCfGfUfAfCfAfUfU<br>fCfUfCfUfGfUfUfAfGfUfAfUfUfUfUfCfUfGfCfG |
| 181 | AMSB107.13 | fCfCfGfGfUfAfCfCfGfGfUfUfUfUfAfCfCfAfGfUfGfAfGfUfCfGfGfAfU<br>fCfUfCfCfGfCfAfUfAfGfAfUfAfAfGfCfCfAfAfCfAfAfAfCfGfUfAfCfA<br>fUfUfCfUfCfUfGfUfUfAfGfUfAfUfUfUfUfCfUfGfCfG |
| 182 | AMSB107.14 | fUfGfCfAfCfUfGfCfAfUfUfUfUfAfCfCfAfGfUfGfAfGfUfCfGfGfAfUfC<br>fUfCfCfGfCfAfUfAfGfAfUfAfAfGfCfCfAfAfCfAfAfAfCfGfUfAfCfAfU<br>fUfCfUfCfUfGfUfUfAfGfUfAfUfUfUfUfCfUfGfCfG |
| 183 | AMSB107.15 | fUfGfCfAfUfCfUfGfCfAfUfUfUfUfAfCfCfAfGfUfGfAfGfUfCfGfGfAfU<br>fCfUfCfCfGfCfAfUfAfGfAfUfAfAfGfCfCfAfAfCfAfAfAfCfGfUfAfCfA<br>fUfUfCfUfCfUfGfUfUfAfGfUfAfUfUfUfUfCfUfGfCfG |
| 184 | AMSB107.16 | fUfGfCfAfUfGfCfAfUfUfUfUfAfCfCfAfGfUfGfAfGfUfCfGfGfAfUfCfU<br>fCfUfUfUfCfGfCfAfUfAfGfAfUfAfAfGfCfCfAfAfCfAfAfAfCfGfUfAfC<br>fAfUfUfCfUfCfUfGfUfUfAfGfUfAfUfUfUfUfCfUfGfCfG |
| 185 | AMSB107.17 | fGfCfUfGfUfAfCfAfGfCfUfUfUfUfAfCfCfAfGfUfGfAfGfUfCfGfGfAfU<br>fCfUfCfCfGfCfAfUfAfGfAfUfAfAfGfCfCfAfAfCfAfAfAfCfGfUfAfCfA<br>fUfUfCfUfCfUfGfUfUfAfGfUfAfUfUfUfUfCfUfGfCfG |
| 186 | AMSB107.18 | fUfGfCfAfUfGfCfAfUfUfUfUfAfCfCfAfGfULGLALGfUfCfGfGfAfUfC<br>LUfCfCfGfCfAfUfAfGfAfUfAfAfGfCfCfAfAfCfAfAfAfCfGfUfAfCfAf<br>UfUfCfUfCfUfGfUfUfAfGfUfAfUfUfUfUfCfUfGfCfG |
| 187 | AMSB107.19 | fUfGfCfAfUfGfCfAfUfUfUfUfAfCfCLALGLUfGfAfGfUfCfGfGfAfUfC<br>fUfCfCfGfCfAfUfAfGfAfUfAfAfGfCfCfAfAfCfAfAfAfCfGfUfAfCfAfU<br>fUfCfUfCfUfGfUfUfAfGfUfAfUfUfUfUfCfUfGfCfG |
| 188 | AMSB107.20 | LULGLCLALULGLCLAfUfUfUfUfAfCfCfAfGfUfGfAfGfUfCfGfGfAf<br>UfCfUfCLCLGLCLAfUfAfGfAfUfAfAfGfCfCfAfAfCfAfAfAfCfGfUfAf<br>CfAfUfUfCfUfCfUfGfUfUfAfGfUfAfUfUfUfUfCLULGLCLG |
| 189 | AMSB107.21 | mUmGmCmAmUmGmCmAfUfUfUfUfAfCfCfAfGfUfGfAfGfUfCfGfGf<br>AfUfCfUfCmCmGmCmAfUfAfGfAfUfAfAfGfCfCfAfAfCfAfAfAfCfGf<br>UfAfCfAfUfUfCfUfCfUfGfUfUfAfGfUfAfUfUfUfUfCmUmGmCmG |
| 190 | AMSB107.22 | fUfGfCfAfUfGfCfAHfCfCfAfGfUfGfAfGfUfCfGfGfAfUfCfUfCfCfGfCf<br>AfUfAfGfAfUfAfAfGfCfCfAfAfCfAfAfAfCfGfUfAfCfAfUfUfCfUfCfUf<br>GfUfUfAfGfUfAfUfUfUfUfCfUfGfCfG |
| 191 | AMSB107.23 | HfUfGfCfAfUfGfCfAfUfUfUfUfAfCfCfAfGfUfGfAfGfUfCfGfGfAfUfCf<br>UfCfCfGfCfAfUfAfGfAfUfAfAfGfCfCfAfAfCfAfAfAfCfGfUfAfCfAfUf<br>UfCfUfCfUfGfUfUfAfGfUfAfUfUfUfUfCfUfGfCfG |
| 192 | AMSB107.24 | fUfGfCfAfUfGfCfAfUfUfUfUfAfCfCfAfGfUfGfAfGfUfCfGfGfAfUfCfU<br>fCfCfGfCfAfUfAfGfAfUfAfAfGfCfCfAfAfCfAfAfAHfUfUfCfUfCfUfGf<br>UfUfAfGfUfAfUfUfUfUfCfUfGfCfG |

-continued

| SEQ ID NO. | Name | Sequences |
|---|---|---|
| 193 | AMSB107.25 | fUfGfCfAfUfGfCfAfUfUfUfUfAfCfCfAfGfUfGfAfGfUfCfGfGfAfUfCfU fCfCfGfCfAfUfAfGfAfUfAfAfGfCfCfAfAfCfAfAfAfCHfGfUfUfCfUfCf UfGfUfUfAfGfUfAfUfUfUfUfCfUfGfCfG |
| 194 | AMSB107.26 | fUfGfCfAfUfGfCfAOOfCfCfAfGfUfGfAfGfUfCfGfGfAfUfCfUfCfCfGf CfAfUfAfGfAfUfAfAfGfCfCfAfAfCfAfAfAfCfGfUfAfCfAfUfUfCfUfCf UfGfUfUfAfGfUfAfUfUfUfUfCfUfGfCfG |
| 195 | AMSB107.27 | fUfGfCfAfUfGfCfAOOOOfCfCfAfGfUfGfAfGfUfCfGfGfAfUfCfUfCfCf GfCfAfUfAfGfAfUfAfAfGfCfCfAfAfCfAfAfAfCfGfUfAfCfAfUfUfCfUf CfUfGfUfUfAfGfUfAfUfUfUfUfCfUfGfCfG |
| 200 | AMS0433.m4 | fUfGfCfAfUfGfCfAmUmUmUmUmAmCfCfAfGfUfGfAfGfUmCfGfGfA mUfCfUfCmCmGmCmAmUmAmUmCmUmGmCmG |
| 201 | AMS0433.m6 | mUmGmCmAmUmGmCmAmUmUmUmUmAmCfCfAfGfUfGfAfGfUm CfGfGfAmUfCfUfCfCfGfCfAfUfAfUfCfUfGfCfG |
| 202 | AMSB107.P6 | fUfGfCfAfUfGfCfAHfCfCfAfGfUfGfAfGfUfCfGfGfAfUfCfUfCfCfGfCf AfUfAfGfAfUfAfAfGfCfCfAfAfCfAfAfAfCfGfUfAfCfAfUfUfCfUfCfUf GfUfUfAfGfUfAfUfUfUfUfCfUfGfCfG |
| 203 | AMSB107.P40K | fUfGfCfAfUfGfCfAfUfUfUfUfAfCfCfAfGfUfGfAfGfUfCfGfGfAfUfCfU fCfCfGfCfAfUfAfGfAfUfAfAfGfCfCfAfAfCfAfAfAfCfGfUfAfCfAfUfU fCfUfCfUfGfUfUfAfGfUfAfUfUfUfUfCfUfGfCfG, with 40 kDa PEG conjugated at 5'-end |
| 204 | AMSB107P | fUfGfCfAfUfGfCfAmUmUmUmUmAmCfCfAfGfUfGfAfGfUmCfGfGfA mUfCfUfCfCfGfCfAmUmAfGfAfUfAfAfGfCfCfAfAfCfAfAfAmCmGm UmAmCmAfUfUfCfUfCfUfGfUfUfAfGfUfAfUfUfUfUfCmUmGmCmG, with 40 kDa PEG conjugated at 5'-end |

The following examples are set forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1 Anti-VEGF Aptamer Selection

The anti-VEGF aptamers of the present disclosure were identified using Chemically-Augmented Particle Display (CAPD), a platform as described (please refers to Wang et al. WO 2018064086A1; Wang et al. WO2018102115A1; Wang et al. PCT/US2013/071318). Detailed methods and steps were as described in e.g., WO 2018064086A1, which is incorporated herein by reference in its entirety.

Briefly, recombinant human VEGF-121 and VEGF-165 protein from various vendors (listed in Table 1 were used as the target protein for aptamer discovery. A typical initial selection library contains a 40-50 nucleotide random region in which all nucleotides containing a 2'-fluoro (2'-F) modification. For example, for the selection against human VEGF-121 (R&D systems, 4644-vs-CF), the forward primer used was 5'-CGCCCTCGTCCCATCTC-3'(SEQ ID NO: 196) and the reverse primer used was 5'-CGTTCTCGGTTGGTGTTC-3'(SEQ ID NO: 197).

TABLE 1

Recombinant VEGFA Proteins for Aptamer Selections

| Protein | Vendor | Catalog Number |
|---|---|---|
| Human VEGF-121 | R&D systems | 4644-vs-CF |
| Human VEGF-121 (C-6His) | Novoprotein | C699 |
| Human VEGF-121 (N-6His) | ACROBiosystems | VE1-H5246 |
| Biotinylated Human VEGF-121 (Avitag ™) | ACROBiosystems | VE1-H82E7 |
| Human VEGF-121 | ProSpec | CYT-200 |
| Human VEGF-121 | Shenandoah Biotechnology | 100-116 |
| Human VEGF-165 | R&D systems | 293-VE-500 |
| Human VEGF-165 (N-6His) | ACROBiosystems | VE5-H5248 |
| Biotinylated Human VEGF-165 (Avitag ™) | ACROBiosystems | VE5-H82Q0 |
| Human VEGF-165 | Shenandoah Biotechnology | 100-44 |
| Mouse VEGF-120 | Shenandoah Biotechnology | 200-52 |
| Rat VEGF-164 | R&D systems | 564-RV/CF |
| Mouse VEGF-164 | Shenandoah Biotechnology | 200-34 |

The selection was started by synthesizing of a library of monoclonal modified aptamer particles (MAPs) each displaying multiple copies of fully 2'-fluoro modified aptamer candidate sequence on its surface. Then the emulsion was broken and the reverse strands were de-hybridized, leaving single strand 2'-fluoro modified aptamers (~90%) and natural DNA template sequences (~10%) on the particles, completing the formation of MAPs, which were now ready for screening. Like the template particles, MAPs are monoclonal wherein each particle displays ~$10^5$ copies of a single modified aptamer sequence and ~104 copies of amplifiable natural DNA sequences.

Then the MAPs were incubated with the one or more of the selection VEGF targets from Table 1 at 37° C. The MAPs were subsequently labeled using fluorescently labeled (Alexa Fluor 488 or 647) anti-VEGF antibody (for non-tagged VEGF), anti-His antibody (for His-tag VEGF), or streptavidin (for biotinylated VEGF). The fluorescence intensity of each MAP reflects the relative affinity of the 2'-fluoro modified aptamer for the VEGF target, which allows quantitatively isolating of aptamers with high affinity to target via a Fluorescence Activated Cell Sorter (FACS). To perform iterative rounds of CAPD to converge the pool on the best binders, PCR was used to amplify the natural DNA encoding strands on the enriched MAPS via high-fidelity polymerase and subsequent rounds of screening or sequencing were performed. Preferential selection of the anti-VEGF aptamers with higher affinity was achieved by shortening the incubation times, decreasing VEGF concentrations, and increasing the wash time in successive rounds. To avoid generating anti-VEGF aptamers that bind to VEGF mainly via the less specific polar interactions, increasing concentrations of polyanion competitors were introduced in successive rounds, such as salmon sperm DNA (Thermo Fisher Scientific, 15632011), herring sperm DNA (Sigma-Aldrich, D3159), and dextran sulfate (Sigma-Aldrich, 31404).

For ensuring binding specificity to the selection target, VEGF, increasing concentrations of non-target protein such as bovine serum albumin (BSA) or casein or non-target protein mixture such as diluted human serum (0%, 0.1%, 1% and 10%) can be introduced in the selections to ensure that the resulting anti-VEGF aptamers can specifically recognize VEGF with great affinity even when excessive amount (up to $10^9$ fold concentration compared to VEGF) of interfering proteins are present.

Methods of enriching slow off-rate anti-VEGF aptamers were also incorporated in some selections. To do so, the enriched high-affinity MAPs were incubated with saturating concentration of biotinylated VEGF (ACROBiosystems, VE1-H82E7 or VE5-H82Q0) targets, and subsequently washed with an excess amount of non-labeled VEGF (ACROBiosystems, VE1-H5246 or VE5-H5248) for increasing duration of time (from 1 minute to 24 hours) in successive rounds. The non-labeled VEGF could replace the biotinylated VEGF that dissociated from the MAPs, and would not exhibit any fluorescent signal after the MAPs were labeled with fluorescent streptavidin. MAPs displaying slower off-rate anti-VEGF aptamers can retain more biotinylated VEGF targets after the wash procedure and exhibit higher fluorescence intensities, which allows quantitatively isolate anti-VEGF aptamers for VEGF with slow off-rate via a Fluorescence Activated Cell Sorter (FACS).

For some selections against VEGF-165, an excess amount of heparin (Sigma-Aldrich H3393) was introduced as competitors in the selections to ensure preferential selection of anti-VEGF aptamers with a higher affinity towards the receptor-binding domain of VEGF-165 and avoid yielding anti-VEGF aptamers that target the heparin-binding domain of VEGF-165. In this way, the resulting anti-VEGF aptamers are likely to recognize both VEGF-165 and VEGF-121.

To generate anti-VEGF aptamers that can recognize both VEGF-121 and VEGF-165 with similarly high affinity, some selections were done by toggling the protein target between human VEGF-121 and human VEGF-165 during alternating rounds of selection. The "toggle" selection process yielded a family of anti-VEGF aptamers, all of which bound both VEGF-121 and VEGF-165 with high affinity. Species cross-reactivity facilitates the pre-clinical evaluation of potentially therapeutic anti-VEGF aptamers in animal models. In order to generate aptamers that bind both human VEGF and rat/mouse VEGF, some selections were also done by toggling the protein target between human VEGF-121 and mouse VEGF-120 (Shenandoah Biotechnology, 200-52) or rat VEGF 164 (R&D Systems, 564-RV/CF) during alternating rounds of selection.

To ensure the selected anti-VEGF aptamer can inhibit the interaction between VEGF and its receptor, some selections were done by exploiting the existing VEGF binders that recognize the receptor-binding domain of the VEGF antigen, such as Recombinant Human VEGF Receptor 2 (VEGFR2, R&D Systems, 357-KD-050), Recombinant Human VEGF Receptor 1 (VEGFR1, R&D Systems, 321-FL-050), ranibizumab (Lucentis®) or aflibercept (Eylea®). The existing VEGF binders were used as the competitors during Particle Display screen.

The selected aptamer pools were sequenced using Next Generation Sequencing using an Illumina MiSeq™ System and analyzed bioinformatically. Because these aptamers were generated using the advanced selection methods as described above, such as including polyanion and/or protein competitors, improving off-rate, toggling between VEGF-121 and VEGF-165, and the resulting aptamers can recognize both VEGF-121 and VEGF-165 with high affinity.

Example 2 Anti-VEGF Aptamer Identification and Truncation

Figure 1B:
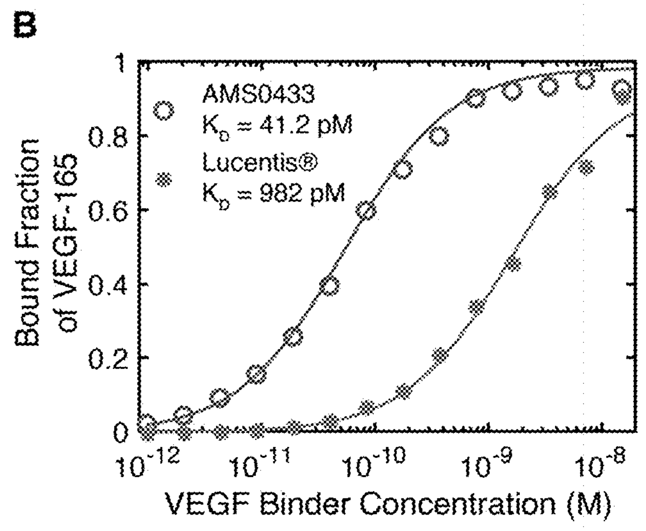

Truncated and modified variants of the anti-VEGF aptamers of the present disclosure were prepared by LGC Biosearch Technologies (Novato, CA), and their binding affinity to corresponding targets were examined. Briefly, the equilibrium binding constants of the enriched libraries were measured using magnetic bead partitioning. Biotinylated anti-VEGF aptamers were conjugated to the 1 μm streptavidin-coated MyOne Streptavidin C1 magnetic beads (Thermo Fisher Scientific, 65002). Binding assays were performed by incubating fixed concentration of anti-VEGF aptamer (0.01 nM) and target protein at concentrations ranging from $10^{-12}$ to $10^{-8}$ M in PBSMCT buffer (DPBS, pH 7.2 with 2.5 mM $MgCl_2$, 1 mM $CaCl_2$) and 0.01% TWEEN-20) at 37° C. for 90 minutes. Bound target protein was partitioned by magnetic separation and subsequently labeled via fluorescent anti-VEGF or anti-His-tag antibody. The fraction of anti-VEGF aptamer bound was quantified by flow cytometry (BD Accuri C6 Plus). Raw binding data were corrected for nonspecific background binding of target protein to empty magnetic beads. The fraction of bound anti-VEGF aptamer was plotted as a function of protein concentration and a non-linear curve-fitting algorithm (Langmuir one-site binding model) was used to extract equilibrium binding constants ($K_D$ values) from the data (FIGS. 1A-1B).

Truncated variants of representative anti-VEGF aptamer sequences of the present disclosure are shown in Table 2, with their $K_D$ values for VEGF-121 and VEGF-165 indicated.

TABLE 2

Mutations and Truncations of anti-VEGF aptamer AMS0433.0

| Aptamer ID | $K_D$ (nM) for VEGF-121 | $K_D$ (nM) for VEGF-165 |
|---|---|---|
| AMS0433.0 | 15.22 | 11.07 |
| AMS0433.1 | 1.125 | 0.666 |
| AMS0433.2 | 11.40 | 8.422 |
| AMS0433.3 | 0.921 | 0.837 |
| AMS0433.4 | 1.095 | 0.760 |
| AMS0433.5 | 1.191 | 0.739 |
| AMS0433.6 | 0.898 | 0.674 |

TABLE 2-continued

| Mutations and Truncations of anti-VEGF aptamer AMS0433.0 | | |
|---|---|---|
| Aptamer ID | $K_D$ (nM) for VEGF-121 | $K_D$ (nM) for VEGF-165 |
| AMS0433.7 | 13.75 | 9.760 |
| AMS0433.8 | 10.97 | 8.200 |
| AMS0433.9 | >100 | >100 |
| AMS0433.10 | 11.39 | 8.47 |
| AMS0433.11 | 23.24 | 16.40 |
| AMS0433.12 | >100 | >100 |
| AMS0433.13 | 9.473 | 8.301 |
| AMS0433 | 0.052 | 0.041 |
| AMS0433.15 | 9.002 | 7.339 |
| AMS0433.16 | 10.45 | 6.648 |
| AMS0433.17 | 0.475 | 0.359 |
| AMS0433.18 | 5.731 | 3.806 |
| AMS0433.19 | 0.162 | 0.097 |
| AMS0433.20 | 0.045 | 0.039 |
| AMS0433.21 | 0.150 | 0.131 |

Compared to the only FDA-approved aptamer-based anti-VEGF therapeutic (Macugen®) that binds only to VEGF-165, the anti-VEGF aptamers of the present disclosure bind to both human VEGF-121 and human VEGF-165 with comparable and superior affinities of ~50 pM (FIGS. 1A-1B). Compared to the FDA-approved protein-based anti-VEGF therapeutic (Lucentis®) that binds to both VEGF-121 and VEGF-165 with similar affinities, the anti-VEGF aptamers of the present disclosure showed more than 10-fold improvement of binding affinity.

Figure 2:
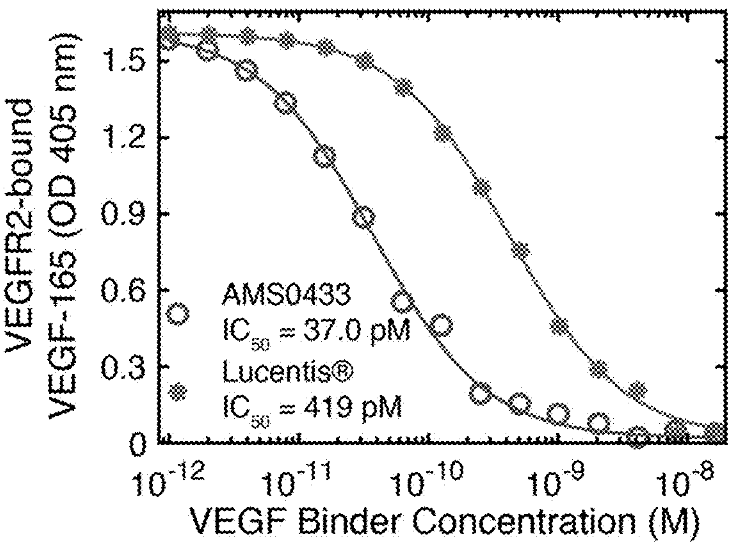
FIG. 2 illustrates in vitro VEGF receptor competitions assays for the anti-VEGF aptamers of the present disclosure.

Example 3 Anti-VEGF Aptamer In Vitro VEGF-R Competition Assays and Secondary Structure Prediction To demonstrate that the anti-VEGF aptamer of the present disclosure is a potent inhibitor of vascular endothelial growth factor-A (VEGF) signaling, in vitro VEGF receptor competition ELISA assays was performed to verify that the anti-VEGF aptamers can potently block the interaction between VEGF-A and VEGF receptors and their performance to FDA-approved protein-based drug ranibizumab (Lucentis®) was compared. Briefly, AMS0433 (as an example of the anti-VEGF aptamer of the present disclosure) or Lucentis at concentrations ranging from $10^{-12}$ to $10^{-8}$ M in PBSMCT buffer (DPBS, pH 7.2 with 2.5 mM $MgCl_2$, 1 mM $CaCl_2$) and 0.01% TWEEN-20) were mixed together with 50 pM of human VEGF-165 (R&D Systems, 293-VE-050) and transferred to human VEGFR2 Receptor (R&D Systems, 357-KD-050) immobilized plate and incubated for 1 hour at 37° C. After washing, the VEGFR2 captured VEGF-165 was detected by 1 pg/ml anti-VEGF antibody (R&D Systems, AF-293-NA) and horseradish peroxidase (HRP)-conjugated anti-goatIgG, followed by TMB substrate. The VEGFR2-bound VEGF was quantified by measuring the optical density (OD) at 405 nm using a Biotek Synergy H1 Hybrid Multi-Mode Reader. Raw data were normalized to the absorbance signal from the sample with 50 pM of VEGF-165 but without aptamer competition (0 nM aptamer). The VEGFR2-bound VEGF was plotted as a function of aptamer concentration and a non-linear curve-fitting algorithm (dose-response inhibition) was used to extract $IC_{50}$ values from the data (FIG. 2).

It can be seen that the anti-VEGF aptamer of the present disclosure could potently inhibit the interaction between VEGF-A and VEGFR2 with an $IC_{50}$ values around 50 pM (FIG. 2), demonstrating that the anti-VEGF aptamers bind to and block the receptor-binding domain on VEGF and shows about 10-fold improvement of potency compared to FDA-approved protein-based anti-VEGF therapeutic (Lucentis®). The exemplary potency of the anti-VEGF aptamers of the present disclosure, measured by VEGFR2 Receptor blocking assay, is listed in Table 3.

TABLE 3

| In vitro potency of the anti-VEGF aptamers | |
|---|---|
| Aptamer ID | VEGFR2 $IC_{50}$ (nM) |
| AMS0433.0 | 27.46 |
| AMS0433.1 | 1.729 |
| AMS0433.2 | 9.262 |
| AMS0433.3 | 2.099 |
| AMS0433.4 | 1.959 |
| AMS0433.5 | 2.499 |
| AMS0433.6 | 3.494 |
| AMS0433.7 | 8.231 |
| AMS0433.8 | 42.94 |
| AMS0433.9 | >100 |
| AMS0433.10 | 27.17 |
| AMS0433.11 | 29.53 |
| AMS0433.12 | >100 |
| AMS0433.13 | 12.28 |
| AMS0433 | 0.037 |
| AMS0433.15 | 2.165 |
| AMS0433.16 | 1.195 |
| AMS0433.17 | 0.983 |
| AMS0433.18 | 8.34 |
| AMS0433.19 | 0.056 |
| AMS0433.20 | 0.044 |
| AMS0433.21 | 0.064 |
| AMS0433.m4 | 0.040 |
| AMS0433.m6 | 0.041 |

Figure 5A:
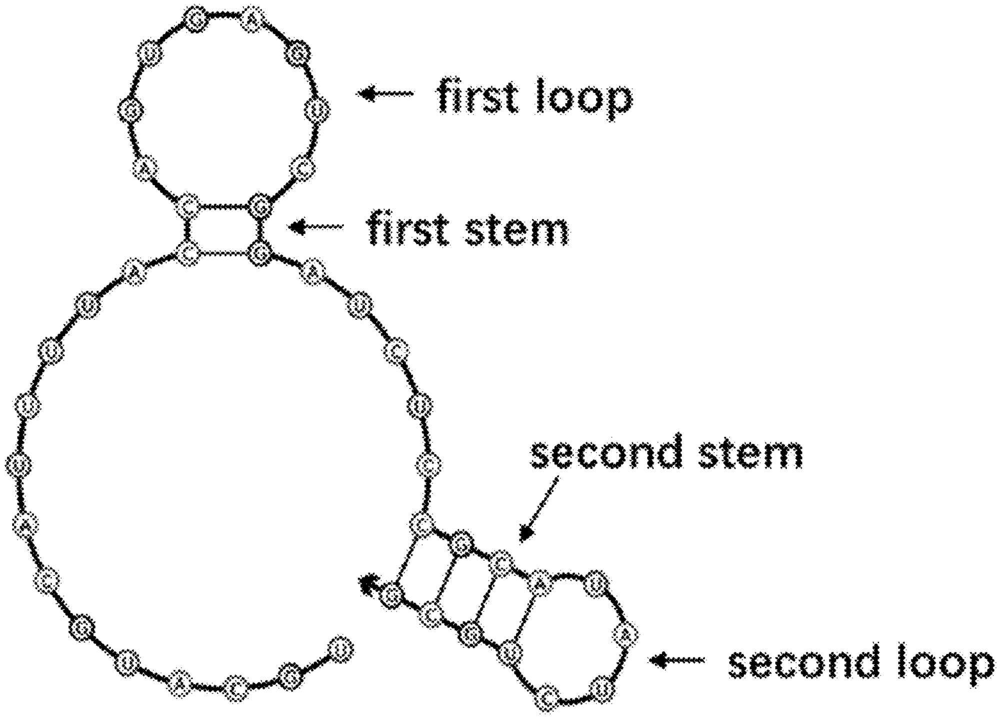
FIGS. 5A-5C illustrate the secondary structures of the anti-VEGF aptamers, the anti-Ang2 aptamers, and the bispecific aptamers of the present disclosure.

In addition, 2-dimensional structures analysis for the selected anti-VEGF aptamers was performed using the NUPACK software suite. The results are illustrated in FIG. 5A for AMS0433.

Further, it is demonstrated that substituting several 2'-F nucleotides to 2'-Ome nucleotides doesn't compromise performance. One key advantage of the aptamers of present application is their flexibility to various chemical substitution or modifications. Such modifications can be readily achieved during the chemical synthesis process. For example, the VEGF aptamer AMS0433 (having a nucleotide acid sequence as set forth in SEQ ID No.128) and 2 additional variants (AMS0433.m4 and AMS0433.m6, having a nucleotide acid sequence as set forth in SEQ ID No.200 or SEQ ID No.201, respectively), each of which containing multiple 2'-Ome-modified nucleotides in place of the previous 2'-fluoro-modified nucleotides. Both variants displayed similar potency to AMS0433 in the in vitro VEGF-R competition assay (Table 3), and may possess additional benefits compared to AMS0433, such as better manufacturability.

Example 4 Anti-VEGF Aptamer In Vivo Efficacy Test in Non-Human Primate (NHP) Laser-Induced CNV Model The study was performed by largely following previously established procedure. Adult cynomolgus monkeys (2-4 kg) were used for the study. Monkeys were anesthetized with ketamine hydrochloride (10 mg/kg, intramuscular injection) and sodium pentobarbital (12 mg/kg, intravenous injection), pupils were dilated, and CNV was induced in the monkeys by laser rupture of the Bruch's membrane around the macula (6-8 burns per eye. Laser setting: 532 nm wavelength, 400-500 mW, 50 m diameter, 100 ms duration). Only the laser spots where a bubble was formed without hemorrhage were considered effective CNV lesions and included in the study. Two weeks after the laser treatment, fluorescein angiography (FA) was performed to visualize the CNV lesions: 100 mg/ml sodium fluorescein was injected at 10 mg/kg of body weight; following the injection, a rapid series of images were taken in the first minute (early-phase images) and after 5 minutes (late-phase images). The leakage of each lesion was visualized by comparing the late-phase images against the early-phase images, and the leakage severity was scored according to a scale of Grade I to IV: Grade I—no hyperfluorescence; Grade II—hyperfluorescence without leakage; Grade III—hyperfluorescence in the early or mid-transit images and late leakage; Grade IV—bright hyperfluorescence in the transit and late leakage beyond the treated areas. Grade IV lesions are considered as clinically significant. Optical coherence tomography (OCT) was also performed to measure the height of the subretinal hyperreflective material (SHRM) at the laser burns, which is analogous to human pathologic CNV. The following agents were then administered via intravitreal injection on the same day: Group 1: 50 μl of AMS0433; Group 2: 50 μl of a negative control aptamer. The CNV lesions were measured again at 1 and 2 weeks after test article injection following the procedure described above, and the effect of the aptamer was measured by comparing the leakage area of the Grade IV lesions before and after injection. Moreover, OCT was also performed and the height of the SHRM before and after injection was compared.

Figure 7A:
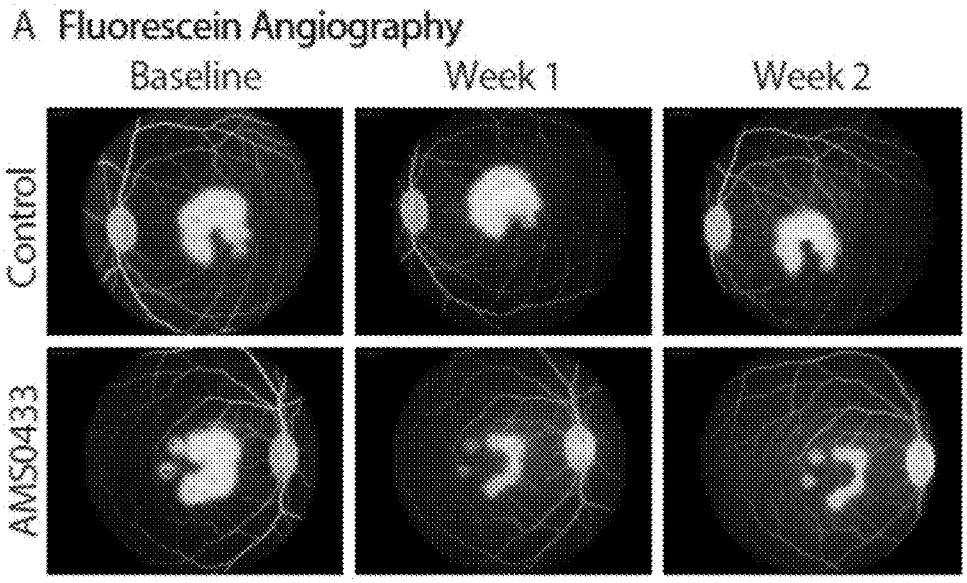
FIGS. 7A-7B illustrate the result of anti-VEGF aptamers of the present disclosure in the in vivo efficacy test in non-human primate (NHP) laser-induced CNV model.
Figure 7B:
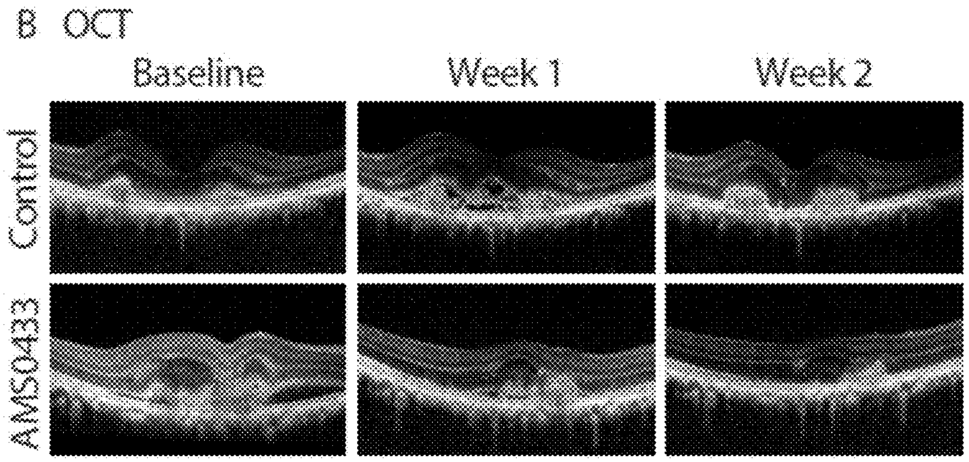

The results are shown in FIG. 7. The negative control aptamer displayed little effect on both SHRM thickness and leakage area as expected. In contrast, the injection of the anti-VEGF aptamer of the present disclosure (e.g., AMS0433) resulted in a dramatic reduction in both SHRM thickness and leakage area, as well as a complete regression of Grade IV lesions, confirming its potent efficacy in inhibiting CNV in NHPs.

Interestingly, Macugen® was also tested in this model, but having been reported to have no effect in inhibiting CNV, likely due to the fact that it does not inhibit some of the VEGF isoforms such as VEGF-121 (please refer to R. T. Tzekov et al., Evaluation of intravitreal application of Pegaptanib Sodium on Laser-induced CNV in Cynomolgus Monkeys, ARVO Annual Meeting Abstract, May 2006). However, the aptamers of the present disclosure exhibited potent efficacy in this model.

Example 5 Anti-Ang2 Aptamer Selection

The selection method is similar to that of Example 1.

Briefly, recombinant human Angiopoietin-2 protein (R&D Systems, 623-AN) was used as the target protein for anti-Ang2 aptamer discovery. A typical initial selection library contains a 40 nucleotide random region in which all nucleotides containing a 2'-fluoro (2'-F) modification. The forward primer was 5'-ATCCAGAGTGACG-CTCTTCAGCA-3'(SEQ ID NO: 198) and the reverse primer was 5'-TGAAGAGCGTCACTCTGGAT-3'(SEQ ID NO: 199). The following example describes the selection and production process of an aptamer that specifically binds recombinant human Ang2.

Each selection was started by synthesizing of a library of monoclonal modified aptamer particles (MAPs) each displaying multiple copies of fully 2'-fluoro modified aptamer candidate sequence on its surface. Then the MAPs were incubated with the Ang2 targets at 37° C. The MAPs were subsequently labeled using fluorescently labeled (Alexa Fluor 488 or 647) anti-Ang2 antibody or anti-His antibody (for His-tag Ang2), or streptavidin (for biotinylated Ang2). The fluorescence intensity of each MAP reflects the relative affinity of the 2'-fluoro modified aptamer for the Ang2 target, which allows quantitatively isolating aptamers with high affinity to target via a Fluorescence Activated Cell Sorter (FACS). To perform iterative rounds of CAPD to converge the pool on the best binders, PCR was conducted to amplify the natural DNA encoding strands on the enriched MAPs via high-fidelity polymerase and perform subsequent rounds of screening or sequencing. Preferential selection of anti-Ang2 aptamers with higher affinity was achieved by shortening the incubation times, decreasing Ang2 concentrations, and increasing the wash time in successive rounds. To avoid generating anti-Ang2 aptamers that bind to Ang2 mainly via the less specific polar interactions, increasing concentrations of polyanion competitors were introduced in successive rounds, such as salmon sperm DNA (Thermo Fisher Scientific, 15632011), herring sperm DNA (Sigma-Aldrich, D3159), and dextran sulfate (Sigma-Aldrich, 31404).

During some selections, advanced techniques were adopted to ensure the exquisite binding specificity requirement for the anti-Ang2 aptamer—an ideal anti-Ang2 aptamer should not bind to its homolog, Ang1, which plays the opposite role of Ang2. For example, increasing concentrations of non-target protein such as bovine serum albumin (BSA) or casein or Ang1 (R&D Systems, 923-AN) or non-target protein mixture such as diluted human serum (0%, 0.10%, 10% and 10%) can be introduced in the selections to ensure that the resulting anti-Ang2 aptamers can specifically recognize Ang2 with great affinity even when excessive amount (up to $10^9$-fold concentration compared to Ang2) of interfering proteins are present.

Methods of enriching slow off-rate anti-Ang2 aptamers were also incorporated in some selections. To do so, the enriched high-affinity MAPs were incubated with saturating concentration of biotinylated Ang2 targets, and subsequently wash with excessive amount of non-labeled Ang2 for increasing duration of time (from 1 minute to 24 hours) in successive rounds. The non-labeled Ang2 could replace the biotinylated Ang2 that dissociated from the MAPs, and would not exhibit any fluorescent signal after the MAPs were labeled with fluorescent streptavidin. MAPs displaying slower off-rate aptamers can retain more biotinylated Ang2 targets after the wash procedure and exhibit higher fluorescence intensities, which lets us quantitatively isolate anti-Ang2 aptamers for Ang2 with slow off-rate via a Fluorescence Activated Cell Sorter (FACS).

Species cross-reactivity facilitates the pre-clinical evaluation of potentially therapeutic anti-Ang2 aptamers in animal models. In order to generate anti-Ang2 aptamers that bind both human Ang2 and mouse Ang2, some selections were also done by toggling the protein target between human Ang2 and mouse Ang2 (R&D Systems, 7186-AN) during alternating rounds of selection. The toggle selection process yielded a family of anti-Ang2 aptamers, all of which bound human and mouse Ang2 with high affinity.

Example 6 Anti-Ang2 Aptamer Identification and Truncation, and Binding Affinity Assays Various mutations and truncated variants of a representative anti-Ang2 aptamer (AMS0525) were obtained and their binding affinity to Ang2 were measured using magnetic bead partitioning. Biotinylated anti-Ang2 aptamers were conjugated to the 1 m streptavidin-coated MyOne Streptavidin C1 magnetic beads (Thermo Fisher Scientific, 65002).

Figure 3A:
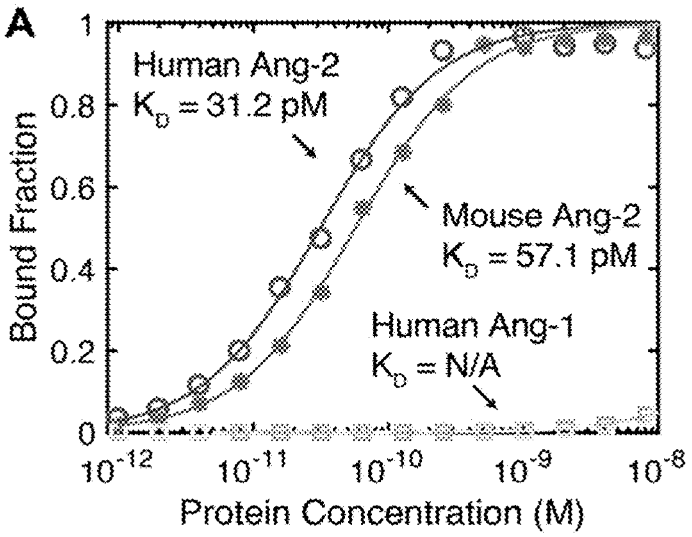
FIG. 3A illustrates binding affinity of the anti-Ang2 aptamers of the present disclosure.

Binding assays were performed by incubating fixed concentration of aptamer (0.01 nM) and Ang2 protein at concentrations ranging from $10^{-12}$ to $10^{-8}$M in PBSMCT buffer (DPBS, pH 7.2 with 2.5 mM $MgCl_2$, 1 mM $CaCl_2$) and 0.01% TWEEN-20) at 37° C. for 90 minutes. Bound target protein was partitioned by magnetic separation and subsequently labeled via fluorescent anti-His-tag antibody. The fraction of anti-Ang2 aptamer bound was quantified by flow cytometry (BD Accuri C6 Plus). Raw binding data were corrected for nonspecific background binding of target protein to empty magnetic beads. The fraction of bound anti-Ang2 aptamer was plotted as a function of protein concentration and a non-linear curve-fitting algorithm (Langmuir one-site binding model) was used to extract equilibrium binding constants ($K_D$ values) from the data (FIG. 3A).

The obtained $K_D$ values for Ang2 were shown in Table 4. AMS0525 has been truncated to a 48-mer (AMS0526) in a series of mutation and deletion experiments. Compared to previously reported partially-modified anti-Ang2 aptamer that binds to human Ang2 with $K_D$ of 3.1 nM, AMS0526 is a fully modified aptamer that binds to both human and mouse Ang2 with superior affinities ($K_D$<100 pM), and does not recognize human Ang1 (FIG. 3A).

TABLE 4

Variants of anti-Ang2 Aptamer AMS0525

| Aptamer ID | $K_D$ (nM) for Ang2 |
|---|---|
| AMS0525 | 0.404 |
| AMS0526 | 0.032 |
| AMS0525.3 | 0.033 |
| AMS0525.4 | >1 |
| AMS0525.5 | 0.043 |
| AMS0525.6 | 0.029 |
| AMS0525.7 | 0.093 |
| AMS0525.8 | 0.085 |

Interestingly, it was noted that replacing the 2'F modified nucleotides to corresponding nucleotides modified with 2'OMe or LNA did not significantly affect the binding of the resulted anti-Ang2 aptamers to the target Ang2 (as demonstrated by the $K_D$ values of AMS0525.5 and AMS0525.6).

Figure 5B:
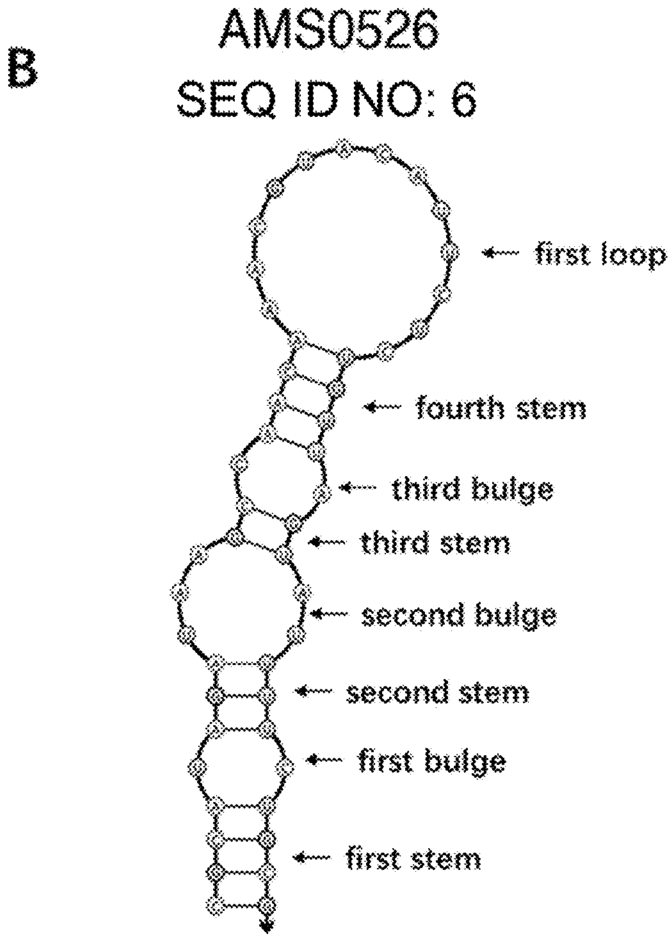

In addition, 2-dimensional structure analysis for the anti-Ang2 aptamer AMS0526 was performed using the NUPACK software suite, and the predicted structure is shown in FIG. 5B.

Example 7 Anti-Ang2 Aptamer In Vitro Tie2 Receptor Competition Assays

Figure 3B:
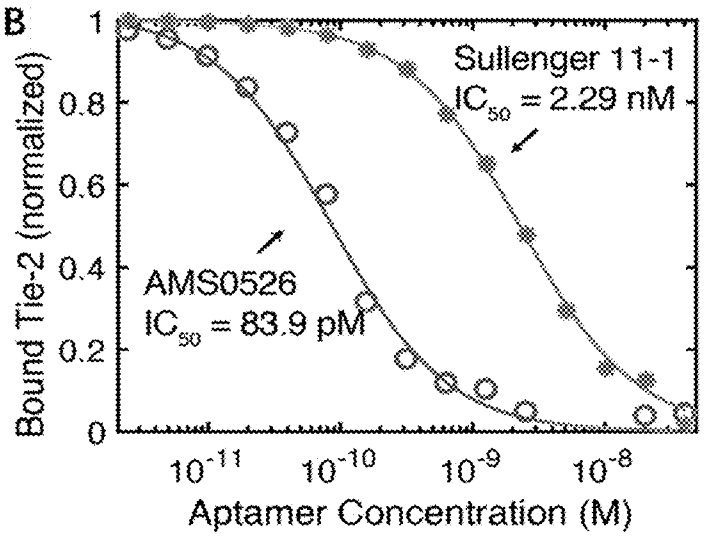
FIG. 3B illustrates the inhibition of binding of human Ang2 and Tie2 by the anti-Ang2 aptamers of the present disclosure.
Figure 4A:
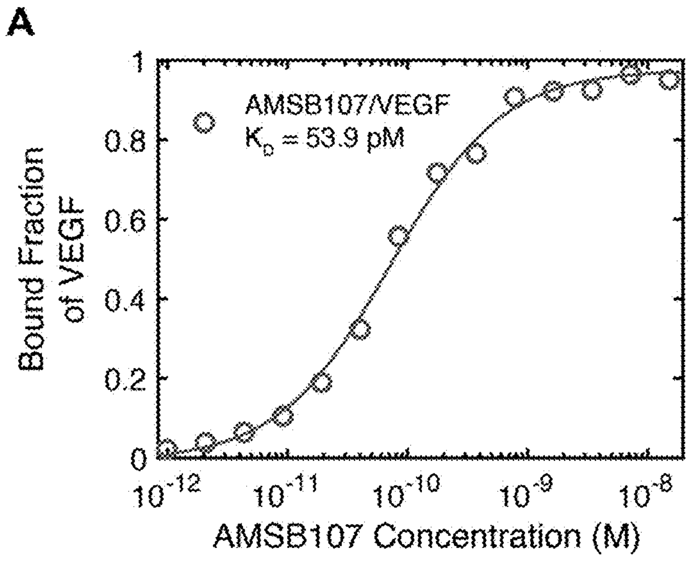
FIGS. 4A-4B illustrate binding affinity to VEGF and Ang2 for the bispecific aptamers of the present disclosure.
Figure 4B:
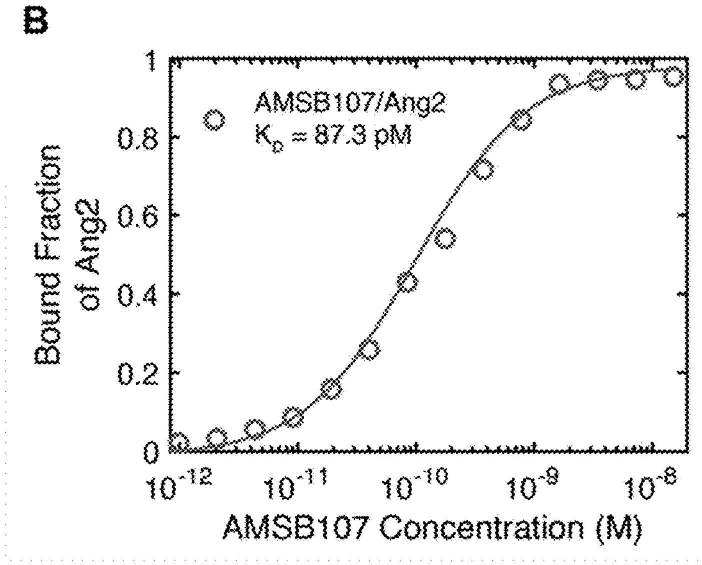
Figure 4C:
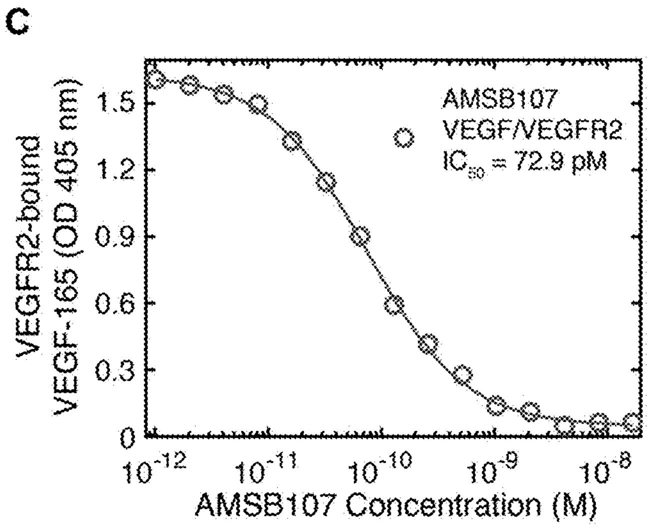
FIGS. 4C-4D illustrate in vitro VEGF and Ang2 receptor competition assays for the bispecific aptamers of the present disclosure.
Figure 4D:
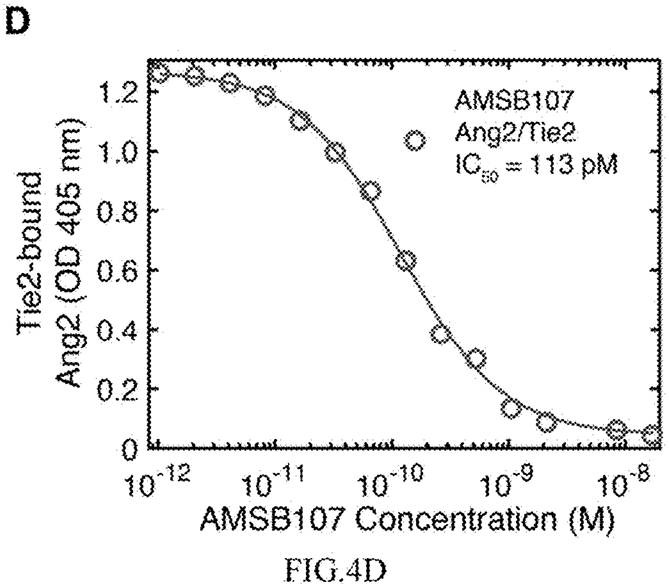

To demonstrate that the anti-Ang2 aptamer of the present disclosure are potent inhibitors of Ang2 signaling, in vitro competition assays was performed to verify that selected anti-Ang2 aptamers can block the interaction between Ang2 and Tie-2. For determination of the receptor competition $IC_{50}$, 0.01 nM of Ang2 with His tag was conjugated to Dynabeads His-Tag Isolation and Pulldown beads (Thermo Fisher Scientific, 10104D), and then incubated with 1 nM of Tie2 (R&D Systems, 313-TI) and anti-Ang2 aptamers at concentrations ranging from $10^{-12}$ to $10^{-8}$ M in PBSMCT buffer (DPBS, pH 7.2 with 2.5 mM $MgCl_2$, 1 mM $CaCl_2$) and 0.01% TWEEN-20) at 37° C. for 90 minutes. Ang2-bound Tie2 and anti-Ang2 aptamers were partitioned by magnetic separation, and the Ang2-bound Tie2 were subsequently labeled via a fluorescent anti-human antibody. The fraction of Ang2-bound receptor was quantified by flow cytometry (BD Accuri C6 Plus). Raw binding data were corrected for nonspecific background binding and normalized to the fluorescence intensity from the sample with 1 nM Tie2 but without anti-Ang2 aptamer competition. The fraction of bound receptor was plotted as a function of anti-Ang2 aptamer concentration and a non-linear curve-fitting algorithm (dose-response inhibition) was used to extract $IC_{50}$ values from the data (FIG. 3B). It can be seen that AMS0526 could potently inhibit the interaction between Ang2 and Tie2 with $IC_{50}$ of 83.9 pM, which is 30-fold better compared to the previously reported anti-Ang2 aptamer (FIG. 3B).

Example 8 Anti-Ang2 Aptamer In Vivo Efficacy Test in Oxygen-Induced Retinopathy (OIR) Model The study was performed by largely following previously established procedure to test the effect on both angiogenesis and vascular permeability. OIR was induced by placing litters of C57BL/6 mice in 75% 02 on postnatal day 7 (P7). On P12, the mice were returned to room air. To test the effect on angiogenesis, the mice received intravitreal injections on the same day with the following agents: Group 1 (G1): PBS (negative control); G2: 20 μg of Aflibercept; G3: 20 μg of AMS0525; G4: 20 μg of Aflibercept+20 μg of AMS0525. On P17, the mice were sacrificed, fixed in 10% phosphate-buffered formalin for 4 hours at 22° C., the eyes of the mice were dissected and retina flat mounts were prepared. The retina was then stained with FITC-labeled *Griffonia simplicifolia* (GSA) lectin (Vector Laboratories) for 45 min to visualize NV. Digital photographs were obtained with a Zeiss fluorescent microscope at 5× magnification, and images were merged into a single image to show the entire retina using photomerge option of Photoshop CS5.4. The area of retinal NV was measured by Image-Pro Plus (Media Cybernetics) by a separate researcher blinded with respect to sample identity. To test the effect on vascular permeability, OIR was induced via the same procedure as described above, but mice received the injection on P16-when the neovascularization (NV) was already developed. This way, only the drug effect on vascular permeability was tested, not NV growth. On P17, vitreous samples from the mice was obtained and the amount of albumin leaked from the blood vessels was measured by ELISA.

Figure 6A:
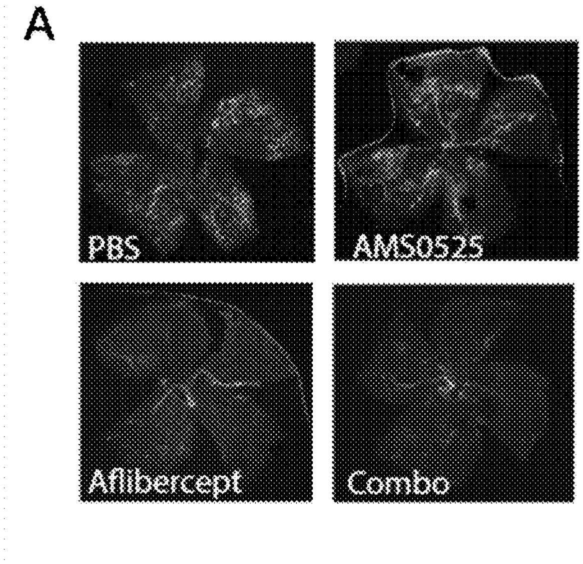
FIGS. 6A-6C illustrate the effect of the anti-Ang2 aptamers of the present disclosure on neovascularization and vascular permeability.
Figure 6B:
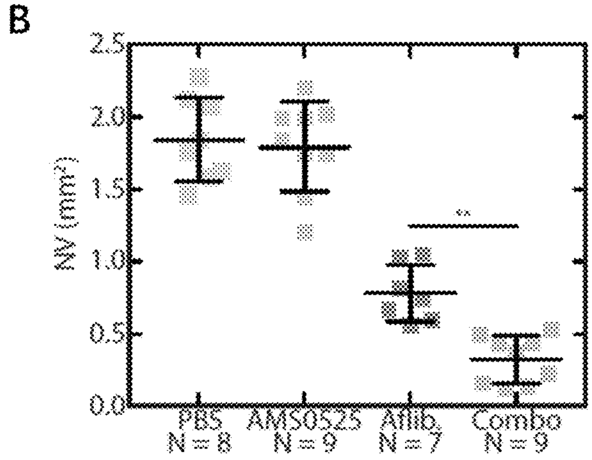
Figure 6C:
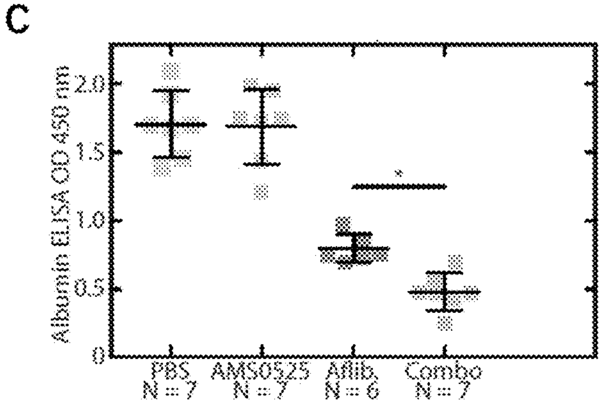

The results are shown in FIG. 6. While inhibiting Ang2 alone has very modest effect (consistent with previous studies), combining the anti-Ang2 aptamer of the present disclosure with Aflibercept almost completely eliminated NV, resulting in significantly better efficacy than Aflibercept alone (FIG. 6). As shown in FIG. 6, despite the established NV, the combination of the anti-Ang2 aptamer of the present disclosure and Aflibercept reduced leakage to a superior extent over Aflibercept alone.

Example 9 Obtaining Bispecific Aptamers

With the aim of developing a bispecific aptamer that can recognize both VEGF and Ang2 simultaneously, a variety of aptamer constructs comprising an anti-VEGF aptamer (AMS0433 or its derivatives from Table 2) linked to an anti-Ang2 aptamer AMS0526 (shown in Table 4) were prepared and tested. Bispecific aptamer constructs were synthesized head-to-tail, connected directly without any linker, in both orientations, either with the anti-VEGF aptamer at the 5' end (AMSB107.0) or with the anti-Ang2 aptamer at the 5' end (AMSB108.0). The results are summarized in Table 5.

TABLE 5

| Binding affinity of the bispecific aptamers | | |
|---|---|---|
| Aptamer ID | KD (nm) for VEGF-165 | KD (nm) for Ang2 |
| AMSB107.0 | 1.286 | 0.222 |
| AMSB108.0 | 15.67 | 0.520 |

Based on binding affinity for VEGF and Ang2, bispecific aptamer A70SB107.0 appeared to give the best results and was chosen for further truncation and mutation experiments. VEGF/Ang2 bispecific aptamer AMSB107 showed $K_D$ and $IC_{50}$ for VEGF and Ang2 that was equivalent or better than the binding affinity of its precursor aptamers (Table 6). Based on the functional receptor inhibition assay results, A2SB107 inhibited both the VEGF/VEGFR2 and the Ang2/Tie2 interactions with $IC_{50}$ values of ~100 pM (FIG. 4).

TABLE 6

| Binding affinity and in vitro function of the bispecific aptamers | | | |
|---|---|---|---|
| Aptamer ID | KD (nM) for VEGF-165 | KD (nM) for Ang2 | VEGF $IC_{50}$ (nM) |
| AMSB107.1 | 13.94 | 0.885 | 21.49 |
| AMSB107.2 | 12.87 | 0.820 | 19.43 |
| AMSB107 | 0.054 | 0.087 | 0.073 |
| AMSB107.4 | 0.225 | 0.237 | 0.081 |
| AMSB107.5 | 0.052 | 0.096 | 0.081 |
| AMSB107.6 | 2.336 | 0.074 | 0.551 |
| AMSB107.7 | >100 | 0.085 | >100 |
| AMSB107.8 | 0.048 | 0.095 | 0.255 |
| AMSB107.9 | 0.151 | 0.150 | 0.147 |
| AMSB107.10 | 0.051 | 0.089 | 0.170 |
| AMSB107.11 | 0.057 | 0.095 | 0.114 |
| AMSB107.12 | 0.606 | 0.227 | 1.034 |
| AMSB107.13 | 0.050 | 0.089 | 1.000 |
| AMSB107.14 | 0.643 | 0.928 | 3.271 |
| AMSB107.15 | 0.765 | 0.778 | 15.59 |
| AMSB107.16 | >100 | 0.080 | >100 |
| AMSB107.17 | 0.198 | 0.086 | 0.083 |
| AMSB107.18 | 0.608 | 0.079 | 0.422 |
| AMSB107.19 | >100 | 0.083 | >100 |
| AMSB107.20 | 0.234 | 0.253 | 0.068 |
| AMSB107.21 | 0.052 | 0.083 | 0.063 |
| AMSB107.22 | 0.055 | 0.098 | 0.044 |
| AMSB107.23 | 0.049 | 0.084 | 0.040 |
| AMSB107.24 | 0.209 | 1.782 | 0.067 |
| AMSB107.25 | 0.224 | 1.407 | 0.061 |
| AMSB107.26 | 0.056 | 0.076 | 0.044 |
| AMSB107.27 | 0.059 | 0.079 | 0.037 |

Figure 5C:
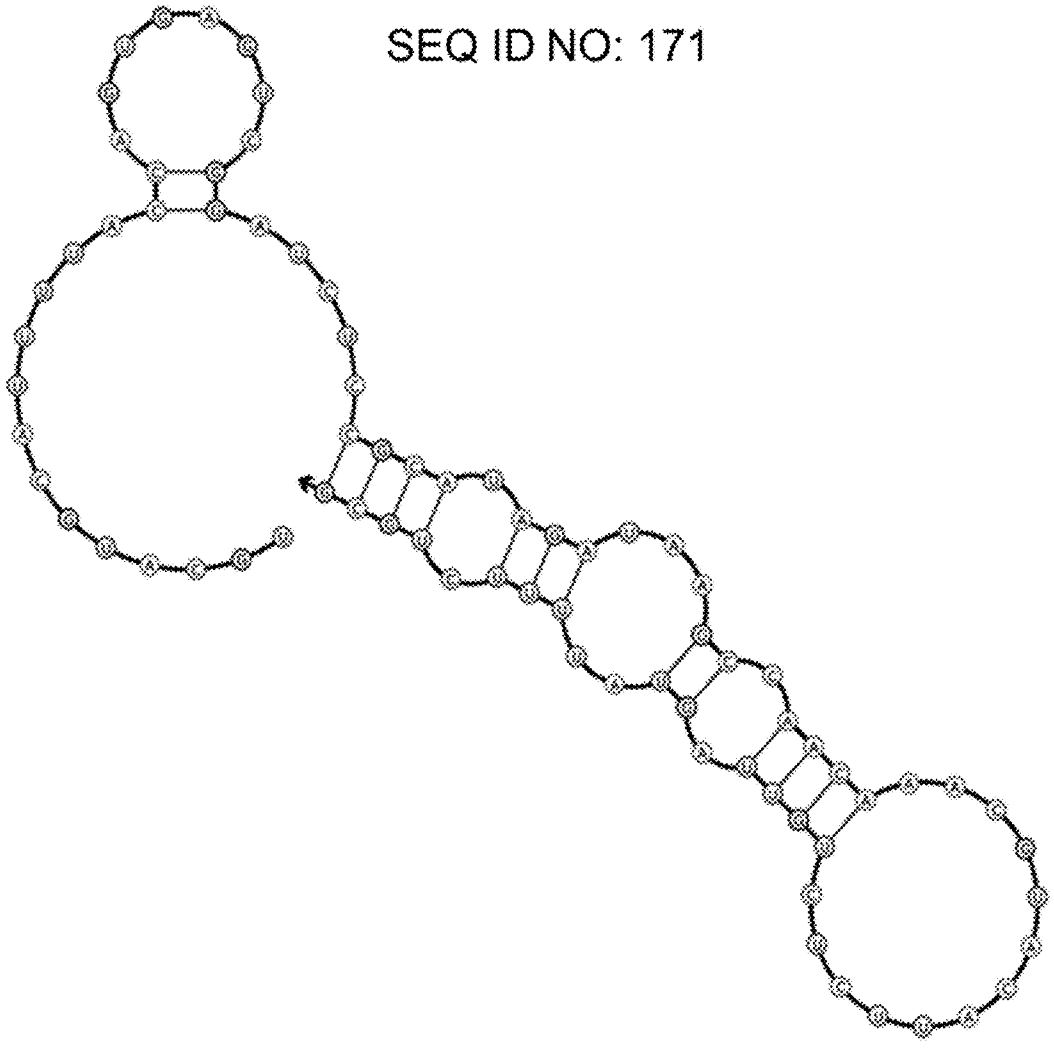

The predicted secondary structures of the anti-VEGF aptamer AMS0433, the anti-Ang2 aptamer AMS0526 and the anti-VEGF/anti-Ang2 bispecific aptamer AMSB107 were shown in FIG. 5. When designing AMSB107, the 3' bottom stem region of both anti-VEGF aptamer AMS0433 and anti-Ang2 aptamer AMS0526 were carefully selected and shared in order to minimize chance of misfolding and interference between the two individual aptamers (FIG. 5). As a result, the structures of both the anti-VEGF aptamer AMS0433 and the anti-Ang2 aptamer AMS0526 were well retained in the bispecific construct AMSB107.

TABLE 7

| Binding affinity and in vitro function of the bispecific aptamers | | |
|---|---|---|
| Aptamer ID | VEGF $IC_{50}$ (nM) | Tier2 $IC_{50}$ (nM) |
| AMSB107.P6 | 0.039 | 0.035 |
| AMSB107.P40K | 0.036 | 0.045 |

Further, it is demonstrated that adding a linker or a PEG polymer doesn't compromise performance. Another key advantage of aptamers of present application is their modularity—linkers such as a hexaethylene glycol linker (H or PEG6) can be added during chemical synthesis between different binding motifs, and large polymers such as high-molecular-weight polyethylene glycol (PEG) can be conjugated to the end of aptamer without affecting the performance of the aptamer. For example, the VEGF aptamer AMSB107 (having a nucleotide acid sequence as set forth in SEQ ID No.171) and 2 additional variants (AMSB107.P6 and AMSB107.P40K, having a nucleotide acid sequence as set forth in SEQ ID No.202 or SEQ ID No.203, respectively), displayed similar potency in the in vitro receptor competition assay for both VEGF and Ang2. Such variants may possess additional benefits compared to AMSB107, such as tunable spacing, lower manufacturability cost, and better in vivo pharmacokinetics. The AMSB107.P6 uses a H linker to replace several nucleotides in AMSB107—the H linker can be incorporated during the chemical synthesis of the aptamer using well-known procedure. The AMSB107.P40K uses a 40 kDa PEG to conjugate to the 5'-end of AMSB107 using well-known amino-based chemical conjugation chemistry.

Pegylation and Purification Procedure:

Aptamers with 5'-amino-modified C6 linker (Glen-research, 10-1906-02M) were synthesized using Trityl-on process and purified via Glen-pak purification cartridge (Glen-research, 60-5100-96) to de-trityl and remove the short-failed synthesis products. Desalted aptamers were then concentrated using spin concentrator (Millipore, UFC901024). 1 mM 5'-amino-modified aptamers were mixed with 1.5 mM to 2 mM 40 kDa Y-shape NHS Ester modified PEG (JenKem Technology USA Inc, Y-NHS-40K) with 50% DMSO and 50 mM Teorell and Stenhagen buffer at pH8.2. The reaction mix was mixed thoroughly and incubated at 37° C. for 1 hr. The reaction mix was analyzed using DNAPac PA100 analytical column (Thermofisher, 043010) on Agilent 1260 HPLC system. The formation of the pegylated aptamer was confirmed by the appearance of a corresponding elution peak distinct from the non-pegylated aptamer. The PEGylated aptamer was then purified using TSKgel SuperQ-5PW anion exchange resin (Tosoh Bioscience, 0043383) on an AKTA Explorer FPLC System. PEGylated aptamer was then desalted using ultrafiltration, lyophilized and stored at −20° C.

The binding affinity of the aptamer of the present application to Tie2 was measured using the method similar to that of measuring the binding affinity of the aptamer of the present application to VEGF.

Example 10 Pegylated Bispecific Aptamer Achieves Higher Potency and Longer Duration of Effect than Aflibercept in Rabbit DL-a-Aminoadipic Acid (DL-AAA) Induced Retinal NV Model AMSB107P (having a nucleotide acid sequence as set forth in SEQ ID No.204), which is a fully-modified bispecific aptamer containing both 2'-fluoro-modified nucleotides and 2'-Ome-modified nucleotides was constructed, and is conjugated to a 40 kDa PEG at 5'-end using amino-NHS conjugation chemistry as described for AMSB107.P40K. It is hypothesized that the pegylated aptamer will possess a higher half-life than biologics; moreover, the VEGF/Ang2 dual-targeting mechanism may also enable better efficacy and longer duration in vivo. And this hypothesis was tested in a rabbit DL-a-aminoadipic acid (DL-AAA) induced retinal NV model.

The study was performed by adapting the previously established procedure (refer to J. Cao, T. C. MacPherson, B. V. Iglesias, Y. Liu, N. Tirko, G. D. Yancopoulos, S. J. Wiegand, C. Romano, Aflibercept Action in a Rabbit Model of Chronic Retinal Neovascularization: Reversible Inhibition of Pathologic Leakage With Dose-Dependent Duration, Investig. Opthalmology Vis. Sci. 59, 1033 (2018)). New Zealand white (NZW) rabbits of 2-4 months of age (~6 lbs) were used in this study. Rabbits were allowed 1 week to acclimatize upon their arrival at the facility. To induce retinal NV and leakage, rabbits were anesthetized with 8 mg/kg Zoletil™ 50 and 1.6 mg/kg xylazine via intramuscular injection, and received intravitreal injections in both eyes of 80 1 of freshly prepared 80 mM solution of DL-a-aminoadipic acid (DL-AAA) to induce retinal vascular leakage. The injection site was treated with antibiotic ointment using a cotton-tipped applicator after the injection. Rabbits were then maintained for at least 10 weeks to allow the NV and leakage to stabilize.

Next, rabbits with stabilized leakage received intravitreal injections of the following test articles: Group 1: 50 µl of 10 mg/ml Aflibercept; Group 2: 50 µl of 10 mg/ml AMSB107P. Efficacy of leakage suppression and NV regression was measured using the Spectralis HRA+OCT system (Heidelberg). For measuring the effect of leakage suppression, the rabbits were injected in the marginal ear vein with 10% sodium fluorescein (10 mg/kg) for fluorescein angiography (FA) imaging; red-free imaging was used to visualize the retinal NV. FA and red-free imaging were performed on one day before injection (as baseline), and also weekly after the injection.

The safety of the test articles was evaluated by weekly slit lamp biomicroscopy.

It is found that AMSB107P was well tolerated, and no test article-related toxicity was reported throughout the study.

Figure 8:
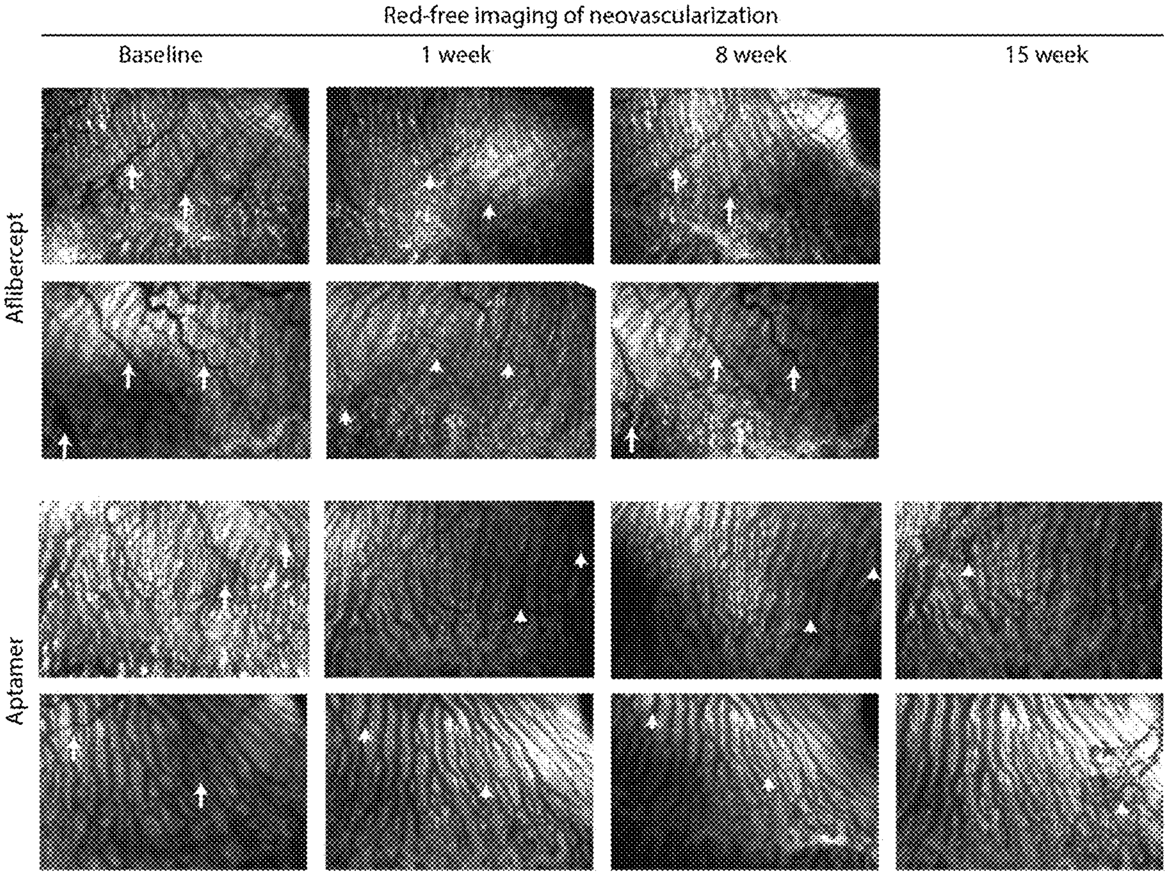
FIG. 8 illustrates the representative red-free imaging photos of the rabbit DL-AAA study results of anti-VEGF aptamers of the present disclosure.

The effect on pathologic NV was measured by red-free imaging (FIG. 8). Before the injection of test articles, NV was apparent in all the eyes (marked by arrows). At 1 week after injection, regression of retinal NV was observed in the Aflibercept arm, but residual NV was still apparent (marked by arrowheads). In contrast, AMSB107P resulted in near-complete regression of retinal NV (arrowheads were placed at the same locations where NV previously appeared for orientation).

At 8 weeks after injection, NV already grew back to the baseline level in Aflibercept-treated eyes. The regrowth followed the same vascular pattern observed before injection. In contrast, AMSB107P still maintained its inhibitory effect on retinal NV (marked by arrowheads).

At 15 weeks after injection, NV regrowth (marked by arrowheads) was observed in eyes treated with AMSB107P. The new NV followed a different pattern compared to the NV observed before injection, suggesting the aptamer caused vascular remodeling. Similar effect of vascular remodeling was also reported in a previous report (refer to Bibiana, T. MacPherson, J. Cao, C. Romano, Aflibercept in combination with nesvacumab (anti-Ang2) induces vascular remodeling in a rabbit model of pathological neovascularization, Invest. Ophthalmol. Vis. Sci. 59, 1447-1447 (2018)), where the combination of Aflibercept and an Ang2 antibody (Nesvacumab) caused vascular remodeling while Aflibercept alone did not show such effect.

Figure 9:
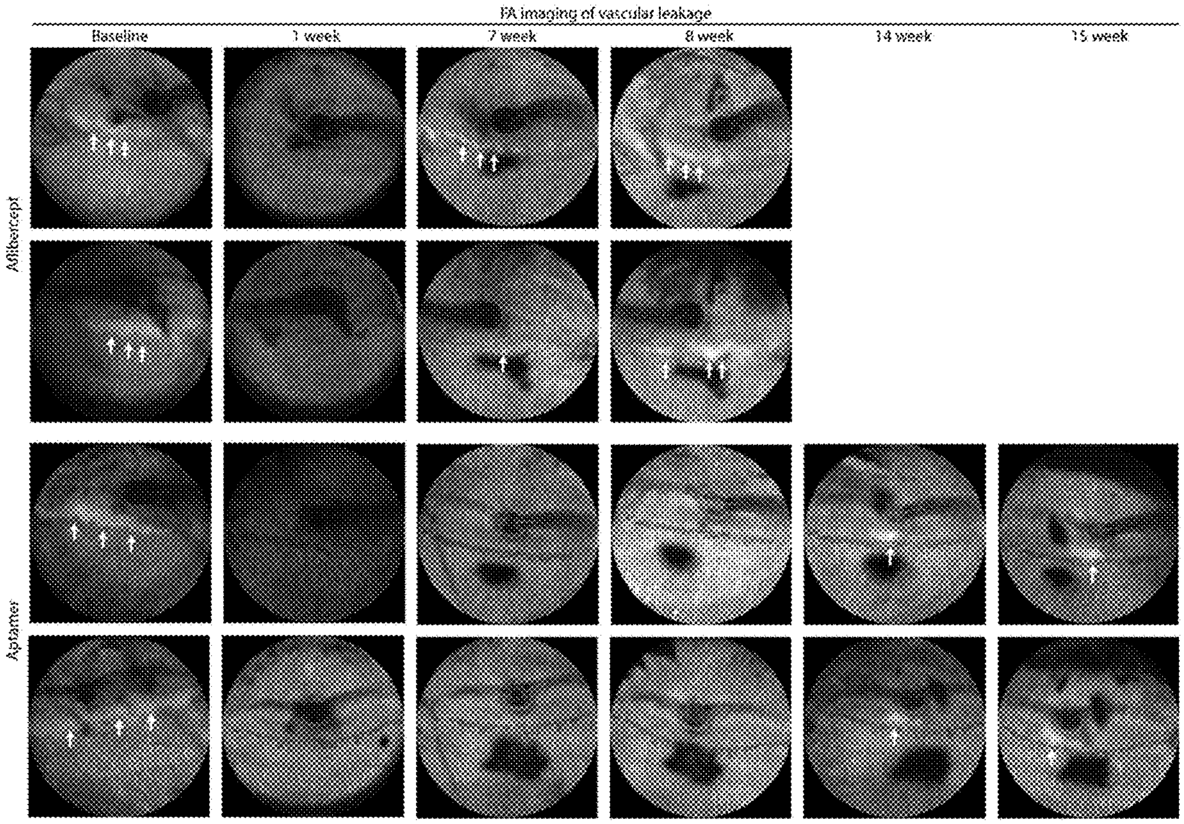
FIG. 9 illustrates the representative FA photos of the rabbit DL-AAA study results of anti-VEGF aptamers of the present disclosure.

The effect on vascular leakage was measured by FA (FIG. 9). Before the injection of test articles, leakage was apparent in all the eyes (marked by white arrows). At 1 week after injection, both Aflibercept and AMSB107P resulted in complete suppression of leakage. At 7 weeks after injection, Aflibercept-treated eyes started to leak again; the leakage worsened at 8 weeks after injection, reverting to the baseline level. In contrast, no leakage was observed in the aptamer-treated eyes at 7 and 8 weeks after injection. Minor leakage was observed starting at 14 weeks after injection; the extent of leakage at week 14 and 15 were both significantly less than the baseline level.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

The invention claimed is:

1. An anti-VEGF aptamer, which binds to VEGF-121 with a KD value of about 20 nanomolar (nM) or less, and binds to VEGF-165 with a KD value of about 20 nanomolar (nM) or less, wherein said anti-VEGF aptamer comprises a first consensus sequence comprising a nucleotide sequence as set forth in any of SEQ ID NO: 136-137 or a second consensus sequence comprising a nucleotide sequence as set forth in any of SEQ ID NO: 138-139.

2. The anti-VEGF aptamer of claim 1, wherein said anti-VEGF aptamer comprises a nucleotide sequence as set forth in any of SEQ ID NO: 47, 70-90, 93, 115-135, SEQ ID NO: 200-201.

3. A bispecific aptamer, comprising a nucleotide sequence as set forth in any of SEQ ID NO: 140-147, 149-158, 161-174, 176-185, 188-195, SEQ ID NO: 202-204.

* * * * *

SEQUENCE LISTING

```
<160> NUMBER OF SEQ ID NOS: 204

<210> SEQ ID NO 1
<211> LENGTH: 61
<212> TYPE: RNA
<213> ORGANISM: Artificial Sequence
<220> FEATURE:
<223> OTHER INFORMATION: natural anti-Ang2 aptamer

<400> SEQUENCE: 1
```

-continued

```
gcauagauaa gccaacaaac guacauucuc uguuaguauu uucugcacac cgucgcuuag     60

u                                                                     61


<210> SEQ ID NO 2
<211> LENGTH: 48
<212> TYPE: RNA
<213> ORGANISM: Artificial Sequence
<220> FEATURE:
<223> OTHER INFORMATION: natural anti-Ang2 aptamer

<400> SEQUENCE: 2

cgcauagaua agccaacaaa cguacauucu cuguuaguau uuucugcg                  48


<210> SEQ ID NO 3
<211> LENGTH: 48
<212> TYPE: RNA
<213> ORGANISM: Artificial Sequence
<220> FEATURE:
<223> OTHER INFORMATION: natural anti-Ang2 aptamer

<400> SEQUENCE: 3

gccuuagaua agccaacaaa cguacauucu cuguuaguau uuucaggc                  48


<210> SEQ ID NO 4
<211> LENGTH: 40
<212> TYPE: RNA
<213> ORGANISM: Artificial Sequence
<220> FEATURE:
<223> OTHER INFORMATION: natural anti-Ang2 aptamer

<400> SEQUENCE: 4

ccgauaagcc aacaaacgua cauucucugu uaguauucgg                          40


<210> SEQ ID NO 5
<211> LENGTH: 61
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(61)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 5

gcauagauaa gccaacaaac guacauucuc uguuaguauu uucugcacac cgucgcuuag     60

u                                                                     61


<210> SEQ ID NO 6
<211> LENGTH: 48
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(48)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 6

cgcauagaua agccaacaaa cguacauucu cuguuaguau uuucugcg                  48
```

```
<210> SEQ ID NO 7
<211> LENGTH: 48
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(48)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 7

gccuuagaua agccaacaaa cguacauucu cuguuaguau uuucaggc                48


<210> SEQ ID NO 8
<211> LENGTH: 40
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(40)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 8

ccgauaagcc aacaaacgua cauucucugu uaguauucgg                         40


<210> SEQ ID NO 9
<211> LENGTH: 48
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(4)
<223> OTHER INFORMATION: a represents 2'-O-methyl A, u represents 2'-O-
      methyl U, c represents 2'-O-methyl C, g represents 2'-O-methyl G
<220> FEATURE:
<221> NAME/KEY: misc_feature
<222> LOCATION: (5)..(44)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid
<220> FEATURE:
<221> NAME/KEY: misc_feature
<222> LOCATION: (45)..(48)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 9

cgcauagaua agccaacaaa cguacauucu cuguuaguau uuucugcg                48


<210> SEQ ID NO 10
<211> LENGTH: 48
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(4)
<223> OTHER INFORMATION: a represents locked nucleic acid (LNA) A, u
      represents locked nucleic acid (LNA) U, c represents locked
      nucleic acid (LNA) C, g represents locked nucleic acid (LNA) G
<220> FEATURE:
<221> NAME/KEY: misc_feature
```

-continued

<222> LOCATION: (5)..(44)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid
<220> FEATURE:
<221> NAME/KEY: misc_feature
<222> LOCATION: (45)..(48)
<223> OTHER INFORMATION: a represents locked nucleic acid (LNA) A, u
      represents locked nucleic acid (LNA) U, c represents locked
      nucleic acid (LNA) C, g represents locked nucleic acid (LNA) G

<400> SEQUENCE: 10
cgcauagaua agccaacaaa cguacauucu cuguuaguau uuucugcg 48

<210> SEQ ID NO 11
<211> LENGTH: 43
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(20)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid
<220> FEATURE:
<221> NAME/KEY: misc_feature
<222> LOCATION: (21)..(21)
<223> OTHER INFORMATION: n denotes hexa-ethyleneglycol (Heg) linker
<220> FEATURE:
<221> NAME/KEY: misc_feature
<222> LOCATION: (22)..(43)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 11
cgcauagaua agccaacaaa nuucucuguu aguauuuucu gcg 43

<210> SEQ ID NO 12
<211> LENGTH: 45
<212> TYPE: RNA
<213> ORGANISM: Artificial Sequence
<220> FEATURE:
<223> OTHER INFORMATION: modified anti-Ang2 aptamer
<220> FEATURE:
<221> NAME/KEY: misc_feature
<222> LOCATION: (1)..(21)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid
<220> FEATURE:
<221> NAME/KEY: misc_feature
<222> LOCATION: (22)..(22)
<223> OTHER INFORMATION: h denotes hexa-ethyleneglycol (Heg) linker
<220> FEATURE:
<221> NAME/KEY: misc_feature
<222> LOCATION: (23)..(45)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 12
cgcauagaua agccaacaaa chauucucug uuaguauuuu cugcg 45

<210> SEQ ID NO 13
<211> LENGTH: 13
<212> TYPE: RNA
<213> ORGANISM: Artificial Sequence
<220> FEATURE:
<223> OTHER INFORMATION: modified anti-Ang2 aptamer first concensus
      sequence -continued <220> FEATURE:
<221> NAME/KEY: misc_feature
<222> LOCATION: (1)..(13)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 13
agauaagcca aca 13

<210> SEQ ID NO 14
<211> LENGTH: 14
<212> TYPE: RNA
<213> ORGANISM: Artificial Sequence
<220> FEATURE:
<223> OTHER INFORMATION: modified anti-Ang2 aptamer first concensus
      sequence
<220> FEATURE:
<221> NAME/KEY: misc_feature
<222> LOCATION: (1)..(14)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 14
uagauaagcc aaca 14

<210> SEQ ID NO 15
<211> LENGTH: 15
<212> TYPE: RNA
<213> ORGANISM: Artificial Sequence
<220> FEATURE:
<223> OTHER INFORMATION: modified anti-Ang2 aptamer first concensus
      sequence
<220> FEATURE:
<221> NAME/KEY: misc_feature
<222> LOCATION: (1)..(15)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 15
auagauaagc caaca 15

<210> SEQ ID NO 16
<211> LENGTH: 15
<212> TYPE: RNA
<213> ORGANISM: Artificial Sequence
<220> FEATURE:
<223> OTHER INFORMATION: modified anti-Ang2 aptamer first concensus
      sequence
<220> FEATURE:
<221> NAME/KEY: misc_feature
<222> LOCATION: (1)..(15)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 16
cuagauaagc caaca 15

<210> SEQ ID NO 17
<211> LENGTH: 13
<212> TYPE: RNA
<213> ORGANISM: Artificial Sequence
<220> FEATURE:
<223> OTHER INFORMATION: natural anti-Ang2 aptamer first concensus
      sequence

<400> SEQUENCE: 17

-continued agauaagcca aca 13

<210> SEQ ID NO 18
<211> LENGTH: 14
<212> TYPE: RNA
<213> ORGANISM: Artificial Sequence
<220> FEATURE:
<223> OTHER INFORMATION: natural anti-Ang2 aptamer first concensus
sequence

<400> SEQUENCE: 18
uagauaagcc aaca 14

<210> SEQ ID NO 19
<211> LENGTH: 15
<212> TYPE: RNA
<213> ORGANISM: Artificial Sequence
<220> FEATURE:
<223> OTHER INFORMATION: natural anti-Ang2 aptamer first concensus
sequence

<400> SEQUENCE: 19
auagauaagc caaca 15

<210> SEQ ID NO 20
<211> LENGTH: 15
<212> TYPE: RNA
<213> ORGANISM: Artificial Sequence
<220> FEATURE:
<223> OTHER INFORMATION: natural anti-Ang2 aptamer first concensus
sequence

<400> SEQUENCE: 20
cuagauaagc caaca 15

<210> SEQ ID NO 21
<211> LENGTH: 12
<212> TYPE: RNA
<213> ORGANISM: Artificial Sequence
<220> FEATURE:
<223> OTHER INFORMATION: modified anti-Ang2 aptamer second concensus
sequence
<220> FEATURE:
<221> NAME/KEY: misc_feature
<222> LOCATION: (1)..(12)
<223> OTHER INFORMATION: a represents 2'-fluoroadenylic acid, u
represents 2'-fluorouridylic acid, c represents 2'-fluorocytidylic
acid, g represents 2'-fluoroguanylic acid

<400> SEQUENCE: 21
uguuaguauu uu 12

<210> SEQ ID NO 22
<211> LENGTH: 13
<212> TYPE: RNA
<213> ORGANISM: Artificial Sequence
<220> FEATURE:
<223> OTHER INFORMATION: modified anti-Ang2 aptamer second concensus
sequence
<220> FEATURE:
<221> NAME/KEY: misc_feature
<222> LOCATION: (1)..(13)
<223> OTHER INFORMATION: a represents 2'-fluoroadenylic acid, u
represents 2'-fluorouridylic acid, c represents 2'-fluorocytidylic
acid, g represents 2'-fluoroguanylic acid

<400> SEQUENCE: 22
uguuaguauu uuc 13

<210> SEQ ID NO 23
<211> LENGTH: 14
<212> TYPE: RNA
<213> ORGANISM: Artificial Sequence
<220> FEATURE:
<223> OTHER INFORMATION: modified anti-Ang2 aptamer second concensus
      sequence
<220> FEATURE:
<221> NAME/KEY: misc_feature
<222> LOCATION: (1)..(14)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 23
uguuaguauu uucu 14

<210> SEQ ID NO 24
<211> LENGTH: 14
<212> TYPE: RNA
<213> ORGANISM: Artificial Sequence
<220> FEATURE:
<223> OTHER INFORMATION: modified anti-Ang2 aptamer second concensus
      sequence
<220> FEATURE:
<221> NAME/KEY: misc_feature
<222> LOCATION: (1)..(14)
<223> OTHER INFORMATION: a represents 2'-fluoroadenylic acid, u
      represents 2'-fluorouridylic acid, c represents 2'-fluorocytidylic
      acid, g represents 2'-fluoroguanylic acid

<400> SEQUENCE: 24
uguuaguauu uucg 14

<210> SEQ ID NO 25
<211> LENGTH: 12
<212> TYPE: RNA
<213> ORGANISM: Artificial Sequence
<220> FEATURE:
<223> OTHER INFORMATION: natural anti-Ang2 aptamer second concensus
      sequence

<400> SEQUENCE: 25
uguuaguauu uu 12

<210> SEQ ID NO 26
<211> LENGTH: 13
<212> TYPE: RNA
<213> ORGANISM: Artificial Sequence
<220> FEATURE:
<223> OTHER INFORMATION: natural anti-Ang2 aptamer second concensus
      sequence

<400> SEQUENCE: 26
uguuaguauu uuc 13

<210> SEQ ID NO 27
<211> LENGTH: 14
<212> TYPE: RNA
<213> ORGANISM: Artificial Sequence
<220> FEATURE:
<223> OTHER INFORMATION: natural anti-Ang2 aptamer second concensus
      sequence

<400> SEQUENCE: 27
uguuaguauu uucu 14

<210> SEQ ID NO 28

-continued

<211> LENGTH: 14
<212> TYPE: RNA
<213> ORGANISM: Artificial Sequence
<220> FEATURE:
<223> OTHER INFORMATION: natural anti-Ang2 aptamer second concensus sequence

<400> SEQUENCE: 28
uguuaguauu uucg 14

<210> SEQ ID NO 29
<211> LENGTH: 121
<212> TYPE: PRT
<213> ORGANISM: Artificial Sequence
<220> FEATURE:
<223> OTHER INFORMATION: human VEGF121

<400> SEQUENCE: 29

```
Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120
```

<210> SEQ ID NO 30
<211> LENGTH: 9
<212> TYPE: PRT
<213> ORGANISM: Artificial Sequence
<220> FEATURE:
<223> OTHER INFORMATION: human VEGF121 receptor binding domain 1,human VEGF165 receptor binding domain 1,Monkey VEGF 165 receptor binding domain 1, Rat VEGF 164 receptor binding domain 1,Rat VEGF 120 receptor binding domain 1,Mouse VEGF 164 receptor binding domain 1,Mouse VEGF 120

<400> SEQUENCE: 30

```
Phe Met Asp Val Tyr Gln Arg Ser Tyr
1               5
```

<210> SEQ ID NO 31
<211> LENGTH: 15
<212> TYPE: PRT
<213> ORGANISM: Artificial Sequence
<220> FEATURE:
<223> OTHER INFORMATION: human VEGF121 receptor binding domain 2,human VEGF165 receptor binding domain 2, Rabbit VEGF 189 receptor binding domain 2,Monkey VEGF 165 receptor binding domain 2, Rat VEGF 164 receptor binding domain 2,Rat VEGF 120 receptor binding domain 2,Mouse VEGF 164

<400> SEQUENCE: 31

```
Asp Ile Phe Gln Glu Tyr Pro Asp Glu Ile Glu Tyr Ile Phe Lys
1               5                   10                  15
```

```
<210> SEQ ID NO 32
<211> LENGTH: 6
<212> TYPE: PRT
<213> ORGANISM: Artificial Sequence
<220> FEATURE:
<223> OTHER INFORMATION: human VEGF121 receptor binding domain 3,human
      VEGF165 receptor binding domain 3,Monkey VEGF 165 receptor binding
      domain 3

<400> SEQUENCE: 32

Cys Asn Asp Glu Gly Leu
1               5


<210> SEQ ID NO 33
<211> LENGTH: 13
<212> TYPE: PRT
<213> ORGANISM: Artificial Sequence
<220> FEATURE:
<223> OTHER INFORMATION: human VEGF121 receptor binding domain 4,human
      VEGF165 receptor binding domain 4, Monkey VEGF 165 receptor
      binding domain 4,Rabbit VEGF 189 receptor binding domain 4,Rat
      VEGF 164 receptor binding domain 4,Rat VEGF 120 receptor binding
      domain 4,Mouse VEGF 164

<400> SEQUENCE: 33

Gln Ile Met Arg Ile Lys Pro His Gln Gly Gln His Ile
1               5                   10


<210> SEQ ID NO 34
<211> LENGTH: 8
<212> TYPE: PRT
<213> ORGANISM: Artificial Sequence
<220> FEATURE:
<223> OTHER INFORMATION: human VEGF121 receptor binding domain 5,human
      VEGF165 receptor binding domain 5,Moneky VEGF 165 receptor binding
      domain 5, Rabbit VEGF 189 receptor binding domain 5

<400> SEQUENCE: 34

Lys Cys Glu Cys Arg Pro Lys Lys
1               5


<210> SEQ ID NO 35
<211> LENGTH: 165
<212> TYPE: PRT
<213> ORGANISM: Artificial Sequence
<220> FEATURE:
<223> OTHER INFORMATION: human VEGF165,Monkey VEGF 165

<400> SEQUENCE: 35

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
```

```
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165


<210> SEQ ID NO 36
<211> LENGTH: 189
<212> TYPE: PRT
<213> ORGANISM: Artificial Sequence
<220> FEATURE:
<223> OTHER INFORMATION: Rabbit VEGF 189

<400> SEQUENCE: 36

Ala Pro Met Ala Glu Glu Gly Asp Asn Lys Pro His Glu Val Val Lys
1               5                   10                  15

Phe Met Glu Val Tyr Arg Arg Ser Tyr Cys Gln Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Val Arg Cys Gly Gly Cys Cys Asn Asp Glu
    50                  55                  60

Ser Leu Glu Cys Val Pro Thr Glu Glu Phe Asn Val Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Pro Cys Gly Pro Cys
    130                 135                 140

Ser Glu Arg Arg Lys His Leu Phe Val Gln Asp Pro Gln Thr Cys Lys
145                 150                 155                 160

Cys Ser Cys Lys Asn Thr Asp Ser Arg Cys Lys Ala Arg Gln Leu Glu
                165                 170                 175

Leu Asn Glu Arg Thr Cys Arg Cys Asp Lys Pro Arg Arg
            180                 185


<210> SEQ ID NO 37
<211> LENGTH: 9
<212> TYPE: PRT
<213> ORGANISM: Artificial Sequence
<220> FEATURE:
<223> OTHER INFORMATION: Rabbit VEGF 189 receptor binding domain 1

<400> SEQUENCE: 37

Phe Met Glu Val Tyr Arg Arg Ser Tyr
1               5


<210> SEQ ID NO 38
<211> LENGTH: 6
<212> TYPE: PRT
<213> ORGANISM: Artificial Sequence
<220> FEATURE:
<223> OTHER INFORMATION: Rabbit VEGF 189 receptor binding domain 3

<400> SEQUENCE: 38
```

```
Cys Asn Asp Glu Ser Leu
1               5


<210> SEQ ID NO 39
<211> LENGTH: 164
<212> TYPE: PRT
<213> ORGANISM: Artificial Sequence
<220> FEATURE:
<223> OTHER INFORMATION: Rat VEGF 164

<400> SEQUENCE: 39

Ala Pro Thr Thr Glu Gly Glu Gln Lys Ala His Glu Val Val Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Val Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Asn His Cys Glu Pro Cys Ser Glu Arg Arg Lys His Leu Phe Val
        115                 120                 125

Gln Asp Pro Gln Thr Cys Lys Cys Ser Cys Lys Asn Thr Asp Ser Arg
    130                 135                 140

Cys Lys Ala Arg Gln Leu Glu Leu Asn Glu Arg Thr Cys Arg Cys Asp
145                 150                 155                 160

Lys Pro Arg Arg


<210> SEQ ID NO 40
<211> LENGTH: 6
<212> TYPE: PRT
<213> ORGANISM: Artificial Sequence
<220> FEATURE:
<223> OTHER INFORMATION: Rat VEGF 164 receptor binding domain 3,Rat VEGF
      120 receptor binding domain 3,Mouse VEGF 164 receptor binding
      domain 3,Mouse VEGF 120 receptor binding domain 3

<400> SEQUENCE: 40

Cys Asn Asp Glu Ala Leu
1               5


<210> SEQ ID NO 41
<211> LENGTH: 8
<212> TYPE: PRT
<213> ORGANISM: Artificial Sequence
<220> FEATURE:
<223> OTHER INFORMATION: Rat VEGF 164 receptor binding domain 5,Rat VEGF
      120 receptor binding domain 5,Mouse VEGF 164 receptor binding
      domain 5,Mouse VEGF 120 receptor binding domain 5

<400> SEQUENCE: 41

Arg Cys Glu Cys Arg Pro Lys Lys
1               5


<210> SEQ ID NO 42
<211> LENGTH: 120
```

<212> TYPE: PRT
<213> ORGANISM: Artificial Sequence
<220> FEATURE:
<223> OTHER INFORMATION: Rat VEGF 120

<400> SEQUENCE: 42

Ala Pro Thr Thr Glu Gly Glu Gln Lys Ala His Glu Val Val Lys Phe
1 5 10 15

Met Asp Val Tyr Gln Arg Ser Tyr Cys Arg Pro Ile Glu Thr Leu Val
20 25 30

Asp Ile Phe Gln Glu Tyr Pro Asp Glu Ile Glu Tyr Ile Phe Lys Pro
35 40 45

Ser Cys Val Pro Leu Met Arg Cys Ala Gly Cys Cys Asn Asp Glu Ala
50 55 60

Leu Glu Cys Val Pro Thr Ser Glu Ser Asn Val Thr Met Gln Ile Met
65 70 75 80

Arg Ile Lys Pro His Gln Ser Gln His Ile Gly Glu Met Ser Phe Leu
85 90 95

Gln His Ser Arg Cys Glu Cys Arg Pro Lys Lys Asp Arg Thr Lys Pro
100 105 110

Glu Lys Cys Asp Lys Pro Arg Arg
115 120

<210> SEQ ID NO 43
<211> LENGTH: 164
<212> TYPE: PRT
<213> ORGANISM: Artificial Sequence
<220> FEATURE:
<223> OTHER INFORMATION: Mouse VEGF 164

<400> SEQUENCE: 43

Ala Pro Thr Thr Glu Gly Glu Gln Lys Ser His Glu Val Ile Lys Phe
1 5 10 15

Met Asp Val Tyr Gln Arg Ser Tyr Cys Arg Pro Ile Glu Thr Leu Val
20 25 30

Asp Ile Phe Gln Glu Tyr Pro Asp Glu Ile Glu Tyr Ile Phe Lys Pro
35 40 45

Ser Cys Val Pro Leu Met Arg Cys Ala Gly Cys Cys Asn Asp Glu Ala
50 55 60

Leu Glu Cys Val Pro Thr Ser Glu Ser Asn Ile Thr Met Gln Ile Met
65 70 75 80

Arg Ile Lys Pro His Gln Ser Gln His Ile Gly Glu Met Ser Phe Leu
85 90 95

Gln His Ser Arg Cys Glu Cys Arg Pro Lys Lys Asp Arg Thr Lys Pro
100 105 110

Glu Asn His Cys Glu Pro Cys Ser Glu Arg Arg Lys His Leu Phe Val
115 120 125

Gln Asp Pro Gln Thr Cys Lys Cys Ser Cys Lys Asn Thr Asp Ser Arg
130 135 140

Cys Lys Ala Arg Gln Leu Glu Leu Asn Glu Arg Thr Cys Arg Cys Asp
145 150 155 160

Lys Pro Arg Arg

<210> SEQ ID NO 44
<211> LENGTH: 120
<212> TYPE: PRT
<213> ORGANISM: Artificial Sequence
<220> FEATURE:

<223> OTHER INFORMATION: Mouse VEGF 120

<400> SEQUENCE: 44

Ala Pro Thr Thr Glu Gly Glu Gln Lys Ser His Glu Val Ile Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Ile Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Lys Cys Asp Lys Pro Arg Arg
        115                 120

<210> SEQ ID NO 45
<211> LENGTH: 13
<212> TYPE: PRT
<213> ORGANISM: Artificial Sequence
<220> FEATURE:
<223> OTHER INFORMATION: Mouse VEGF 120 receptor binding domain 4

<400> SEQUENCE: 45

Gln Ile Met Arg Ile Lys Pro His Gln Ser Gln His Ile
1               5                   10

<210> SEQ ID NO 46
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 46
aguuauuugg uggagaggau ccauuuagcu uauacaauuc                          40

<210> SEQ ID NO 47
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 47
ccggccauug guggagauua uccuuugagu acgguuauuc                          40

<210> SEQ ID NO 48
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 48
acccuugcuu gcguagcauu uuaccaguga gucggaucuc                          40

<210> SEQ ID NO 49

<211> LENGTH: 38
<212> TYPE: RNA
<213> ORGANISM: Artificial Sequence
<220> FEATURE:
<223> OTHER INFORMATION: natural anti-VEGF aptamer

<400> SEQUENCE: 49
gacgcgaccu cguacccccu uguuguuacg gucgcguc 38

<210> SEQ ID NO 50
<211> LENGTH: 38
<212> TYPE: RNA
<213> ORGANISM: Artificial Sequence
<220> FEATURE:
<223> OTHER INFORMATION: natural anti-VEGF aptamer

<400> SEQUENCE: 50
gacgcgaccu uuuuguuccu uggcuccaag gucgcguc 38

<210> SEQ ID NO 51
<211> LENGTH: 38
<212> TYPE: RNA
<213> ORGANISM: Artificial Sequence
<220> FEATURE:
<223> OTHER INFORMATION: natural anti-VEGF aptamer

<400> SEQUENCE: 51
gacgcgaccu uggcuuuaga gaguuccuug gucgcguc 38

<210> SEQ ID NO 52
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 52
ccacaguaaa uuugauuagu cgugugaaga aaacugucaa 40

<210> SEQ ID NO 53
<211> LENGTH: 43
<212> TYPE: RNA
<213> ORGANISM: Artificial Sequence
<220> FEATURE:
<223> OTHER INFORMATION: natural anti-VEGF aptamer

<400> SEQUENCE: 53
aaauagaaaa uuaaacgacc cugggaacgu gaauacccag ccu 43

<210> SEQ ID NO 54
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 54
ccucguacaa gguuuguaau ccacaguaag gaugagcuga 40

<210> SEQ ID NO 55
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 55
ggaaucuaaa auccggauag auaagaaagu uuggugagcc 40

<210> SEQ ID NO 56
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 56
cugcuccaug ugcaguuaca aauggccauc aauuggauuu 40

<210> SEQ ID NO 57
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 57
ugaauaacgc ggaaaucuag auaguaauac gguuuuuccc 40

<210> SEQ ID NO 58
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 58
agacucuaga augaugcaua ucguugcauu acgguugucu 40

<210> SEQ ID NO 59
<211> LENGTH: 36
<212> TYPE: RNA
<213> ORGANISM: Artificial Sequence
<220> FEATURE:
<223> OTHER INFORMATION: natural anti-VEGF aptamer

<400> SEQUENCE: 59
ugacuuccuc uagaauacua uguacgguug ggguca 36

<210> SEQ ID NO 60
<211> LENGTH: 40
<212> TYPE: RNA
<213> ORGANISM: Artificial Sequence
<220> FEATURE:
<223> OTHER INFORMATION: natural anti-VEGF aptamer

<400> SEQUENCE: 60
auagaagaau gacgucaaaa uaaccaaugu acugggcuac 40

<210> SEQ ID NO 61
<211> LENGTH: 32
<212> TYPE: RNA
<213> ORGANISM: Artificial Sequence
<220> FEATURE:
<223> OTHER INFORMATION: natural anti-VEGF aptamer

<400> SEQUENCE: 61
gcgaccucua gaauaguaau acgguugguc gc 32

<210> SEQ ID NO 62
<211> LENGTH: 31
<212> TYPE: RNA

<213> ORGANISM: Artificial Sequence
<220> FEATURE:
<223> OTHER INFORMATION: natural anti-VEGF aptamer

<400> SEQUENCE: 62
gcgacuuaug uguguucuau uuuuuggucg c 31

<210> SEQ ID NO 63
<211> LENGTH: 32
<212> TYPE: RNA
<213> ORGANISM: Artificial Sequence
<220> FEATURE:
<223> OTHER INFORMATION: natural anti-VEGF aptamer

<400> SEQUENCE: 63
gcgaccucua gaaugguaac acgguugguc gc 32

<210> SEQ ID NO 64
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 64
gcgaccguuu uaugaaaaag acuuggggguu cuacaugguc gc 42

<210> SEQ ID NO 65
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 65
gcgaccugug uccuaacuuu uguaucgaau gaucuggguc gc 42

<210> SEQ ID NO 66
<211> LENGTH: 41
<212> TYPE: RNA
<213> ORGANISM: Artificial Sequence
<220> FEATURE:
<223> OTHER INFORMATION: natural anti-VEGF aptamer

<400> SEQUENCE: 66
gcgacuugug ucuaaacuuu uaucuauccu aguugggucg c 41

<210> SEQ ID NO 67
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 67
gcgaccaaag caucuagaua guaauacggu uugcucgguc gc 42

<210> SEQ ID NO 68
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 68
gcgaccucac acaaaauggu agccuauuau auauacgguc gc 42

<210> SEQ ID NO 69
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 69
gcgaccugaa uucuagaaug guaacacggu uauucugguc gc 42

<210> SEQ ID NO 70
<211> LENGTH: 52
<212> TYPE: RNA
<213> ORGANISM: Artificial Sequence
<220> FEATURE:
<223> OTHER INFORMATION: natural anti-VEGF aptamer

<400> SEQUENCE: 70
acccuugcuu gcguagcauu uuaccaguga gucggaucuc cgcauaucug cg 52

<210> SEQ ID NO 71
<211> LENGTH: 43
<212> TYPE: RNA
<213> ORGANISM: Artificial Sequence
<220> FEATURE:
<223> OTHER INFORMATION: natural anti-VEGF aptamer

<400> SEQUENCE: 71
ugccagugag ucggaucucc gcauaucugc gcgcauaucu gcg 43

<210> SEQ ID NO 72
<211> LENGTH: 52
<212> TYPE: RNA
<213> ORGANISM: Artificial Sequence
<220> FEATURE:
<223> OTHER INFORMATION: natural anti-VEGF aptamer

<400> SEQUENCE: 72
acccuugcuu gcguagcauu cugccaguga gucggaucuc cgcauaucug cg 52

<210> SEQ ID NO 73
<211> LENGTH: 52
<212> TYPE: RNA
<213> ORGANISM: Artificial Sequence
<220> FEATURE:
<223> OTHER INFORMATION: natural anti-VEGF aptamer

<400> SEQUENCE: 73
acccuugcuu gcgcagcauu cugccaguga gucggaucuc cgcauaucug cg 52

<210> SEQ ID NO 74
<211> LENGTH: 51
<212> TYPE: RNA
<213> ORGANISM: Artificial Sequence
<220> FEATURE:
<223> OTHER INFORMATION: natural anti-VEGF aptamer

<400> SEQUENCE: 74
caccaugcuu gcguagcauc auccagugag ucggaucucc gcauaucugc g 51

<210> SEQ ID NO 75
<211> LENGTH: 50
<212> TYPE: RNA
<213> ORGANISM: Artificial Sequence
<220> FEATURE:

<223> OTHER INFORMATION: natural anti-VEGF aptamer

<400> SEQUENCE: 75
ccccaucugc gaagcaguca gccagugagu cggaucuccg cauaucugcg 50

<210> SEQ ID NO 76
<211> LENGTH: 45
<212> TYPE: RNA
<213> ORGANISM: Artificial Sequence
<220> FEATURE:
<223> OTHER INFORMATION: natural anti-VEGF aptamer

<400> SEQUENCE: 76
cacagagaac ugugugccag ugagucggau cuccgcauau cugcg 45

<210> SEQ ID NO 77
<211> LENGTH: 41
<212> TYPE: RNA
<213> ORGANISM: Artificial Sequence
<220> FEATURE:
<223> OTHER INFORMATION: natural anti-VEGF aptamer

<400> SEQUENCE: 77
cguagcauuu ugccagugag ucggaucucc gcauaucugc g 41

<210> SEQ ID NO 78
<211> LENGTH: 25
<212> TYPE: RNA
<213> ORGANISM: Artificial Sequence
<220> FEATURE:
<223> OTHER INFORMATION: natural anti-VEGF aptamer

<400> SEQUENCE: 78
ugagucggau cuccgcauau cugcg 25

<210> SEQ ID NO 79
<211> LENGTH: 33
<212> TYPE: RNA
<213> ORGANISM: Artificial Sequence
<220> FEATURE:
<223> OTHER INFORMATION: natural anti-VEGF aptamer

<400> SEQUENCE: 79
ugccagugag ucggaucucc ugugagaaca cag 33

<210> SEQ ID NO 80
<211> LENGTH: 55
<212> TYPE: RNA
<213> ORGANISM: Artificial Sequence
<220> FEATURE:
<223> OTHER INFORMATION: natural anti-VEGF aptamer

<400> SEQUENCE: 80
cacagagaac ugugccuagc auuuugccag ugagucggau cuccgcauau cugcg 55

<210> SEQ ID NO 81
<211> LENGTH: 27
<212> TYPE: RNA
<213> ORGANISM: Artificial Sequence
<220> FEATURE:
<223> OTHER INFORMATION: natural anti-VEGF aptamer

<400> SEQUENCE: 81
ugagcucgga ugcuccgcau aucugcg 27

-continued

<210> SEQ ID NO 82
<211> LENGTH: 52
<212> TYPE: RNA
<213> ORGANISM: Artificial Sequence
<220> FEATURE:
<223> OTHER INFORMATION: natural anti-VEGF aptamer

<400> SEQUENCE: 82
uuuugugcuu gcguagcaac ccuccaguga gucggaucuc cgcauaucug cg 52

<210> SEQ ID NO 83
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 83
ugcaugcauu uuaccaguga gucggaucuc cgcauaucug cg 42

<210> SEQ ID NO 84
<211> LENGTH: 48
<212> TYPE: RNA
<213> ORGANISM: Artificial Sequence
<220> FEATURE:
<223> OTHER INFORMATION: natural anti-VEGF aptamer

<400> SEQUENCE: 84
acccuugcuu gcguagcauu uuaccaguga gucggaucuc ugcaugca 48

<210> SEQ ID NO 85
<211> LENGTH: 30
<212> TYPE: RNA
<213> ORGANISM: Artificial Sequence
<220> FEATURE:
<223> OTHER INFORMATION: natural anti-VEGF aptamer

<400> SEQUENCE: 85
uuuuaccagu gagucggauc ucugcaugca 30

<210> SEQ ID NO 86
<211> LENGTH: 43
<212> TYPE: RNA
<213> ORGANISM: Artificial Sequence
<220> FEATURE:
<223> OTHER INFORMATION: natural anti-VEGF aptamer

<400> SEQUENCE: 86
ugcacugcau uuuaccagug agucggaucu ccgcauaucu gcg 43

<210> SEQ ID NO 87
<211> LENGTH: 44
<212> TYPE: RNA
<213> ORGANISM: Artificial Sequence
<220> FEATURE:
<223> OTHER INFORMATION: natural anti-VEGF aptamer

<400> SEQUENCE: 87
ugcaucugca uuuuaccagu gagucggauc uccgcauauc ugcg 44

<210> SEQ ID NO 88
<211> LENGTH: 42
<212> TYPE: RNA
<213> ORGANISM: Artificial Sequence
<220> FEATURE:
<223> OTHER INFORMATION: natural anti-VEGF aptamer

<400> SEQUENCE: 88
cuguacaguu uuaccaguga gucggaucuc cgcauaucug cg 42

<210> SEQ ID NO 89
<211> LENGTH: 45
<212> TYPE: RNA
<213> ORGANISM: Artificial Sequence
<220> FEATURE:
<223> OTHER INFORMATION: natural anti-VEGF aptamer

<400> SEQUENCE: 89
uuuugcaugc auuuuaccag ugagucggau cuccgcauau cugcg 45

<210> SEQ ID NO 90
<211> LENGTH: 44
<212> TYPE: RNA
<213> ORGANISM: Artificial Sequence
<220> FEATURE:
<223> OTHER INFORMATION: natural anti-VEGF aptamer

<400> SEQUENCE: 90
gcuguacagc uuuuaccagu gagucggauc uccgcauauc ugcg 44

<210> SEQ ID NO 91
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 91
aguuauuugg uggagaggau ccauuuagcu uauacaauuc 40

<210> SEQ ID NO 92
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 92
ccggccauug guggagauua ucccuuugagu acgguuauuc 40

<210> SEQ ID NO 93
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 93
acccuugcuu gcguagcauu uuaccaguga gucggaucuc 40

<210> SEQ ID NO 94
<211> LENGTH: 38
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(38)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 94
gacgcgaccu cguacccccu uguuguuacg gucgcguc 38

<210> SEQ ID NO 95
<211> LENGTH: 38
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(38)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 95
gacgcgaccu uuuuguuccu uggcuccaag gucgcguc 38

<210> SEQ ID NO 96
<211> LENGTH: 38
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(38)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 96
gacgcgaccu uggcuuuaga gaguuccuug gucgcguc 38

<210> SEQ ID NO 97
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 97
ccacaguaaa uuugauuagu cgugugaaga aaacugucaa 40

<210> SEQ ID NO 98
<211> LENGTH: 43
<212> TYPE: RNA

<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(43)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 98
aaauagaaaa uuaaacgacc cugggaacgu gaauacccag ccu 43

<210> SEQ ID NO 99
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 99
ccucguacaa gguuuguaau ccacaguaag gaugagcuga 40

<210> SEQ ID NO 100
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 100
ggaaucuaaa auccggauag auaagaaagu uuggugagcc 40

<210> SEQ ID NO 101
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 101
cugcuccaug ugcaguuaca aauggccauc aauuggauuu 40

<210> SEQ ID NO 102
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 102
ugaauaacgc ggaaaucuag auaguaauac gguuuuuccc 40

<210> SEQ ID NO 103
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 103
agacucuaga augaugcaua ucguugcauu acgguugucu 40

<210> SEQ ID NO 104
<211> LENGTH: 36
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(36)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 104 ugacuucccuc uagaauacua uguacgguug ggguca 36

<210> SEQ ID NO 105
<211> LENGTH: 40
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(40)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 105
auagaagaau gacgucaaaa uaaccaaugu acugggcuac 40

<210> SEQ ID NO 106
<211> LENGTH: 32
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(32)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 106
gcgaccucua gaauaguaau acgguugguc gc 32

<210> SEQ ID NO 107
<211> LENGTH: 31
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(31)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 107
gcgacuuaug uguguucuau uuuuuggucg c 31

<210> SEQ ID NO 108
<211> LENGTH: 32
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(32)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 108
gcgaccucua gaaugguaac acgguugguc gc 32

<210> SEQ ID NO 109
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 109
gcgaccguuu uaugaaaaag acuuggggug cuacaugguc gc 42

<210> SEQ ID NO 110
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 110
gcgaccugug uccuaacuuu uguaucgaau gaucuggguc gc 42

<210> SEQ ID NO 111
<211> LENGTH: 41
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(41)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 111
gcgacuugug ucuaaacuuu uaucuauccu aguugggucg c 41

<210> SEQ ID NO 112
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 112
gcgaccaaag caucuagaua guaauacggu uugcucgguc gc 42

<210> SEQ ID NO 113
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 113
gcgaccucac acaaaauggu agccuauuau auauacgguc gc 42

<210> SEQ ID NO 114
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 114
gcgaccugaa uucuagaaug guaacacggu uauucugguc gc 42

<210> SEQ ID NO 115
<211> LENGTH: 52
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(52)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 115
acccuugcuu gcguagcauu uuaccaguga gucggaucuc cgcauaucug cg 52

<210> SEQ ID NO 116
<211> LENGTH: 43
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(43)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 116
ugccagugag ucggaucucc gcauaucugc gcgcauaucu gcg 43

<210> SEQ ID NO 117
<211> LENGTH: 52
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(52)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 117
acccuugcuu gcguagcauu cugccaguga gucggaucuc cgcauaucug cg 52

<210> SEQ ID NO 118
<211> LENGTH: 52
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(52)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 118
acccuugcuu gcgcagcauu cugccaguga gucggaucuc cgcauaucug cg 52

<210> SEQ ID NO 119
<211> LENGTH: 51
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(51)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 119
caccaugcuu gcguagcauc auccagugag ucggaucucc gcauaucugc g 51

<210> SEQ ID NO 120
<211> LENGTH: 50

<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(50)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 120
ccccaucugc gaagcaguca gccagugagu cggaucuccg cauaucugcg 50

<210> SEQ ID NO 121
<211> LENGTH: 45
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(45)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 121
cacagagaac ugugugccag ugagucggau cuccgcauau cugcg 45

<210> SEQ ID NO 122
<211> LENGTH: 41
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(41)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 122
cguagcauuu ugccagugag ucggaucucc gcauaucugc g 41

<210> SEQ ID NO 123
<211> LENGTH: 25
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(25)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 123
ugagucggau cuccgcauau cugcg 25

<210> SEQ ID NO 124
<211> LENGTH: 33
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(33)

<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 124
ugccagugag ucggaucucc ugugagaaca cag 33

<210> SEQ ID NO 125
<211> LENGTH: 55
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(55)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 125
cacagagaac ugugccuagc auuuugccag ugagucggau cuccgcauau cugcg 55

<210> SEQ ID NO 126
<211> LENGTH: 27
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(27)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 126
ugagcucgga ugcuccgcau aucugcg 27

<210> SEQ ID NO 127
<211> LENGTH: 52
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(52)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 127
uuuugugcuu gcguagcaac ccuccaguga gucggaucuc cgcauaucug cg 52

<210> SEQ ID NO 128
<211> LENGTH: 42
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 128
ugcaugcauu uuaccaguga gucggaucuc cgcauaucug cg 42

<210> SEQ ID NO 129
<211> LENGTH: 48
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(48)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 129
acccuugcuu gcguagcauu uuaccaguga gucggaucuc ugcaugca 48

<210> SEQ ID NO 130
<211> LENGTH: 30
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(30)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 130
uuuuaccagu gagucggauc ucugcaugca 30

<210> SEQ ID NO 131
<211> LENGTH: 43
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(43)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 131
ugcacugcau uuuaccagug agucggaucu ccgcauaucu gcg 43

<210> SEQ ID NO 132
<211> LENGTH: 44
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(44)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 132
ugcaucugca uuuuaccagu gagucggauc uccgcauauc ugcg 44

<210> SEQ ID NO 133
<211> LENGTH: 42
<212> TYPE: RNA
<213> ORGANISM: Artificial Sequence
<220> FEATURE:

<223> OTHER INFORMATION: modified anti-VEGF aptamer
<220> FEATURE:
<221> NAME/KEY: misc_feature
<222> LOCATION: (1)..(42)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 133
cuguacaguu uuaccaguga gucggaucuc cgcauaucug cg 42

<210> SEQ ID NO 134
<211> LENGTH: 45
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(45)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 134
uuuugcaugc auuuuaccag ugagucggau cuccgcauau cugcg 45

<210> SEQ ID NO 135
<211> LENGTH: 44
<212> TYPE: RNA
<213> ORGANISM: Artificial Sequence
<220> FEATURE:
<223> OTHER INFORMATION: modified anti-VEGF aptamer
<220> FEATURE:
<221> NAME/KEY: misc_feature
<222> LOCATION: (1)..(45)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 135
gcuguacagc uuuuaccagu gagucggauc uccgcauauc ugcg 44

<210> SEQ ID NO 136
<211> LENGTH: 17
<212> TYPE: RNA
<213> ORGANISM: Artificial Sequence
<220> FEATURE:
<223> OTHER INFORMATION: modified anti-VEGF aptamer first concensus sequence
<220> FEATURE:
<221> NAME/KEY: misc_feature
<222> LOCATION: (1)..(17)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 136
ccagugaguc ggaucuc 17

<210> SEQ ID NO 137
<211> LENGTH: 17
<212> TYPE: RNA
<213> ORGANISM: Artificial Sequence
<220> FEATURE:
<223> OTHER INFORMATION: natural anti-VEGF aptamer first concensus sequence

<400> SEQUENCE: 137
ccagugaguc ggaucuc 17

<210> SEQ ID NO 138
<211> LENGTH: 12
<212> TYPE: RNA
<213> ORGANISM: Artificial Sequence
<220> FEATURE:
<223> OTHER INFORMATION: modified anti-VEGF aptamer second concensus sequence
<220> FEATURE:
<221> NAME/KEY: misc_feature
<222> LOCATION: (1)..(12)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 138
cgcauaucug cg 12

<210> SEQ ID NO 139
<211> LENGTH: 12
<212> TYPE: RNA
<213> ORGANISM: Artificial Sequence
<220> FEATURE:
<223> OTHER INFORMATION: natural anti-VEGF aptamer second concensus sequence

<400> SEQUENCE: 139
cgcauaucug cg 12

<210> SEQ ID NO 140
<211> LENGTH: 88
<212> TYPE: RNA
<213> ORGANISM: Artificial Sequence
<220> FEATURE:
<223> OTHER INFORMATION: natural bispecifc aptamer

<400> SEQUENCE: 140
acccuugcuu gcguagcauu uuaccaguga gucggaucuc cgcauagaua agccaacaaa 60
cguacauucu cuguuaguau uuucugcg 88

<210> SEQ ID NO 141
<211> LENGTH: 81
<212> TYPE: RNA
<213> ORGANISM: Artificial Sequence
<220> FEATURE:
<223> OTHER INFORMATION: natural bispecifc aptamer

<400> SEQUENCE: 141
cgcauagaua agccaacaaa cguacauucu cuguuaguau uuucugcgug ccagugaguc 60
ggaucuccac aguucucugu g 81

<210> SEQ ID NO 142
<211> LENGTH: 67
<212> TYPE: RNA
<213> ORGANISM: Artificial Sequence
<220> FEATURE:
<223> OTHER INFORMATION: natural bispecifc aptamer

<400> SEQUENCE: 142
ugccagugag ucggaucucc gcauagauaa gccaacaaac guacauucuc uguuaguauu 60
uucugcg 67

<210> SEQ ID NO 143
<211> LENGTH: 69
<212> TYPE: RNA

<213> ORGANISM: Artificial Sequence
<220> FEATURE:
<223> OTHER INFORMATION: natural bispecifc aptamer

<400> SEQUENCE: 143
ugccagugag ucggaucucc acaguagaua agccaacaaa cguacauucu cuguuaguau 60
uuuccugug 69

<210> SEQ ID NO 144
<211> LENGTH: 78
<212> TYPE: RNA
<213> ORGANISM: Artificial Sequence
<220> FEATURE:
<223> OTHER INFORMATION: natural bispecifc aptamer

<400> SEQUENCE: 144
ugcaugcauu uuaccaguga gucggaucuc cgcauagaua agccaacaaa cguacauucu 60
cuguuaguau uuucugcg 78

<210> SEQ ID NO 145
<211> LENGTH: 76
<212> TYPE: RNA
<213> ORGANISM: Artificial Sequence
<220> FEATURE:
<223> OTHER INFORMATION: natural bispecifc aptamer

<400> SEQUENCE: 145
gcaugcuuuu accagugagu cggaucuccg cauagauaag ccaacaaacg uacauucucu 60
guuaguauuu ucugcg 76

<210> SEQ ID NO 146
<211> LENGTH: 80
<212> TYPE: RNA
<213> ORGANISM: Artificial Sequence
<220> FEATURE:
<223> OTHER INFORMATION: natural bispecifc aptamer

<400> SEQUENCE: 146
augcaugcau uuuuaccagu gagucggauc uccgcauaga uaagccaaca aacguacauu 60
cucuguuagu auuuucugcg 80

<210> SEQ ID NO 147
<211> LENGTH: 74
<212> TYPE: RNA
<213> ORGANISM: Artificial Sequence
<220> FEATURE:
<223> OTHER INFORMATION: natural bispecifc aptamer

<400> SEQUENCE: 147
ugcaugcaac cagugagucg gaucuccgca uagauaagcc aacaaacgua cauucucugu 60
uaguauuuuc ugcg 74

<210> SEQ ID NO 148
<211> LENGTH: 72
<212> TYPE: RNA
<213> ORGANISM: Artificial Sequence
<220> FEATURE:
<223> OTHER INFORMATION: natural bispecifc aptamer

<400> SEQUENCE: 148
ugcaugcaca gugagucgga ucuccgcaua gauaagccaa caaacguaca uucucuguua 60
guauuuucug cg 72

<210> SEQ ID NO 149
<211> LENGTH: 81
<212> TYPE: RNA
<213> ORGANISM: Artificial Sequence
<220> FEATURE:
<223> OTHER INFORMATION: natural bispecifc aptamer

<400> SEQUENCE: 149
uuuugcaugc auuuuaccag ugagucggau cuccgcauag auaagccaac aaacguacau 60
ucucuguuag uauuuucugc g 81

<210> SEQ ID NO 150
<211> LENGTH: 76
<212> TYPE: RNA
<213> ORGANISM: Artificial Sequence
<220> FEATURE:
<223> OTHER INFORMATION: natural bispecifc aptamer

<400> SEQUENCE: 150
ugcaugcauu accagugagu cggaucuccg cauagauaag ccaacaaacg uacauucucu 60
guuaguauuu ucugcg 76

<210> SEQ ID NO 151
<211> LENGTH: 80
<212> TYPE: RNA
<213> ORGANISM: Artificial Sequence
<220> FEATURE:
<223> OTHER INFORMATION: natural bispecifc aptamer

<400> SEQUENCE: 151
ugcaugcauu uuuuaccagu gagucggauc uccgcauaga uaagccaaca aacguacauu 60
cucuguuagu auuuucugcg 80

<210> SEQ ID NO 152
<211> LENGTH: 77
<212> TYPE: RNA
<213> ORGANISM: Artificial Sequence
<220> FEATURE:
<223> OTHER INFORMATION: natural bispecifc aptamer

<400> SEQUENCE: 152
ugcaugcauu uuccagugag ucggaucucc gcauagauaa gccaacaaac guacauucuc 60
uguuaguauu uucugcg 77

<210> SEQ ID NO 153
<211> LENGTH: 78
<212> TYPE: RNA
<213> ORGANISM: Artificial Sequence
<220> FEATURE:
<223> OTHER INFORMATION: natural bispecifc aptamer

<400> SEQUENCE: 153
cuguacaguu uuaccaguga gucggaucuc cgcauagaua agccaacaaa cguacauucu 60
cuguuaguau uuucugcg 78

<210> SEQ ID NO 154
<211> LENGTH: 80
<212> TYPE: RNA
<213> ORGANISM: Artificial Sequence
<220> FEATURE:
<223> OTHER INFORMATION: natural bispecifc aptamer

<400> SEQUENCE: 154
ccgguaccgg uuuuaccagu gagucggauc uccgcauaga uaagccaaca aacguacauu 60
cucuguuagu auuuucugcg 80

<210> SEQ ID NO 155
<211> LENGTH: 79
<212> TYPE: RNA
<213> ORGANISM: Artificial Sequence
<220> FEATURE:
<223> OTHER INFORMATION: natural bispecifc aptamer

<400> SEQUENCE: 155
ugcacugcau uuuaccagug agucggaucu ccgcauagau aagccaacaa acguacauuc 60
ucuguuagua uuuucugcg 79

<210> SEQ ID NO 156
<211> LENGTH: 80
<212> TYPE: RNA
<213> ORGANISM: Artificial Sequence
<220> FEATURE:
<223> OTHER INFORMATION: natural bispecifc aptamer

<400> SEQUENCE: 156
ugcaucugca uuuuaccagu gagucggauc uccgcauaga uaagccaaca aacguacauu 60
cucuguuagu auuuucugcg 80

<210> SEQ ID NO 157
<211> LENGTH: 81
<212> TYPE: RNA
<213> ORGANISM: Artificial Sequence
<220> FEATURE:
<223> OTHER INFORMATION: natural bispecifc aptamer

<400> SEQUENCE: 157
ugcaugcauu uuaccaguga gucggaucuc uuucgcauag auaagccaac aaacguacau 60
ucucuguuag uauuuucugc g 81

<210> SEQ ID NO 158
<211> LENGTH: 80
<212> TYPE: RNA
<213> ORGANISM: Artificial Sequence
<220> FEATURE:
<223> OTHER INFORMATION: natural bispecifc aptamer

<400> SEQUENCE: 158
gcuguacagc uuuuaccagu gagucggauc uccgcauaga uaagccaaca aacguacauu 60
cucuguuagu auuuucugcg 80

<210> SEQ ID NO 159
<211> LENGTH: 78
<212> TYPE: RNA
<213> ORGANISM: Artificial Sequence
<220> FEATURE:
<223> OTHER INFORMATION: natural bispecifc aptamer

<400> SEQUENCE: 159
ugcaugcauu uuaccaguga gucggaucuc cgcauagaua agccaacaaa cguacauucu 60
cuguuaguau uuucugcg 78

<210> SEQ ID NO 160
<211> LENGTH: 78

<212> TYPE: RNA
<213> ORGANISM: Artificial Sequence
<220> FEATURE:
<223> OTHER INFORMATION: natural bispecifc aptamer

<400> SEQUENCE: 160
ugcaugcauu uuaccaguga gucggaucuc cgcauagaua agccaacaaa cguacauucu 60
cuguuaguau uuucugcg 78

<210> SEQ ID NO 161
<211> LENGTH: 74
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (9)..(9)
<223> OTHER INFORMATION: n denotes hexa-ethyleneglycol (Heg) linker

<400> SEQUENCE: 161
ugcaugcanc cagugagucg gaucuccgca uagauaagcc aacaaacgua cauucucugu 60
uaguauuuuc ugcg 74

<210> SEQ ID NO 162
<211> LENGTH: 79
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (1)..(1)
<223> OTHER INFORMATION: n denotes hexa-ethyleneglycol (Heg) linker

<400> SEQUENCE: 162
nugcaugcau uuuaccagug agucggaucu ccgcauagau aagccaacaa acguacauuc 60
ucuguuagua uuuucugcg 79

<210> SEQ ID NO 163
<211> LENGTH: 73
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (51)..(51)
<223> OTHER INFORMATION: n denotes hexa-ethyleneglycol (Heg) linker

<400> SEQUENCE: 163
ugcaugcauu uuaccaguga gucggaucuc cgcauagaua agccaacaaa nuucucuguu 60
aguauuuucu gcg 73

<210> SEQ ID NO 164
<211> LENGTH: 75
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (52)..(52)
<223> OTHER INFORMATION: n denotes hexa-ethyleneglycol (Heg) linker

<400> SEQUENCE: 164
ugcaugcauu uuaccaguga gucggaucuc cgcauagaua agccaacaaa cnguucucug 60
uuaguauuuu cugcg 75

<210> SEQ ID NO 165
<211> LENGTH: 75
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (9)..(10)
<223> OTHER INFORMATION: n denotes three carbon linker

<400> SEQUENCE: 165
ugcaugcann ccagugaguc ggaucuccgc auagauaagc caacaaacgu acauucucug 60
uuaguauuuu cugcg 75

<210> SEQ ID NO 166
<211> LENGTH: 77
<212> TYPE: RNA
<213> ORGANISM: Artificial Sequence
<220> FEATURE:
<223> OTHER INFORMATION: natural bispecifc aptamer
<220> FEATURE:
<221> NAME/KEY: misc_feature
<222> LOCATION: (9)..(12)
<223> OTHER INFORMATION: n denotes three carbon linker

<400> SEQUENCE: 166
ugcaugcann nnccagugag ucggaucucc gcauagauaa gccaacaaac guacauucuc 60
uguuaguauu uucugcg 77

<210> SEQ ID NO 167
<211> LENGTH: 88
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(88)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 167
acccuugcuu gcguagcauu uuaccaguga gucggaucuc cgcauagaua agccaacaaa 60
cguacauucu cuguuaguau uuucugcg 88

<210> SEQ ID NO 168
<211> LENGTH: 81
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(81)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 168
cgcauagaua agccaacaaa cguacauucu cuguuaguau uuucugcgug ccagugaguc 60
ggaucuccac aguucucugu g 81

<210> SEQ ID NO 169
<211> LENGTH: 67
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(67)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 169
ugccagugag ucggaucucc gcauagauaa gccaacaaac guacauucuc uguuaguauu 60
uucugcg 67

<210> SEQ ID NO 170
<211> LENGTH: 69
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(69)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 170
ugccagugag ucggaucucc acaguagaua agccaacaaa cguacauucu cuguuaguau 60
uuuccugug 69

<210> SEQ ID NO 171
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(78)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 171
ugcaugcauu uuaccaguga gucggaucuc cgcauagaua agccaacaaa cguacauucu 60
cuguuaguau uuucugcg 78

<210> SEQ ID NO 172
<211> LENGTH: 76
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(76)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 172
gcaugcuuuu accagugagu cggaucuccg cauagauaag ccaacaaacg uacauucucu 60
guuaguauuu ucugcg 76

<210> SEQ ID NO 173
<211> LENGTH: 80
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(80)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 173
augcaugcau uuuuaccagu gagucggauc uccgcauaga uaagccaaca aacguacauu 60
cucuguuagu auuuucugcg 80

<210> SEQ ID NO 174
<211> LENGTH: 74
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(74)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 174
ugcaugcaac cagugagucg gaucuccgca uagauaagcc aacaaacgua cauucucugu 60
uaguauuuuc ugcg 74

<210> SEQ ID NO 175
<211> LENGTH: 72
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(72)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 175
ugcaugcaca gugagucgga ucuccgcaua gauaagccaa caaacguaca uucucuguua 60
guauuuucug cg 72

<210> SEQ ID NO 176
<211> LENGTH: 81
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(81)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 176
uuuugcaugc auuuuaccag ugagucggau cuccgcauag auaagccaac aaacguacau 60
ucucuguuag uauuuucugc g 81

<210> SEQ ID NO 177
<211> LENGTH: 76
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(76)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 177
ugcaugcauu accagugagu cggaucuccg cauagauaag ccaacaaacg uacauucucu 60
guuaguauuu ucugcg 76

<210> SEQ ID NO 178
<211> LENGTH: 80
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(80)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 178
ugcaugcauu uuuuaccagu gagucggauc uccgcauaga uaagccaaca aacguacauu 60
cucuguuagu auuuucugcg 80

<210> SEQ ID NO 179
<211> LENGTH: 77
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(77)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 179
ugcaugcauu uuccagugag ucggaucucc gcauagauaa gccaacaaac guacauucuc 60
uguuaguauu uucugcg 77

<210> SEQ ID NO 180
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(78)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 180

-continued cuguacaguu uuaccaguga gucggaucuc cgcauagaua agccaacaaa cguacauucu 60
cuguuaguau uuucugcg 78

<210> SEQ ID NO 181
<211> LENGTH: 80
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(80)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 181
ccgguaccgg uuuuaccagu gagucggauc uccgcauaga uaagccaaca aacguacauu 60
cucuguuagu auuuucugcg 80

<210> SEQ ID NO 182
<211> LENGTH: 79
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(79)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 182
ugcacugcau uuuaccagug agucggaucu ccgcauagau aagccaacaa acguacauuc 60
ucuguuagua uuuucugcg 79

<210> SEQ ID NO 183
<211> LENGTH: 80
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(80)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 183
ugcaucugca uuuuaccagu gagucggauc uccgcauaga uaagccaaca aacguacauu 60
cucuguuagu auuuucugcg 80

<210> SEQ ID NO 184
<211> LENGTH: 81
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(81)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 184
ugcaugcauu uuaccaguga gucggaucuc uuucgcauag auaagccaac aaacguacau 60
ucucuguuag uauuuucugc g 81

<210> SEQ ID NO 185
<211> LENGTH: 80
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(80)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 185
gcuguacagc uuuuaccagu gagucggauc uccgcauaga uaagccaaca aacguacauu 60
cucuguuagu auuuucugcg 80

<210> SEQ ID NO 186
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(18)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (19)..(21)
<223> OTHER INFORMATION: a represents locked nucleic acid (LNA) A, u represents locked nucleic acid (LNA) U, c represents locked nucleic acid (LNA) C, G represents locked nucleic acid (LNA) G
<220> FEATURE:
<221> NAME/KEY: misc_feature
<222> LOCATION: (22)..(28)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (29)..(29)
<223> OTHER INFORMATION: u represents locked nucleic acid (LNA) U
<220> FEATURE:
<221> NAME/KEY: misc_feature
<222> LOCATION: (30)..(78)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 186
ugcaugcauu uuaccaguga gucggaucuc cgcauagaua agccaacaaa cguacauucu 60
cuguuaguau uuucugcg 78

<210> SEQ ID NO 187
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(15)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (16)..(18)
<223> OTHER INFORMATION: a represents locked nucleic acid (LNA) A, u represents locked nucleic acid (LNA) U, c represents locked nucleic acid (LNA) C, g represents locked nucleic acid (LNA) G
<220> FEATURE:
<221> NAME/KEY: misc_feature
<222> LOCATION: (19)..(78)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 187
ugcaugcauu uuaccaguga gucggaucuc cgcauagaua agccaacaaa cguacauucu 60
cuguuaguau uuucugcg 78

<210> SEQ ID NO 188
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(8)
<223> OTHER INFORMATION: a represents locked nucleic acid (LNA) A, u represents locked nucleic acid (LNA) U, c represents locked nucleic acid (LNA) C, g represents locked nucleic acid (LNA) G
<220> FEATURE:
<221> NAME/KEY: misc_feature
<222> LOCATION: (9)..(30)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (31)..(34)
<223> OTHER INFORMATION: a represents locked nucleic acid (LNA) A, u represents locked nucleic acid (LNA) U, c represents locked nucleic acid (LNA) C, g represents locked nucleic acid (LNA) G
<220> FEATURE:
<221> NAME/KEY: misc_feature
<222> LOCATION: (35)..(74)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (75)..(78)
<223> OTHER INFORMATION: a represents locked nucleic acid (LNA) A, u represents locked nucleic acid (LNA) U, c represents locked nucleic acid (LNA) C, g represents locked nucleic acid (LNA) G

<400> SEQUENCE: 188
ugcaugcauu uuaccaguga gucggaucuc cgcauagaua agccaacaaa cguacauucu 60
cuguuaguau uuucugcg 78

<210> SEQ ID NO 189
<211> LENGTH: 78
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(8)
<223> OTHER INFORMATION: a represents 2'-O-methyl A, u represents 2'-O-methyl U, c represents 2'-O-methyl C, g represents 2'-O-methyl G
<220> FEATURE:
<221> NAME/KEY: misc_feature
<222> LOCATION: (9)..(30)

<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (31)..(34)
<223> OTHER INFORMATION: a represents 2'-O-methyl A, u represents 2'-O-methyl U, c represents 2'-O-methyl C, g represents 2'-O-methyl G
<220> FEATURE:
<221> NAME/KEY: misc_feature
<222> LOCATION: (35)..(74)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (75)..(78)
<223> OTHER INFORMATION: a represents 2'-O-methyl A, u represents 2'-O-methyl U, c represents 2'-O-methyl C, g represents 2'-O-methyl G

<400> SEQUENCE: 189
ugcaugcauu uuaccaguga gucggaucuc cgcauagaua agccaacaaa cguacauucu 60
cuguuaguau uuucugcg 78

<210> SEQ ID NO 190
<211> LENGTH: 74
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(8)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (9)..(9)
<223> OTHER INFORMATION: n denotes hexa-ethyleneglycol (Heg) linker
<220> FEATURE:
<221> NAME/KEY: misc_feature
<222> LOCATION: (10)..(74)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 190
ugcaugcanc cagugagucg gaucuccgca uagauaagcc aacaaacgua cauucucugu 60
uaguauuuuc ugcg 74

<210> SEQ ID NO 191
<211> LENGTH: 79
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(1)
<223> OTHER INFORMATION: n denotes hexa-ethyleneglycol (Heg) linker
<220> FEATURE:
<221> NAME/KEY: misc_feature
<222> LOCATION: (2)..(79)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 191
nugcaugcau uuuaccagug agucggaucu ccgcauagau aagccaacaa acguacauuc 60
ucuguuagua uuuucugcg 79

<210> SEQ ID NO 192
<211> LENGTH: 73
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(50)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (51)..(51)
<223> OTHER INFORMATION: n denotes hexa-ethyleneglycol (Heg) linker
<220> FEATURE:
<221> NAME/KEY: misc_feature
<222> LOCATION: (52)..(73)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 192
ugcaugcauu uuaccaguga gucggaucuc cgcauagaua agccaacaaa nuucucuguu 60
aguauuuucu gcg 73

<210> SEQ ID NO 193
<211> LENGTH: 75
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(51)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (52)..(52)
<223> OTHER INFORMATION: n denotes hexa-ethyleneglycol (Heg) linker
<220> FEATURE:
<221> NAME/KEY: misc_feature
<222> LOCATION: (53)..(75)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 193
ugcaugcauu uuaccaguga gucggaucuc cgcauagaua agccaacaaa cnguucucug 60
uuaguauuuu cugcg 75

<210> SEQ ID NO 194
<211> LENGTH: 75
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(8)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (9)..(10)
<223> OTHER INFORMATION: n denotes three carbon linker
<220> FEATURE:

<221> NAME/KEY: misc_feature
<222> LOCATION: (11)..(75)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 194
ugcaugcann ccagugaguc ggaucuccgc auagauaagc caacaaacgu acauucucug 60
uuaguauuuu cugcg 75

<210> SEQ ID NO 195
<211> LENGTH: 77
<212> TYPE: RNA
<213> ORGANISM: Artificial Sequence
<220> FEATURE:
<223> OTHER INFORMATION: modified bispecific aptamer
<220> FEATURE:
<221> NAME/KEY: misc_feature
<222> LOCATION: (1)..(8)
<223> OTHER INFORMATION: a represents 2'-fluoroadenylic acid, u represents 2'-fluorouridylic acid, c represents 2'-fluorocytidylic acid, g represents 2'-fluoroguanylic acid
<220> FEATURE:
<221> NAME/KEY: misc_feature
<222> LOCATION: (9)..(12)
<223> OTHER INFORMATION: n denotes three carbon linker
<220> FEATURE:
<221> NAME/KEY: misc_feature
<222> LOCATION: (13)..(77)
<223> OTHER INFORMATION: a represents 2'-fluoroadenylic acid, u represents 2'-fluorouridylic acid, c represents 2'-fluorocytidylic acid, g represents 2'-fluoroguanylic acid

<400> SEQUENCE: 195
ugcaugcann nnccagugag ucggaucucc gcauagauaa gccaacaaac guacauucuc 60
uguuaguauu uucugcg 77

<210> SEQ ID NO 196
<211> LENGTH: 17
<212> TYPE: DNA
<213> ORGANISM: Artificial Sequence
<220> FEATURE:
<223> OTHER INFORMATION: VEGF forward primer

<400> SEQUENCE: 196
cgccctcgtc ccatctc 17

<210> SEQ ID NO 197
<211> LENGTH: 18
<212> TYPE: DNA
<213> ORGANISM: Artificial Sequence
<220> FEATURE:
<223> OTHER INFORMATION: VEGF reverse primer

<400> SEQUENCE: 197
cgttctcggt tggtgttc 18

<210> SEQ ID NO 198
<211> LENGTH: 23
<212> TYPE: DNA
<213> ORGANISM: Artificial Sequence
<220> FEATURE:
<223> OTHER INFORMATION: Ang2 forward primer

<400> SEQUENCE: 198
atccagagtg acgctcttca gca 23

<210> SEQ ID NO 199
<211> LENGTH: 20
<212> TYPE: DNA
<213> ORGANISM: Artificial Sequence
<220> FEATURE:
<223> OTHER INFORMATION: Ang2 reverse primer

<400> SEQUENCE: 199
tgaagagcgt cactctggat 20

<210> SEQ ID NO 200
<211> LENGTH: 42
<212> TYPE: RNA
<213> ORGANISM: Artificial Sequence
<220> FEATURE:
<223> OTHER INFORMATION: AMS0433.m4
<220> FEATURE:
<221> NAME/KEY: misc_RNA
<222> LOCATION: (1)..(8)
<223> OTHER INFORMATION: 2'-F modification
<220> FEATURE:
<221> NAME/KEY: misc_RNA
<222> LOCATION: (9)..(14)
<223> OTHER INFORMATION: 2'-Ome modification
<220> FEATURE:
<221> NAME/KEY: misc_RNA
<222> LOCATION: (15)..(22)
<223> OTHER INFORMATION: 2'-F modification
<220> FEATURE:
<221> NAME/KEY: misc_RNA
<222> LOCATION: (23)..(23)
<223> OTHER INFORMATION: 2'-Ome modification
<220> FEATURE:
<221> NAME/KEY: misc_RNA
<222> LOCATION: (24)..(26)
<223> OTHER INFORMATION: 2'-F modification
<220> FEATURE:
<221> NAME/KEY: misc_RNA
<222> LOCATION: (27)..(27)
<223> OTHER INFORMATION: 2'-Ome modification
<220> FEATURE:
<221> NAME/KEY: misc_RNA
<222> LOCATION: (28)..(30)
<223> OTHER INFORMATION: 2'-F modification
<220> FEATURE:
<221> NAME/KEY: misc_RNA
<222> LOCATION: (31)..(42)
<223> OTHER INFORMATION: 2'-Ome modification

<400> SEQUENCE: 200
ugcaugcauu uuaccaguga gucggaucuc cgcauaucug cg 42

<210> SEQ ID NO 201
<211> LENGTH: 42
<212> TYPE: RNA
<213> ORGANISM: Artificial Sequence
<220> FEATURE:
<223> OTHER INFORMATION: AMS0433.m6
<220> FEATURE:
<221> NAME/KEY: misc_RNA
<222> LOCATION: (1)..(14)
<223> OTHER INFORMATION: 2'-Ome modification
<220> FEATURE:
<221> NAME/KEY: misc_RNA
<222> LOCATION: (15)..(22)
<223> OTHER INFORMATION: 2'-F modification
<220> FEATURE:
<221> NAME/KEY: misc_RNA
<222> LOCATION: (23)..(23)
<223> OTHER INFORMATION: 2'-Ome modification
<220> FEATURE:
<221> NAME/KEY: misc_RNA
<222> LOCATION: (24)..(26)
<223> OTHER INFORMATION: 2'-F modification
<220> FEATURE:

<221> NAME/KEY: misc_RNA
<222> LOCATION: (27)..(27)
<223> OTHER INFORMATION: 2'-Ome modification
<220> FEATURE:
<221> NAME/KEY: misc_RNA
<222> LOCATION: (28)..(42)
<223> OTHER INFORMATION: 2'-F modification

<400> SEQUENCE: 201
ugcaugcauu uuaccaguga gucggaucuc cgcauaucug cg 42

<210> SEQ ID NO 202
<211> LENGTH: 74
<212> TYPE: RNA
<213> ORGANISM: Artificial Sequence
<220> FEATURE:
<223> OTHER INFORMATION: AMSB107.P6
<220> FEATURE:
<221> NAME/KEY: misc_RNA
<222> LOCATION: (1)..(74)
<223> OTHER INFORMATION: 2'-F modification
<220> FEATURE:
<221> NAME/KEY: misc_RNA
<222> LOCATION: (9)..(9)
<223> OTHER INFORMATION: H is A, U or C

<400> SEQUENCE: 202
ugcaugcahc cagugagucg gaucuccgca uagauaagcc aacaaacgua cauucucugu 60
uaguauuuuc ugcg 74

<210> SEQ ID NO 203
<211> LENGTH: 74
<212> TYPE: RNA
<213> ORGANISM: Artificial Sequence
<220> FEATURE:
<223> OTHER INFORMATION: AMSB107.P40K
<220> FEATURE:
<221> NAME/KEY: misc_RNA
<222> LOCATION: (1)..(74)
<223> OTHER INFORMATION: 2'-F modification
<220> FEATURE:
<221> NAME/KEY: misc_feature
<222> LOCATION: (1)..(74)
<223> OTHER INFORMATION: With 40kDa PEG conjugated at 5'-end
<220> FEATURE:
<221> NAME/KEY: misc_RNA
<222> LOCATION: (9)..(9)
<223> OTHER INFORMATION: H is A, U or C

<400> SEQUENCE: 203
ugcaugcahc cagugagucg gaucuccgca uagauaagcc aacaaacgua cauucucugu 60
uaguauuuuc ugcg 74

<210> SEQ ID NO 204
<211> LENGTH: 78
<212> TYPE: RNA
<213> ORGANISM: Artificial Sequence
<220> FEATURE:
<223> OTHER INFORMATION: AMSB107P
<220> FEATURE:
<221> NAME/KEY: misc_RNA
<222> LOCATION: (1)..(8)
<223> OTHER INFORMATION: 2'-F modification
<220> FEATURE:
<221> NAME/KEY: misc_RNA
<222> LOCATION: (9)..(14)
<223> OTHER INFORMATION: 2'-Ome modification
<220> FEATURE:
<221> NAME/KEY: misc_RNA
<222> LOCATION: (15)..(22)
<223> OTHER INFORMATION: 2'-F modification -continued

```
<220> FEATURE:
<221> NAME/KEY: misc_RNA
<222> LOCATION: (23)..(23)
<223> OTHER INFORMATION: 2'-Ome modification
<220> FEATURE:
<221> NAME/KEY: misc_RNA
<222> LOCATION: (24)..(26)
<223> OTHER INFORMATION: 2'-F modification
<220> FEATURE:
<221> NAME/KEY: misc_RNA
<222> LOCATION: (27)..(27)
<223> OTHER INFORMATION: 2'-Ome modification
<220> FEATURE:
<221> NAME/KEY: misc_RNA
<222> LOCATION: (28)..(34)
<223> OTHER INFORMATION: 2'-F modification
<220> FEATURE:
<221> NAME/KEY: misc_RNA
<222> LOCATION: (35)..(36)
<223> OTHER INFORMATION: 2'-Ome modification
<220> FEATURE:
<221> NAME/KEY: misc_RNA
<222> LOCATION: (37)..(50)
<223> OTHER INFORMATION: 2'-F modification
<220> FEATURE:
<221> NAME/KEY: misc_RNA
<222> LOCATION: (51)..(56)
<223> OTHER INFORMATION: 2'-Ome modification
<220> FEATURE:
<221> NAME/KEY: misc_RNA
<222> LOCATION: (57)..(74)
<223> OTHER INFORMATION: 2'-F modification
<220> FEATURE:
<221> NAME/KEY: misc_RNA
<222> LOCATION: (75)..(78)
<223> OTHER INFORMATION: 2'-Ome modification

<400> SEQUENCE: 204

ugcaugcauu uuaccaguga gucggaucuc cgcauagaua agccaacaaa cguacauucu     60

cuguuaguau uuucugcg                                                   78
```